(12) United States Patent
Kim et al.

(10) Patent No.: US 11,802,116 B2
(45) Date of Patent: Oct. 31, 2023

(54) DIAMINE COMPOUND AND ORGANIC LIGHT-EMITTING DEVICE INCLUDING THE SAME

(71) Applicant: Samsung Display Co., Ltd., Yongin-si (KR)

(72) Inventors: Jongwoo Kim, Yongin-si (KR); Dongjun Kim, Yongin-si (KR); Youngkook Kim, Yongin-si (KR); Eunjae Jeong, Yongin-si (KR); Sanghyun Han, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 515 days.

(21) Appl. No.: 16/293,299

(22) Filed: Mar. 5, 2019

(65) Prior Publication Data

US 2019/0389828 A1    Dec. 26, 2019

(30) Foreign Application Priority Data

Jun. 20, 2018   (KR) .......................... 10-2018-0070904

(51) Int. Cl.
*C07D 307/91*    (2006.01)
*C07D 333/76*    (2006.01)
(Continued)

(52) U.S. Cl.
CPC .......... *C07D 307/91* (2013.01); *C07D 333/76* (2013.01); *C07D 409/12* (2013.01);
(Continued)

(58) Field of Classification Search
CPC ................ C07D 307/91; C07D 333/76; C07D 409/12; H01L 51/0052; H01L 51/006; H01L 51/0061; H01L 51/0073; H01L 51/0074; H01L 51/0081; H01L 51/5012; H01L 51/5056; H01L 51/506; H10K 85/615;
(Continued)

(56) References Cited

U.S. PATENT DOCUMENTS 8,026,514 B2   9/2011 Jang et al.
8,288,014 B2   10/2012 Hwang et al.
(Continued)

FOREIGN PATENT DOCUMENTS

CN    106910831 A    6/2017
KR    10-2008-0096440 A    10/2008
(Continued)

OTHER PUBLICATIONS

Translation for KR 20100123172 A (publication date Nov. 2010). (Year: 2010).*
(Continued)

*Primary Examiner* — Dawn L Garrett
(74) *Attorney, Agent, or Firm* — Lewis Roca Rothgerber Christie LLP

(57) ABSTRACT

Provided are a diamine compound and an organic light-emitting device including the same. The organic light-emitting device includes: a first electrode; a second electrode; and an organic layer between the first electrode and the second electrode and comprising an emission layer, the organic layer including a diamine compound represented by one selected from Formulae 1-1 to 1-8.

17 Claims, 2 Drawing Sheets

(51) Int. Cl.
  *C07D 409/12* (2006.01)
  *H10K 85/60* (2023.01)
  *H10K 50/11* (2023.01)
  *H10K 50/155* (2023.01)

(52) U.S. Cl.
  CPC ......... *H10K 85/615* (2023.02); *H10K 85/633* (2023.02); *H10K 85/636* (2023.02); *H10K 85/6574* (2023.02); *H10K 85/6576* (2023.02); *H10K 50/11* (2023.02); *H10K 50/155* (2023.02)

(58) Field of Classification Search
  CPC ............... H10K 85/633; H10K 85/636; H10K 85/6574; H10K 85/6576; H10K 50/11; H10K 50/155; H10K 50/15; H10K 85/324; H10K 50/17; H10K 85/626; H10K 85/657
  See application file for complete search history.

(56) References Cited

U.S. PATENT DOCUMENTS

| | | | |
|---|---|---|---|
| 8,298,684 B2 | 10/2012 | Kwang et al. | |
| 8,394,511 B2 | 3/2013 | Hwang et al. | |
| 10,069,085 B2 * | 9/2018 | Lee | H01L 51/0077 |
| 2003/0118866 A1 * | 6/2003 | Oh | C09B 23/148 |
| | | | 428/917 |
| 2009/0200928 A1 * | 8/2009 | Hwang | C07D 209/88 |
| | | | 313/504 |
| 2010/0032656 A1 * | 2/2010 | Kwang | C07D 209/88 |
| | | | 257/40 |
| 2010/0187504 A1 * | 7/2010 | Jang | C07C 211/58 |
| | | | 564/426 |
| 2012/0319091 A1 | 12/2012 | Kato | |
| 2017/0179395 A1 | 6/2017 | Kim et al. | |
| 2017/0288148 A1 * | 10/2017 | Park | H01L 51/0067 |

FOREIGN PATENT DOCUMENTS

| | | | |
|---|---|---|---|
| KR | 10-2009-0086756 A | | 8/2009 |
| KR | 10-2009-0120699 A | | 11/2009 |
| KR | 20100123172 A | * | 11/2010 |
| KR | 10-2012-0096097 A | | 8/2012 |
| KR | 1020160059609 A | * | 5/2016 |
| KR | 10-2018-0009429 A | | 1/2018 |

OTHER PUBLICATIONS

Chem. Rev. (2007), 107, pp. 953-1010. (Year: 2007).*
Machine translation of KR 1020160059609 A (publication date: May 2016). (Year: 2016).*
Ku et al., Journal of the Chinese Chemical Society, (2006), 53, pp. 1317-1324. (Year: 2006).*
Machine translation KR 20160059609 A (patent document publication date May 2016). (Year: 2016).*

* cited by examiner

DIAMINE COMPOUND AND ORGANIC LIGHT-EMITTING DEVICE INCLUDING THE SAME

CROSS-REFERENCE TO RELATED APPLICATION

This application claims the benefit of Korean Patent Application No. 10-2018-0070904, filed on Jun. 20, 2018, in the Korean Intellectual Property Office, the entire content of which is incorporated herein by reference.

BACKGROUND

1. Field

One or more embodiments relate to a diamine compound and an organic light-emitting device including the same.

2. Description of the Related Art

Organic light-emitting devices are self-emission devices, have wide viewing angles, high contrast ratios, short response times, as well as excellent characteristics in terms of brightness, driving voltage, and response speed, and produce full-color images.

An example of such organic light-emitting devices may include a first electrode on a substrate, and a hole transport region, an emission layer, an electron transport region, and a second electrode, which are sequentially on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit (e.g., transition or relax) from an excited state to a ground state, thereby generating light.

SUMMARY

One or more embodiments of the present disclosure provide a diamine compound and an organic light-emitting device including the same.

Additional aspects of embodiments will be set forth in part in the description which follows and, in part, will be apparent from the description, or may be learned by practice of the presented embodiments.

An aspect of an embodiment provides an organic light-emitting device including: a first electrode; a second electrode; an organic layer between the first electrode and the second electrode and including an emission layer, wherein the organic layer includes a diamine compound represented by one selected from Formulae 1-1 to 1-8:

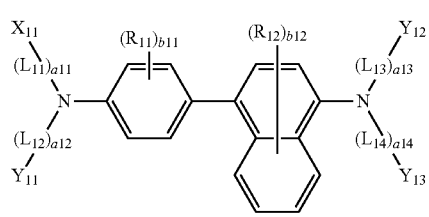

1-1

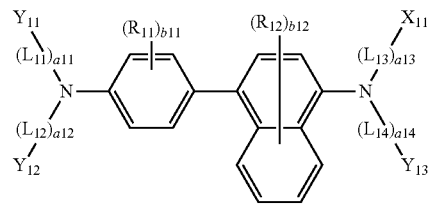

1-2

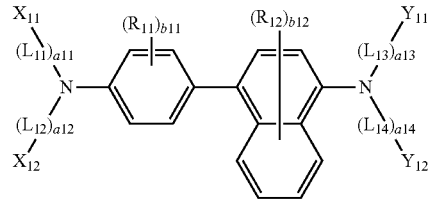

1-3

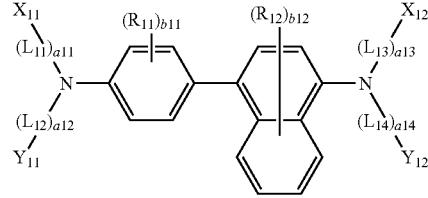

1-4

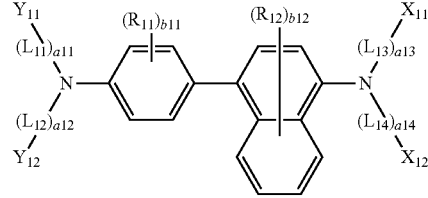

1-5

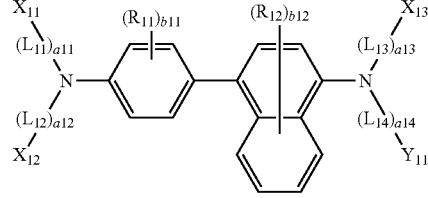

1-6

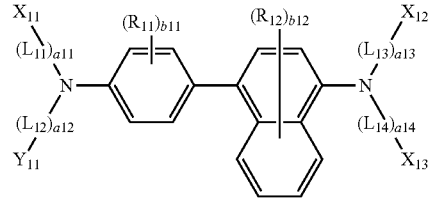

1-7

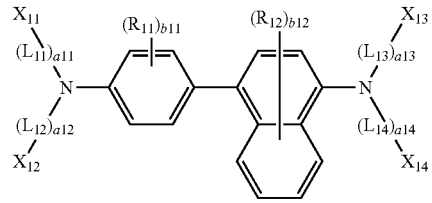

1-8

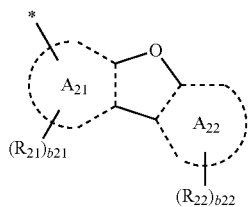

2-1

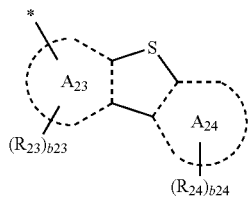

2-2

In Formulae 1-1 to 1-8, $X_{11}$ to $X_{14}$ may each independently be represented by one selected from Formulae 2-1 and 2-2, wherein $X_{11}$ to $X_{14}$ are different from each other, $Y_{11}$ to $Y_{13}$ may each independently be selected from:

a $C_6$-$C_{60}$ aryl group, a $C_1$-$C_{60}$ heteroaryl group, a biphenyl group, and a terphenyl group; and a $C_6$-$C_{60}$ aryl group, a $C_1$-$C_{60}$ heteroaryl group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), $L_{11}$ to $L_{14}$ may each independently be selected from:

a single bond, a $C_6$-$C_{60}$ arylene group, a $C_1$-$C_{60}$ heteroarylene group, a biphenylene group, and a terphenylene group; and a $C_6$-$C_{60}$ arylene group, a $C_1$-$C_{60}$ heteroarylene group, a biphenylene group, and a terphenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), a11 to a14 may each independently be selected from 0, 1, 2, and 3, $R_{11}$ and $R_{12}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), b11 may be selected from 1, 2, 3, 4, 5, and 6, and b12 may be selected from 1, 2, 3, and 4, in Formulae 2-1 and 2-2, $A_{21}$ to $A_{24}$ may each independently be selected from a benzene group, a naphthalene group, an anthracene group, a phenanthrene group, a chrysene group, a pyrene group, a pentaphene group, a triphenylene group, and a phenylene group, b21 to b24 may each independently be selected from 1, 2, 3, 4, 5, 6, 7, 8, 9, and 10, and $R_{21}$ to $R_{24}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), $Q_1$ to $Q_3$ may each independently be selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group, and

* indicates a binding site to a neighboring atom.

In one embodiment, the first electrode may be an anode, the second electrode may be a cathode, the organic layer may further include a hole transport region between the first electrode and the emission layer, and the hole transport region may include the diamine compound.

In one embodiment, the hole transport region may include at least one selected from a hole injection layer and a hole transport layer, and at least one selected from the hole injection layer and the hole transport layer may include the diamine compound.

In one embodiment, the hole transport region may include a p-dopant, and the p-dopant may have a lowest unoccupied molecular orbital (LUMO) energy level of about −3.5 eV or less.

In one or more embodiments, the diamine compound may be represented by one selected from Formulae 1-1 to 1-8:

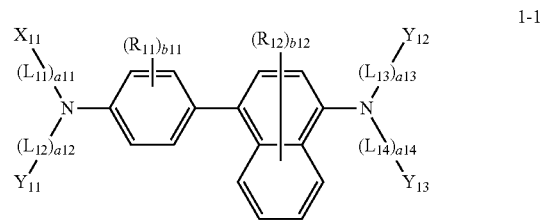

1-1

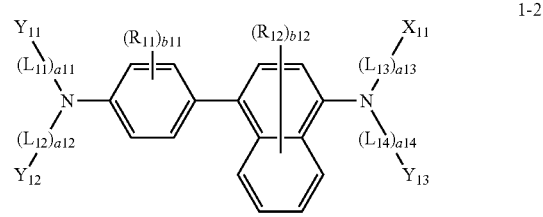

1-2

-continued

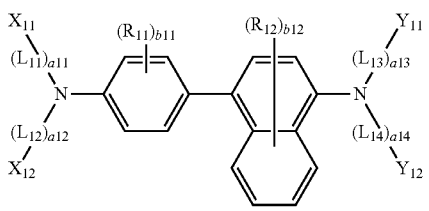

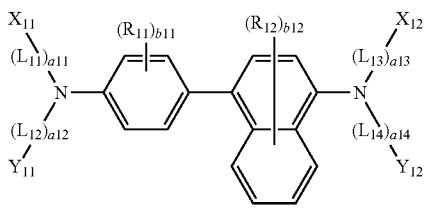

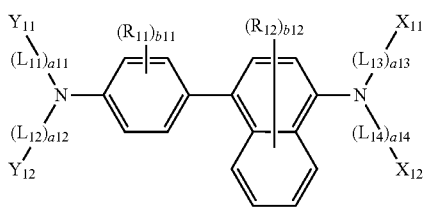

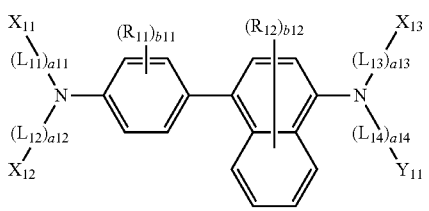

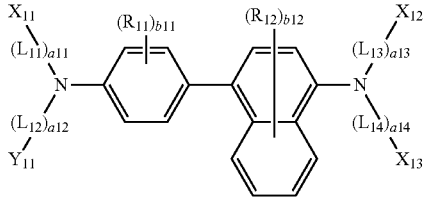

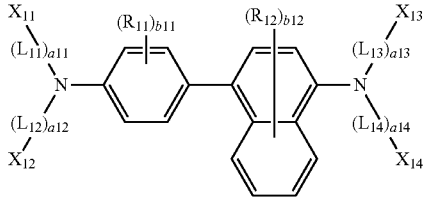

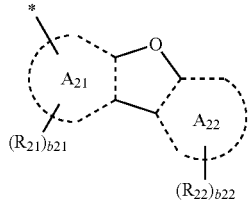

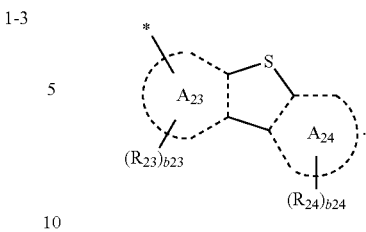

In Formulae 1-1 to 1-8, $X_{11}$ to $X_{14}$ may each independently be represented by one selected from Formulae 2-1 and 2-2, wherein $X_{11}$ to $X_{14}$ are different from each other, $Y_{11}$ to $Y_{13}$ may each independently be selected from:

a $C_6$-$C_{60}$ aryl group, a $C_1$-$C_{60}$ heteroaryl group, a biphenyl group, and a terphenyl group; and a $C_6$-$C_{60}$ aryl group, a $C_1$-$C_{60}$ heteroaryl group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si$(Q_1)(Q_2)(Q_3)$, $L_{11}$ to $L_{14}$ may each independently be selected from:

a single bond, a $C_6$-$C_{60}$ arylene group, a $C_1$-$C_{60}$ heteroarylene group, a biphenylene group, and a terphenylene group; and a $C_6$-$C_{60}$ arylene group, a $C_1$-$C_{60}$ heteroarylene group, a biphenylene group, and a terphenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si$(Q_1)(Q_2)(Q_3)$, a11 to a14 may each independently be selected from 0, 1, 2, and 3, $R_{11}$ and $R_{12}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si$(Q_1)(Q_2)(Q_3)$, b11 may be selected from 1, 2, 3, 4, 5, and 6, and b12 may be selected from 1, 2, 3, and 4, in Formulae 2-1 and 2-2, $A_{21}$ to $A_{24}$ may each independently be selected from a benzene group, a naphthalene group, an anthracene group, a phenanthrene group, a chrysene group, a pyrene group, a pentaphene group, a triphenylene group, and a phenylene group, b21 to b24 may each independently be selected from 1, 2, 3, 4, 5, 6, 7, 8, 9, and 10, and $R_{21}$ to $R_{24}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), $Q_1$ to $Q_3$ may each independently be selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_6$-$C_{60}$ heteroaryl group, a biphenyl group, and a terphenyl group, and

* indicates a binding site to a neighboring atom.

BRIEF DESCRIPTION OF THE DRAWINGS

These and/or other aspects of embodiments will become apparent and more readily appreciated from the following description of the embodiments, taken in conjunction with the accompanying drawings in which.

DETAILED DESCRIPTION

Figure 1:
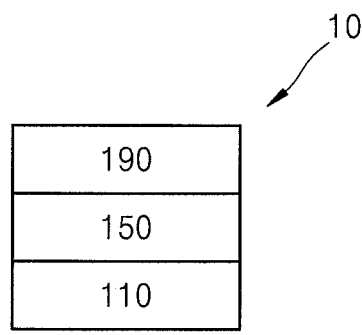
FIG. 1 is a schematic cross-sectional view of an organic light-emitting device according to an embodiment.

The subject matter of the present disclosure will now be described more fully with reference to exemplary embodiments. The subject matter of the present disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Features of the subject matter of the disclosure, and how to achieve them, will become apparent by reference to the embodiments that will be described herein below in more detail, together with the accompanying drawings. The subject matter of the present disclosure may, however, be embodied in many different forms and should not be limited to the exemplary embodiments.

Hereinafter, embodiments are described in more detail by referring to the attached drawings, and in the drawings, like reference numerals denote like elements, and a redundant explanation thereof may not be repeated herein.

As used herein, the singular forms "a," "an" and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components. As used herein, the term "and/or" includes any and all combinations of one or more of the associated listed items. Expressions such as "at least one of," when preceding a list of elements, modify the entire list of elements and do not modify the individual elements of the list.

It will be understood that when a layer, region, or component is referred to as being "on" or "onto" another layer, region, or component, it may be directly or indirectly formed on the other layer, region, or component. For example, intervening layers, regions, or components may be present. In addition, it will also be understood that when an element or layer is referred to as being "between" two elements or layers, it can be the only element or layer between the two elements or layers, or one or more intervening elements or layers may also be present.

Sizes of components in the drawings may be exaggerated for convenience of explanation. In other words, since sizes and thicknesses of components in the drawings may be arbitrarily illustrated for convenience of explanation, the following embodiments of the present disclosure are not limited thereto.

An organic light-emitting device according to an embodiment may include: a first electrode; a second electrode; an organic layer between the first electrode and the second electrode and including an emission layer, wherein the organic layer includes a diamine component represented by one selected from Formulae 1-1 to 1-8:

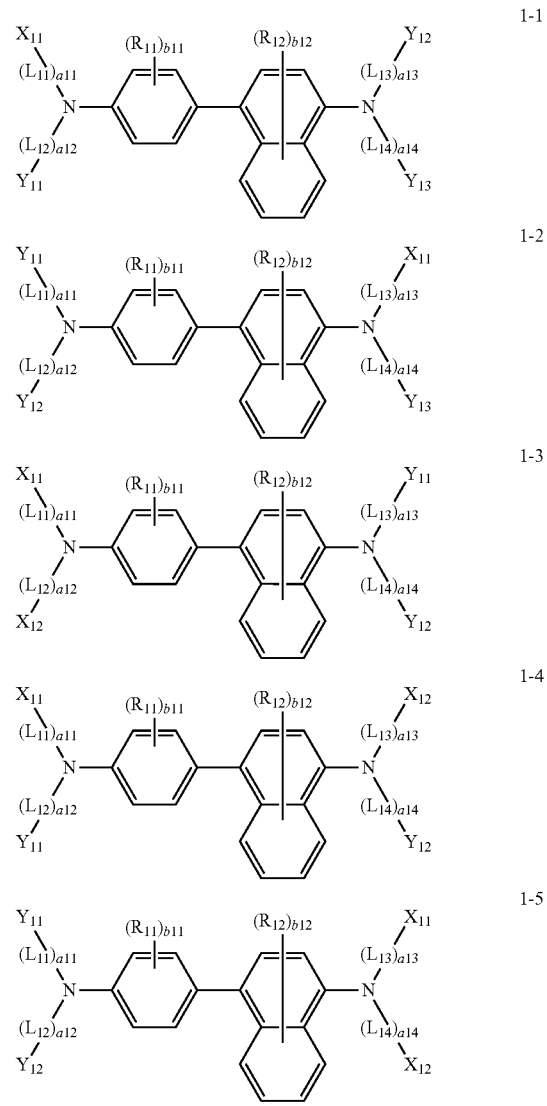

-continued

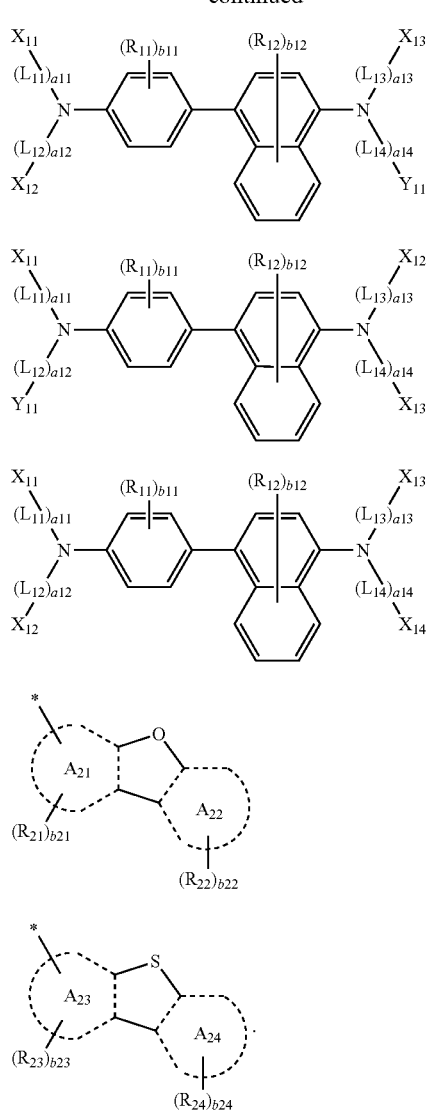

1-6

1-7

1-8

2-1

2-2

In Formulae 1-1 to 1-8, $X_{11}$ to $X_{14}$ may each independently be represented by one selected from Formulae 2-1 and 2-2, wherein $X_{11}$ to $X_{14}$ are different from each other, $Y_{11}$ to $Y_{13}$ may each independently be selected from:

a $C_6$-$C_{60}$ aryl group, a $C_1$-$C_{60}$ heteroaryl group, a biphenyl group, and a terphenyl group; and a $C_6$-$C_{60}$ aryl group, a $C_1$-$C_{60}$ heteroaryl group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), $L_{11}$ to $L_{14}$ may each independently be selected from:

a single bond, a $C_6$-$C_{60}$ arylene group, a $C_1$-$C_{60}$ heteroarylene group, a biphenylene group, and a terphenylene group; and a $C_6$-$C_{60}$ arylene group, a $C_1$-$C_{60}$ heteroarylene group, a biphenylene group, and a terphenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), a11 to a14 may each independently be selected from 0, 1, 2, and 3, $R_{11}$ and $R_{12}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), b11 may be selected from 1, 2, 3, 4, 5, and 6, and b12 may be selected from 1, 2, 3, and 4, in Formulae 2-1 and 2-2, $A_{21}$ to $A_{24}$ may each independently be selected from a benzene group, a naphthalene group, an anthracene group, a phenanthrene group, a chrysene group, a pyrene group, a pentaphene group, a triphenylene group, and phenylene group, b21 to b24 may each independently be selected from 1, 2, 3, 4, 5, 6, 7, 8, 9, and 10, and $R_{21}$ to $R_{24}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), $Q_1$ to $Q_3$ may each independently be selected from hydrogen, deuterium, a $C_6$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group, and

* indicates a binding site to a neighboring atom.

For example, the first electrode may be an anode, the second electrode may be a cathode, the organic layer may further include a hole transport region between the first electrode and the emission layer, and the hole transport region may include the diamine compound, but embodiments of the present disclosure are not limited thereto.

In one embodiment, the hole transport region may include at least one selected from a hole injection layer and a hole transport layer, and at least one selected from the hole injection layer and the hole transport layer may include the diamine compound, but embodiments of the present disclosure are not limited thereto.

In one embodiment, the hole transport region may include a p-dopant, and the p-dopant may have a lowest unoccupied molecular orbital (LUMO) energy level of about −3.5 eV or less, but embodiments of the present disclosure are not limited thereto.

In one or more embodiments, the diamine compound may be represented by one selected from Formulae 1-1 to 1-8:

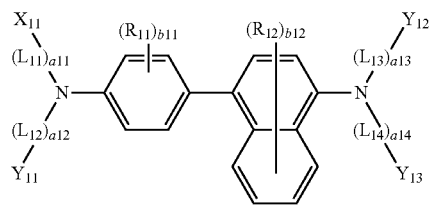

1-1

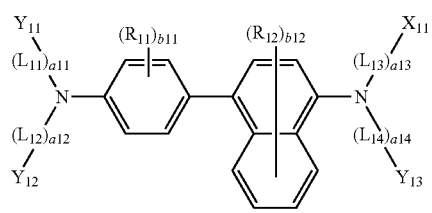

1-2

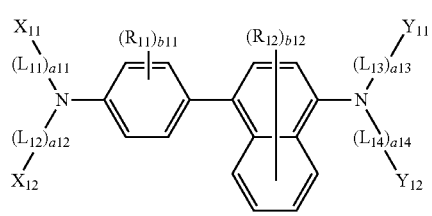

1-3

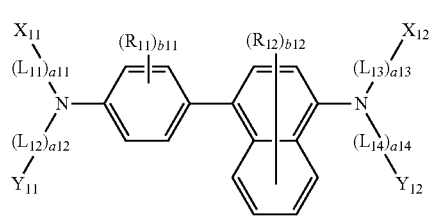

1-4

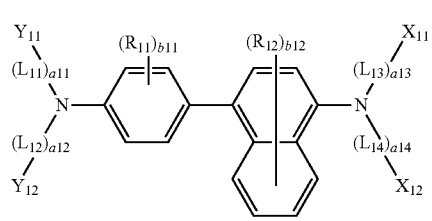

1-5

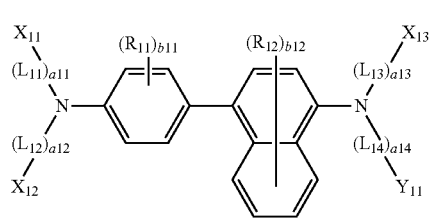

1-6

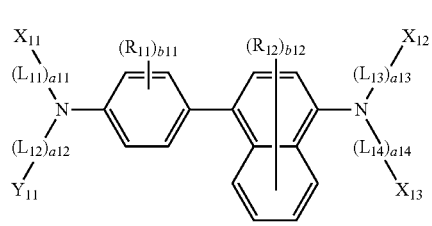

1-7

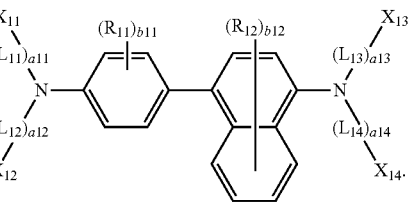

1-8

In Formulae 1-1 to 1-8, $X_{11}$ to $X_{14}$ may each independently be represented by one selected from Formulae 2-1 and 2-2, wherein $X_{11}$ to $X_{14}$ are different from each other:

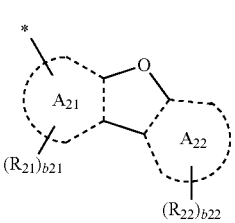

2-1

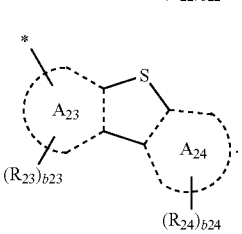

2-2

In Formulae 2-1 and 2-2, $A_{21}$ to $A_{24}$, $R_{21}$ to $R_{24}$, and b21 to b24 may each independently be the same as described below, and * indicates a binding site to a neighboring atom.

For example, in Formulae 1-1 to 1-8, $X_{11}$ to $X_{14}$ may be different from each other, i) $X_{11}$ to $X_{14}$ may each independently be represented by Formula 2-1, or ii) $X_{11}$ to $X_{14}$ may each independently be represented by Formula 2-2, but embodiments of the present disclosure are not limited thereto.

In one embodiment, in Formulae 1-3 to 1-5, $X_{11}$ to $X_{14}$ may be different from each other, i) $X_{11}$ and $X_{12}$ may each independently be represented by Formula 2-1;

ii) $X_{11}$ may be represented by Formula 2-1, and $X_{12}$ may be represented by Formula 2-2;

iii) $X_{11}$ may be represented by Formula 2-2, and $X_{12}$ may be represented by Formula 2-1; or iv) $X_{11}$ and $X_{12}$ may each independently be represented by Formula 2-2, but embodiments of the present disclosure are not limited thereto.

In Formulae 2-1 and 2-2, $A_{21}$ to $A_{24}$ may each independently be selected from a benzene group, a naphthalene group, an anthracene group, a phenanthrene group, a chrysene group, a pyrene group, a pentaphene group, a triphenylene group, and a phenylene group.

For example, in Formulae 2-1 and 2-2, $A_{21}$ to $A_{24}$ may each independently be selected from a benzene group and a naphthalene group, but embodiments of the present disclosure are not limited thereto.

In Formulae 1-1 to 1-8, $Y_{11}$ to $Y_{13}$ may each independently be selected from:

a $C_6$-$C_{60}$ aryl group, a $C_1$-$C_{60}$ heteroaryl group, a biphenyl group, and a terphenyl group; and a $C_6$-$C_{60}$ aryl group, a $C_1$-$C_{60}$ heteroaryl group, a biphenyl group, and a terphenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si($Q_1$)($Q_2$)($Q_3$), and $Q_1$ to $Q_3$ may each independently be selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group.

For example, in Formulae 1-1 to 1-8, $Y_{11}$ to $Y_{13}$ may each independently be selected from:

a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group; and a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group, each substituted with at least one selected from deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, a butoxy group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, a phenanthrolinyl group, and —Si($Q_1$)($Q_2$)($Q_3$), and $Q_1$ to $Q_3$ may each independently be selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, a terphenyl group, and a naphthyl group, but embodiments of the present disclosure are not limited thereto.

In one embodiment, in Formulae 1-1 to 1-8, $Y_{11}$ to $Y_{13}$ may each independently be selected from:

a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, and a furanyl group; and a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, and a furanyl group, each substituted with at least one selected from deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, a furanyl group, and —Si($Q_1$)($Q_2$)($Q_3$), and $Q_1$ to $Q_3$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an isopropyl group, an n-butyl group, an isobutyl group, a sec-butyl group, a tert-butyl group, a phenyl group, a biphenyl group, a terphenyl group, and a naphthyl group, but embodiments of the present disclosure are not limited thereto.

In one embodiment, in Formulae 1-1 to 1-8, $Y_{11}$ to $Y_{13}$ may each independently be selected from groups represented by Formulae 5-1 to 5-11, but embodiments of the present disclosure are not limited thereto:

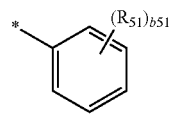

5-1

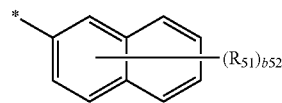

5-2

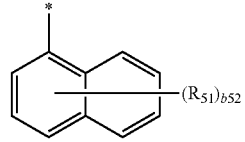

5-3

-continued

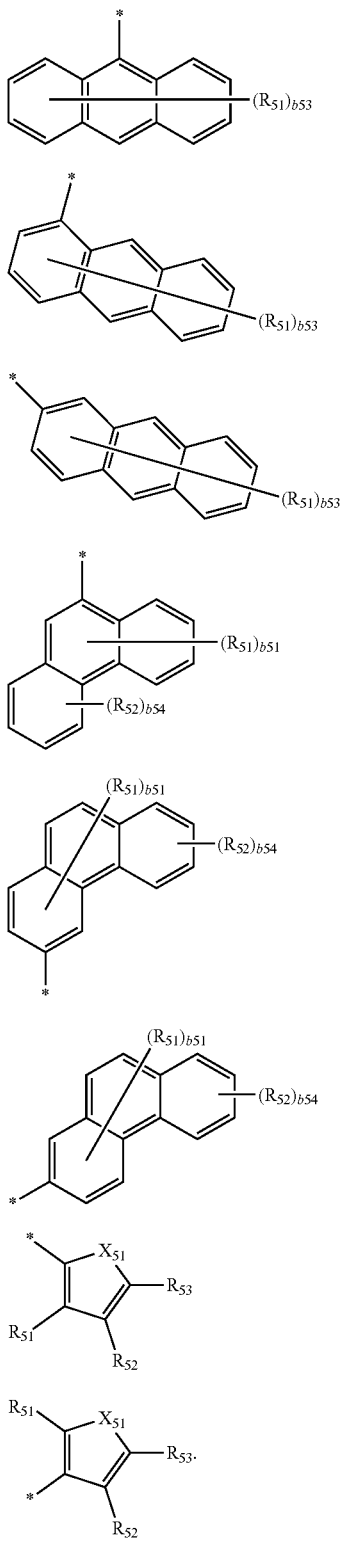

5-4

5-5

5-6

5-7

5-8

5-9

5-10

5-11

In Formulae 5-1 to 5-11, $X_{51}$ may be selected from O and S, $R_{51}$ to $R_{53}$ may each independently be selected from hydrogen, deuterium, —F, —Cl, —Br, —I, —$CD_3$, —$CD_2H$, —$CDH_2$, —$CF_3$, —$CF_2H$, —$CFH_2$, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, a furanyl group, and —Si($Q_1$)($Q_2$)($Q_3$), $Q_1$ to $Q_3$ may each independently be selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$; and an n-propyl group, an isopropyl group, an n-butyl group, an isobutyl group, a sec-butyl group, a tert-butyl group, a phenyl group, a biphenyl group, a terphenyl group, and a naphthyl group, b51 may be selected from 1, 2, 3, 4, and 5, b52 may be selected from 1, 2, 3, 4, 5, 6, and 7, b53 may be selected from 1, 2, 3, 4, 5, 6, 7, 8, and 9, b54 may be selected from 1, 2, 3, and 4, and

* indicates a binding site to a neighboring atom.

In one embodiment, in Formulae 1-1 to 1-8, $Y_{11}$ to $Y_{13}$ may each independently be selected from groups represented by Formulae 6-1 to 6-39, but embodiments of the present disclosure are not limited thereto:

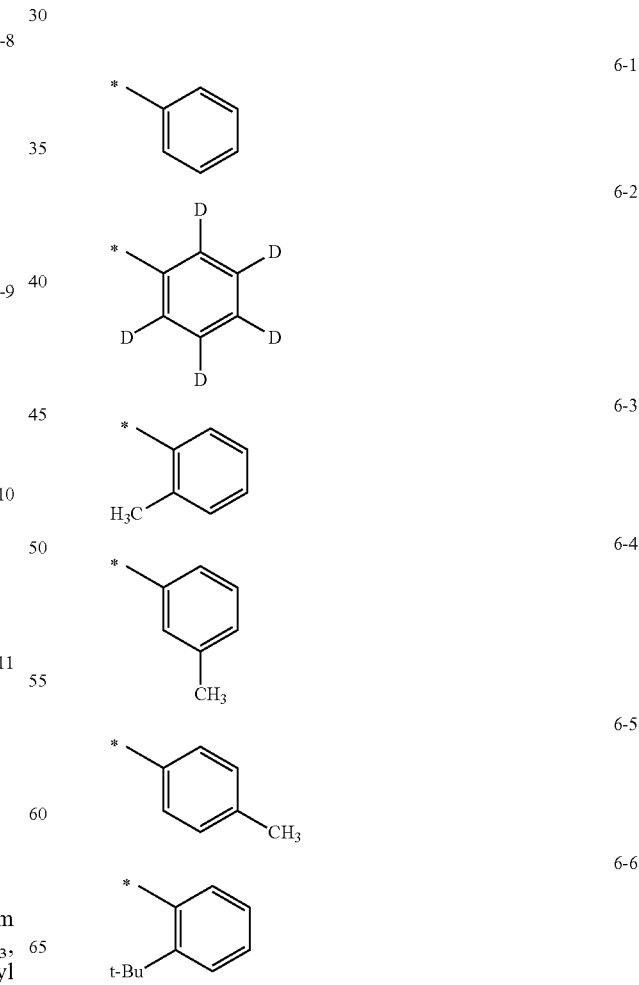

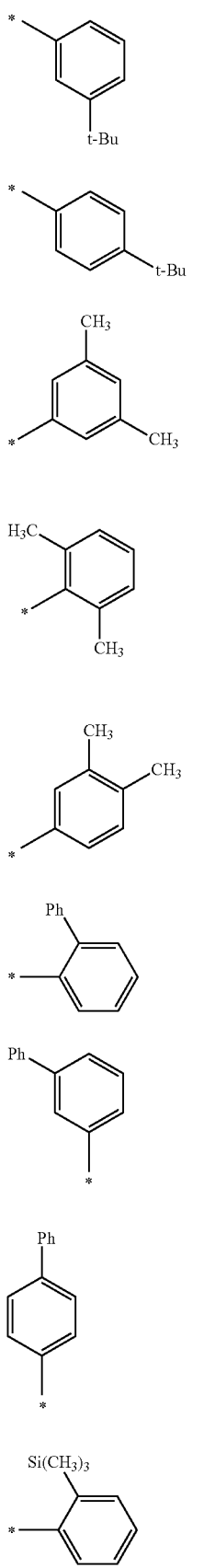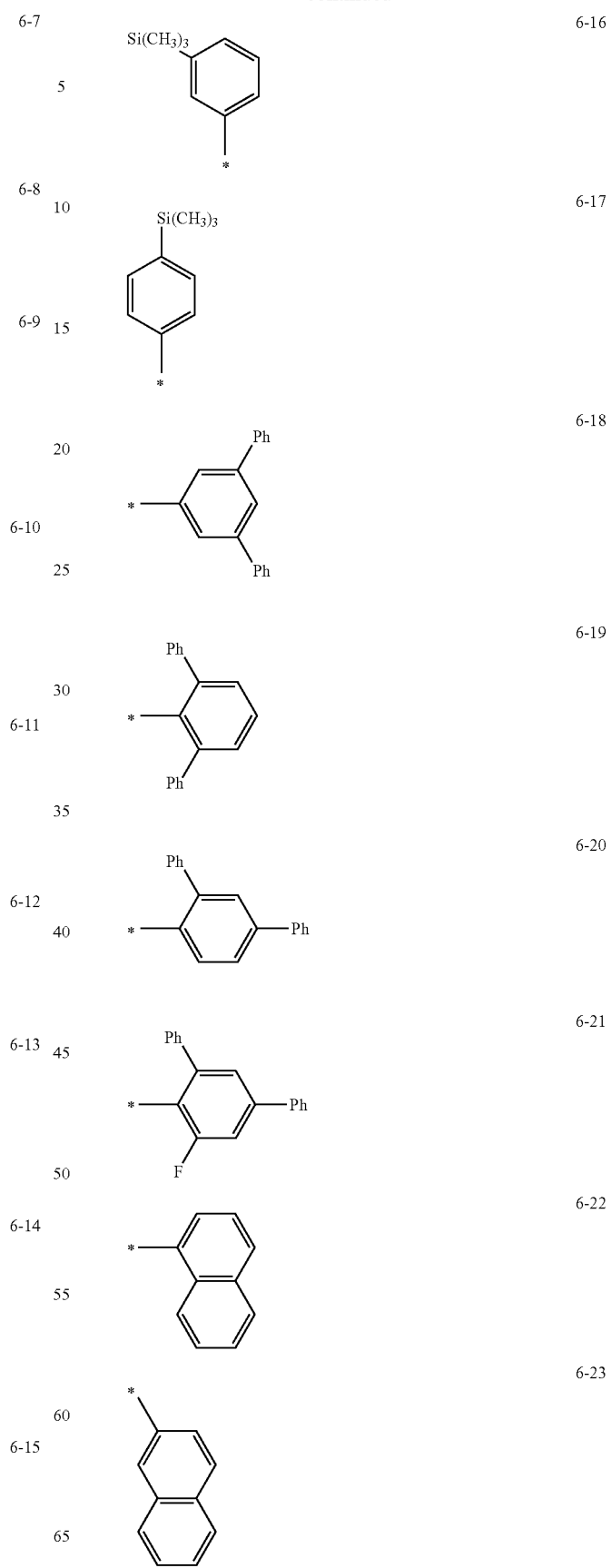

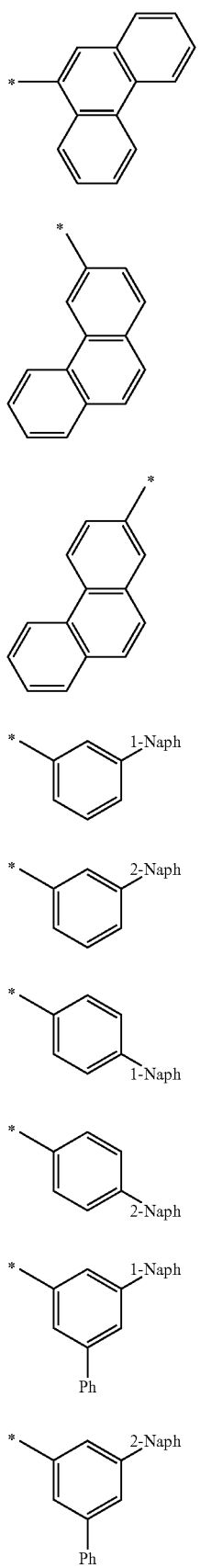

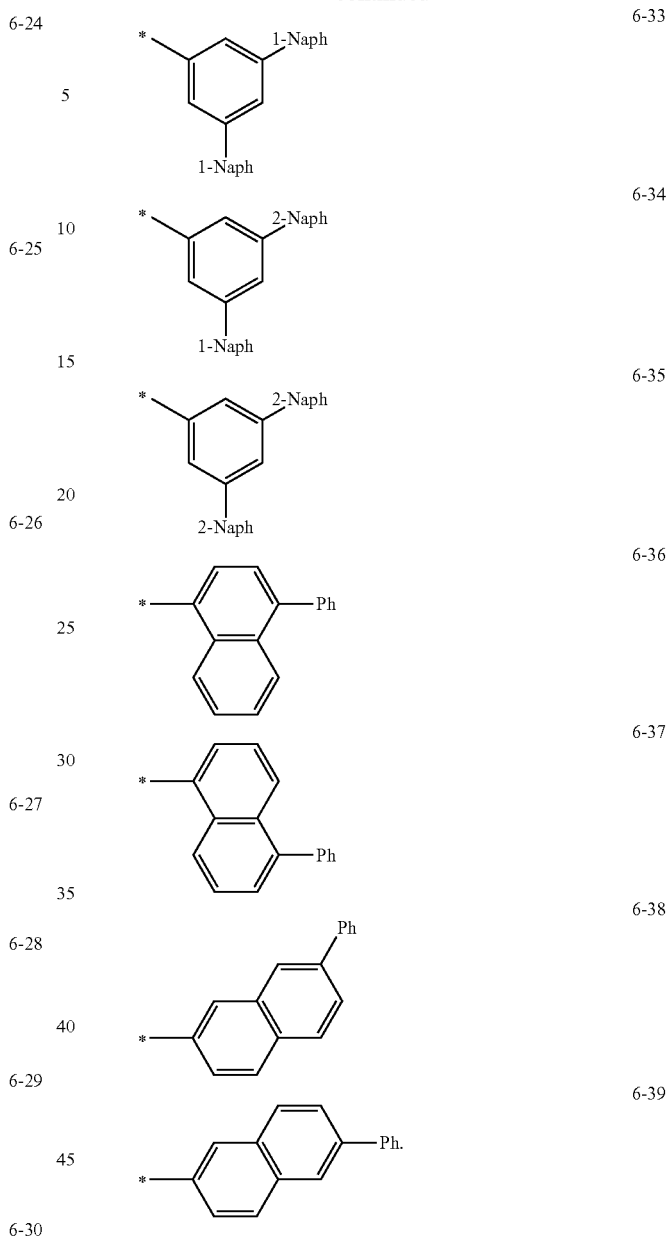

In Formulae 6-1 to 6-39,
t-Bu may be a tert-butyl group,
Ph may be a phenyl group,
1-Naph may be a 1-naphthyl group,
2-Naph may be a 2-naphthyl group, and
* indicates a binding site to a neighboring atom.

In Formulae 1-1 to 1-8, $L_{11}$ to $L_{14}$ may each independently be selected from:

a single bond, a $C_6$-$C_{60}$ arylene group, a $C_1$-$C_{60}$ heteroarylene group, a biphenylene group, and a terphenylene group; and a $C_6$-$C_{60}$ arylene group, a $C_1$-$C_{60}$ heteroarylene group, a biphenylene group, and a terphenylene group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group and —Si($Q_1$)($Q_2$)($Q_3$), and $Q_1$ to $Q_3$ may each independently be selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group.

For example, in Formulae 1-1 to 1-8, $L_{11}$ to $L_{14}$ may each independently be selected from:

a single bond, a phenylene group, a naphthylene group, a phenanthrenylene group, an anthracenylene group, a triphenylenylene group, a pyrenylene group, a chrysenylenylene group, a thiophenylene group, a furanylene group, a biphenylene group, and a terphenylene group; and a phenylene group, a naphthylene group, a phenanthrenylene group, an anthracenylene group, a triphenylenylene group, a pyrenylene group, a chrysenylenylene group, a thiophenylene group, a furanylene group, a biphenylene group, and a terphenylene group, each substituted with at least one selected from deuterium, —F, —Cl, —Br, —I, a cyano group, —$CD_3$, —$CD_2H$, —$CDH_2$, —$CF_3$, —$CF_2H$, —$CFH_2$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, a butoxy group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, a phenanthrolinyl group, and —Si($Q_1$)($Q_2$)($Q_3$), and $Q_1$ to $Q_3$ may each independently be selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, a terphenyl group, and a naphthyl group, but embodiments of the present disclosure are not limited thereto.

In one embodiment, in Formulae 1-1 to 1-8, $L_{11}$ to $L_{14}$ may each independently be selected from:

a single bond, a phenylene group, a naphthylene group, a biphenylene group, and a terphenylene group; and a phenylene group, a naphthylene group, a biphenylene group, and a terphenylene group, each substituted with at least one selected from deuterium, —F, —Cl, —Br, —I, a cyano group, —$CD_3$, —$CD_2H$, —$CDH_2$, —$CF_3$, —$CF_2H$, —$CFH_2$, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, a furanyl group, and —Si($Q_1$)($Q_2$)($Q_3$), $Q_1$ to $Q_3$ may each independently be selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$; and an n-propyl group, an isopropyl group, an n-butyl group, an isobutyl group, a sec-butyl group, a tert-butyl group, a phenyl group, a biphenyl group, a terphenyl group, and a naphthyl group, but embodiments of the present disclosure are not limited thereto.

In one embodiment, in Formulae 1-1 to 1-8, $L_{11}$ to $L_{14}$ may each independently be selected from groups represented by Formulae 3-1 to 3-12, but embodiments of the present disclosure are not limited thereto:

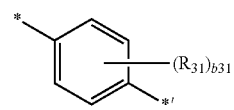

3-1

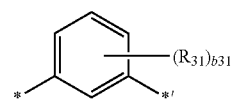

3-2

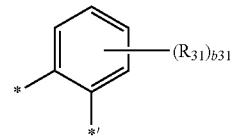

3-3

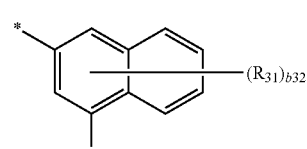

3-4

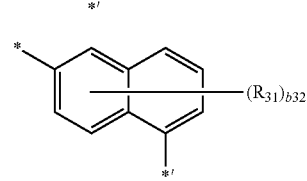

3-5

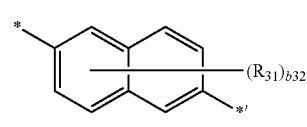

3-6

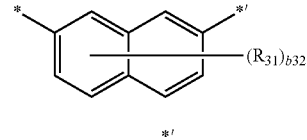

3-7

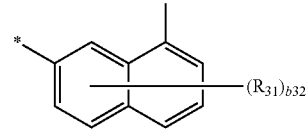

3-8

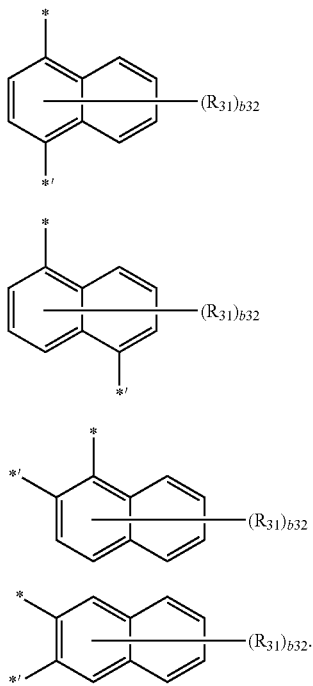

3-9

3-10

3-11

3-12

In Formulae 3-1 to 3-12, $R_{31}$ may be selected from hydrogen, deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, a furanyl group, and —Si(Q$_1$)(Q$_2$)(Q$_3$), $Q_1$ to $Q_3$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an isopropyl group, an n-butyl group, an isobutyl group, a sec-butyl group, a tert-butyl group, a phenyl group, a biphenyl group, a terphenyl group, and a naphthyl group, b31 may be selected from 1, 2, 3, and 4, b32 may be selected from 1, 2, 3, 4, 5, and 6, and

* and *' each indicate a binding site to a neighboring atom.

In Formulae 1-1 to 1-8, a11 to a14 each indicate the number of repetitions of $L_{11}$ to $L_{14}$, respectively, and may each independently be selected from 0, 1, 2, and 3. When a11 to a14 are two or more, a plurality of each of the $L_{11}(s)$ to $L_{14}(s)$ may be identical to or different from each other.

For example, in Formulae 1-1 to 1-8, a11 to a14 may each independently be selected from 0 and 1, but embodiments of the present disclosure are not limited thereto.

In Formulae 1-1 to 1-8, 2-1, and 2-2, $R_{11}$, $R_{12}$, and $R_{21}$ to $R_{24}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si(Q$_1$)(Q$_2$)(Q$_3$), and $Q_1$ to $Q_3$ may each independently be selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group.

For example, in Formulae 1-1 to 1-8, 2-1, and 2-2, $R_{11}$, $R_{12}$, and $R_{21}$ to $R_{24}$ may each independently be selected from hydrogen, deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, a butoxy group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group, but embodiments of the present disclosure are not limited thereto.

In one embodiment, in Formulae 1-1 to 1-8, 2-1, and 2-2, $R_{11}$, $R_{12}$, and $R_{21}$ to $R_{24}$ may each independently be selected from hydrogen, deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, a phenyl group, a biphenyl group, a terphenyl group, and a naphthyl group, but embodiments of the present disclosure are not limited thereto.

In Formulae 1-1 to 1-8, b11 indicates the number of $R_{11}(s)$, b11 may be selected from 1, 2, 3, 4, 5, and 6. When b11 is two or more, two or more $R_{11}(s)$ may be identical to or different from each other.

In Formulae 1-1 to 1-8, b12 indicates the number of $R_{12}(s)$, and b12 may be selected from 1, 2, 3, and 4. When b12 is two or more, two or more $R_{12}(s)$ may be identical to or different from each other.

In Formulae 2-1 and 2-2, b21 to b24 respectively indicate the number of $R_{21}(s)$ to $R_{24}(s)$, and b21 to b24 may each independently be selected from 1, 2, 3, 4, 5, 6, 7, 8, 9, and 10. When b21 to b24 are two or more, two or more $R_{21}(s)$ to $R_{24}(s)$ may be identical to or different from each other.

In one embodiment, in Formulae 1-1 to 1-8, $X_{11}$ to $X_{14}$ may be different from each other, and $X_{11}$ to $X_{14}$ may each independently be selected from groups represented by Formulae 2-101 to 2-116 and 2-201 to 2-216, but embodiments of the present disclosure are not limited thereto:

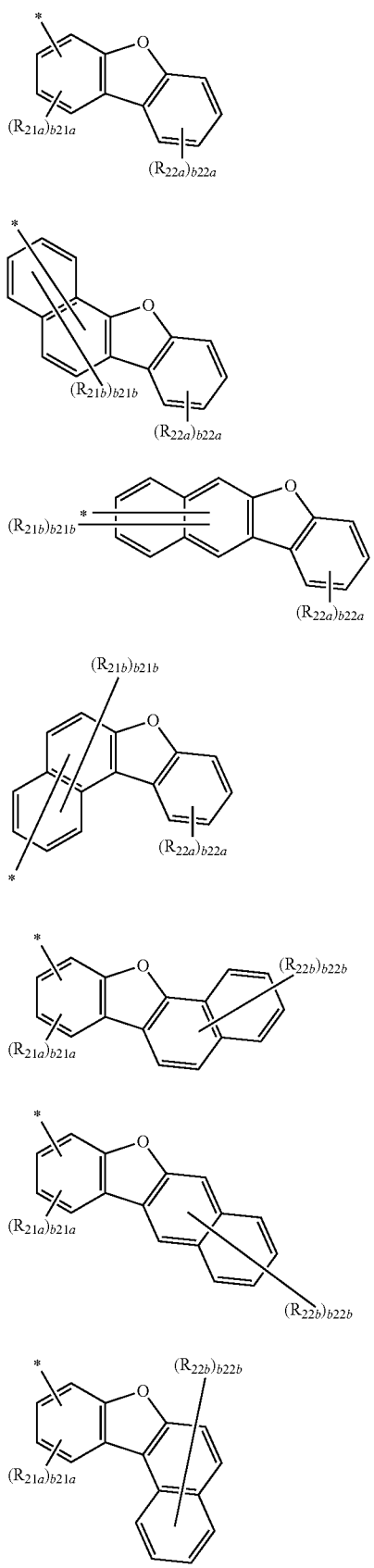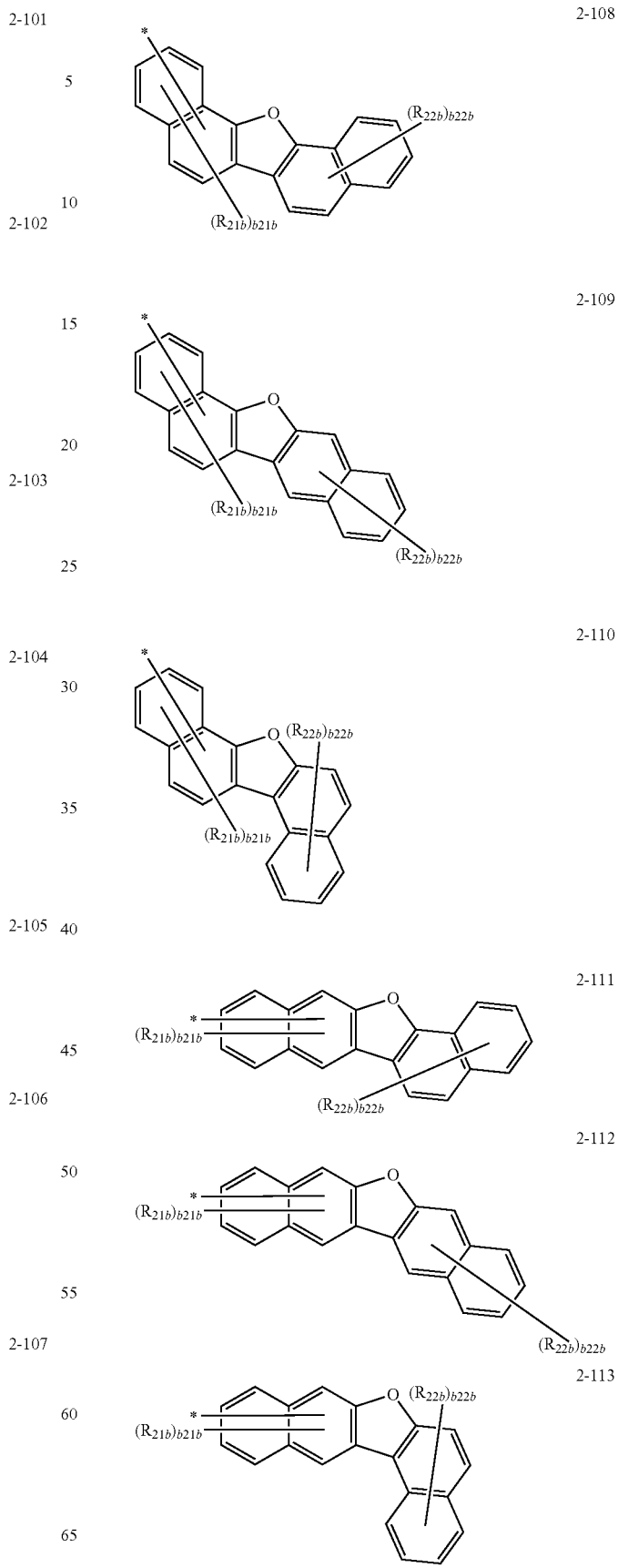

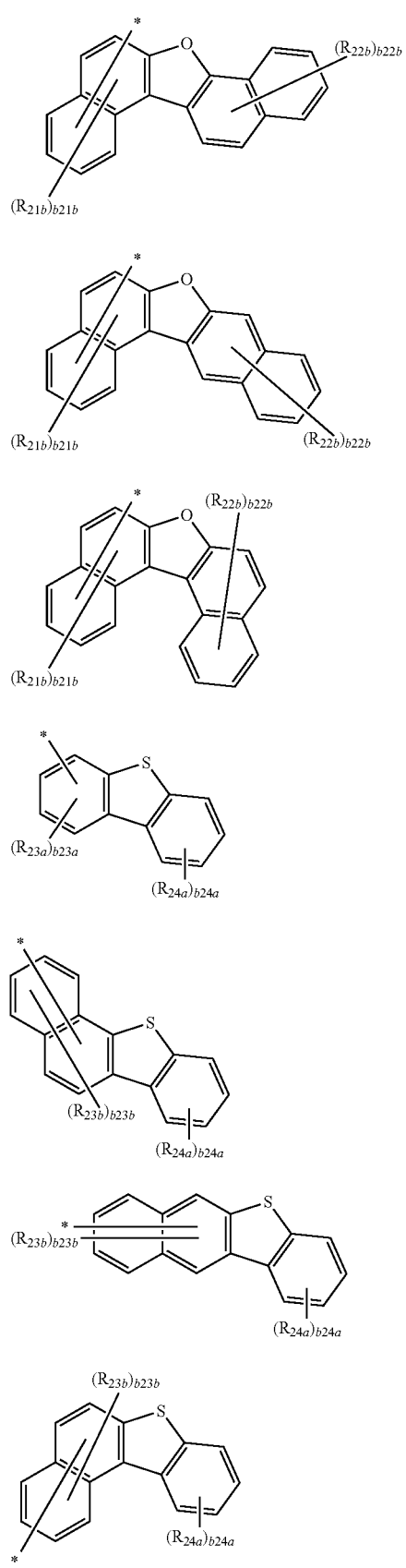
2-114
2-115
2-116
2-201
2-202
2-203
2-204
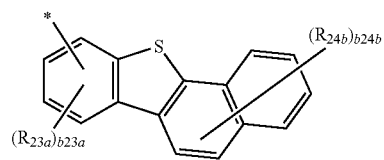
2-205
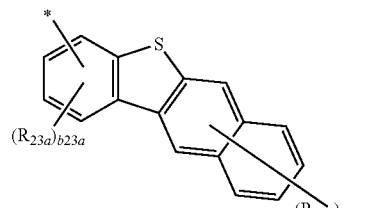
2-206
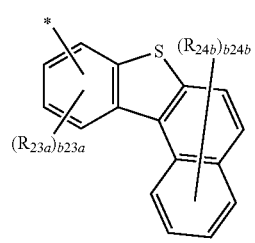
2-207
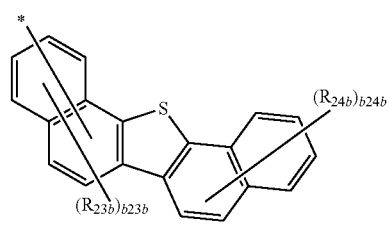
2-208
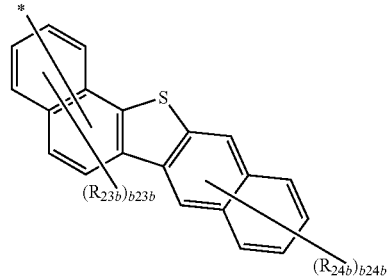
2-209
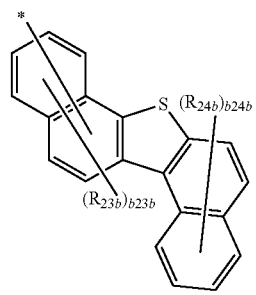
2-210
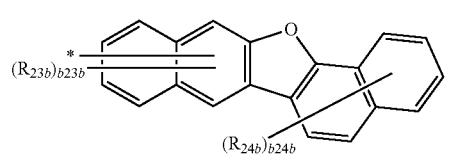
2-211

-continued

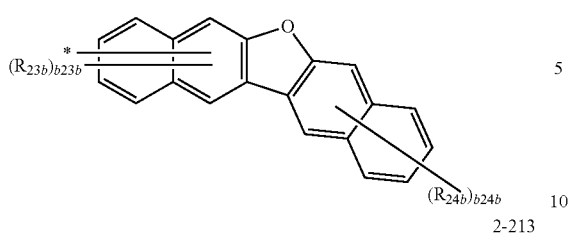
2-212

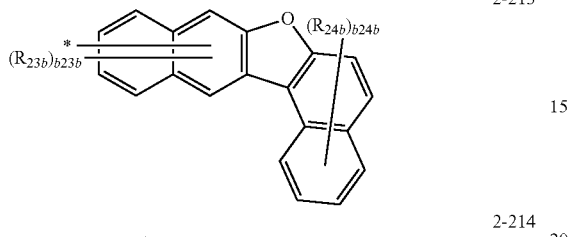
2-213

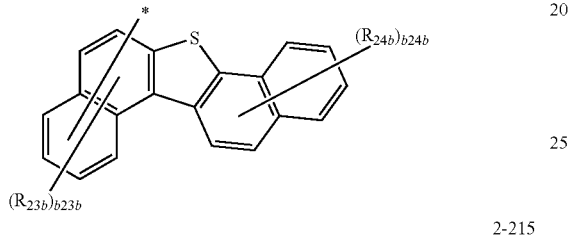
2-214

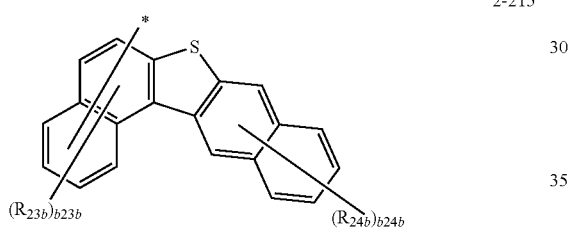
2-215

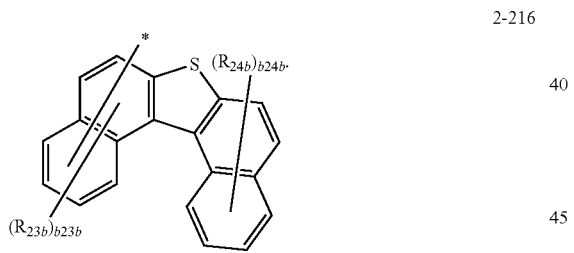
2-216

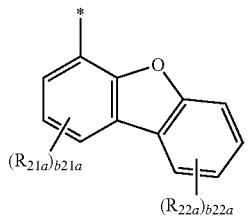
2-101A

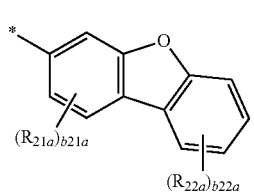
2-101B

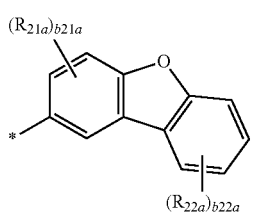
2-101C

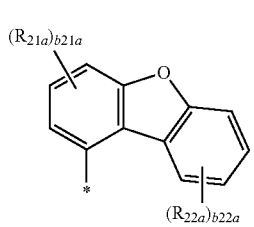
2-101D

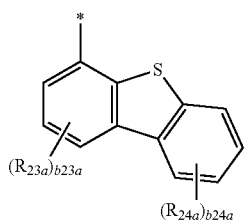
2-201A

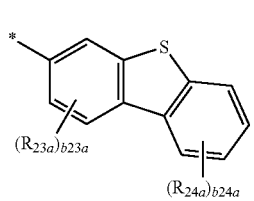
2-201B

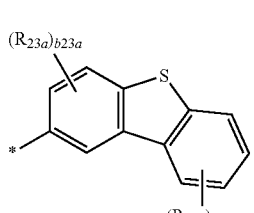
2-201C

In Formulae 2-101 to 2-116 and 2-201 to 2-216, $R_{21a}$, $R_{21b}$, $R_{22a}$, $R_{22b}$, $R_{23a}$, $R_{23b}$, $R_{24a}$, and $R_{24b}$ may each independently be the same as described in connection with $R_{21}$ to $R_{24}$ in Formulae 2-1 and 2-2, b21a and b23a may each independently be selected from 1, 2, and 3, b21b and b23b may each independently be selected from 1, 2, 3, 4, and 5, b22a and b24a may each independently be selected from 1, 2, 3, and 4, b22b and b24b may each independently be selected from 1, 2, 3, 4, 5, and 6, and

* indicates a binding site to a neighboring atom.

In one or more embodiments, in Formulae 1-1 to 1-8, $X_{11}$ to $X_{14}$ may be different from each other, and $X_{11}$ to $X_{14}$ may each independently be selected from groups represented by Formulae 2-101A to 2-101D and 2-201A to 2-201D, but embodiments of the present disclosure are not limited thereto:

-continued 2-201D

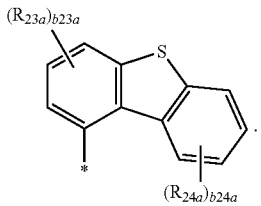

In Formulae 2-101A to 2-101D and 2-201A to 2-201D, $R_{21a}$, $R_{22a}$, $R_{23a}$, and $R_{24a}$ may each independently be the same as described in connection with $R_{21}$ to $R_{24}$ in Formulae 2-1 and 2-2, b21a and b23a may each independently be selected from 1, 2, and 3, b22a and b24a may each independently be selected from 1, 2, 3, and 4, and \* indicates a binding site to a neighboring atom.

In one or more embodiments, in Formulae 1-3 to 1-5, $X_{11}$ may be represented by Formula 2-101A, and $X_{12}$ may be represented by one selected from Formulae 2-101B to 2-101D and 2-201A to 2-201D;

$X_{11}$ may be represented by Formula 2-101B, and $X_{12}$ may be represented by one selected from Formulae 2-101A, 2-101C, 2-101D, and 2-201A to 2-201D;

$X_{11}$ may be represented by Formula 2-101C, and $X_{12}$ may be represented by one selected from Formulae 2-101A, 2-101B, 2-101D, and 2-201A to 2-201D;

$X_{11}$ may be represented by Formula 2-101D, and $X_{12}$ may be represented by one selected from Formulae 2-101A to 2-101C and 2-201A to 2-201D;

$X_{11}$ may be represented by Formula 2-201A, and $X_{12}$ may be represented by one selected from Formulae 2-101A to 2-101D and 2-201B to 2-201D;

$X_{11}$ may be represented by Formula 2-201B, and $X_{12}$ may be represented by one selected from Formulae 2-101A to 2-101D, 2-201A, 2-201C, and 2-201D;

$X_{11}$ may be represented by Formula 2-201C, and $X_{12}$ may be represented by one selected from Formulae 2-101A to 2-101D, 2-201A, 2-201B, and 2-201D; or $X_{11}$ may be represented by Formula 2-201D, and $X_{12}$ may be represented by one selected from Formulae 2-101A to 2-101D and 2-201A to 2-201C, but embodiments of the present disclosure are not limited thereto.

In one or more embodiments, in Formulae 1-3 to 1-5, $X_{11}$ may be represented by Formula 2-101A, and $X_{12}$ may be represented by one selected from Formulae 2-101B to 2-101D and 2-201B to 2-201D;

$X_{11}$ may be represented by Formula 2-101B, and $X_{12}$ may be represented by one selected from Formulae 2-101A, 2-101C, 2-101D, 2-201A, 2-201C, and 2-201D;

$X_{11}$ may be represented by Formula 2-101C, and $X_{12}$ may be represented by one selected from Formulae 2-101A, 2-101B, 2-101D, 2-201A, 2-201B, and 2-201D;

$X_{11}$ may be represented by Formula 2-101D, and $X_{12}$ may be represented by one selected from Formulae 2-101A to 2-101C and 2-201A to 2-201C;

$X_{11}$ may be represented by Formula 2-201A, and $X_{12}$ may be represented by one selected from Formulae 2-101B to 2-101D and 2-201B to 2-201D;

$X_{11}$ may be represented by Formula 2-201B, and $X_{12}$ may be represented by one selected from Formulae 2-101A, 2-101C, 2-101D, 2-201A, 2-201C, and 2-201D;

$X_{11}$ may be represented by Formula 2-201C, and $X_{12}$ may be represented by one selected from Formulae 2-101A, 2-101B, 2-101D, 2-201A, 2-201B, and 2-201D; or $X_{11}$ may be represented by Formula 2-201D, and $X_{12}$ may be represented by one selected from Formulae 2-101A to 2-101C and 2-201A to 2-201C, but embodiments of the present disclosure are not limited thereto.

In one embodiment, the diamine compound may be represented by one selected from Formulae 1-1 to 1-5, but embodiments of the present disclosure are not limited thereto.

In one or more embodiments, the diamine compound may be represented by one selected from Formulae 1-11 to 1-15, but embodiments of the present disclosure are not limited thereto:

1-11

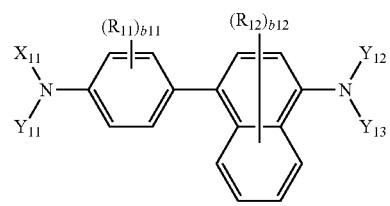

1-12

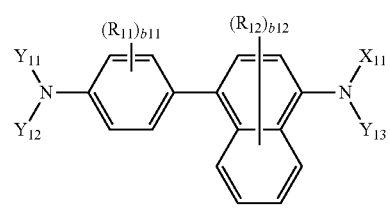

1-13

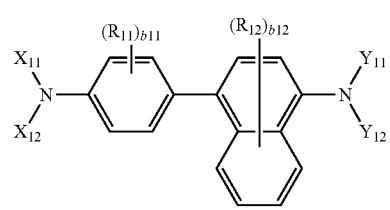

1-14

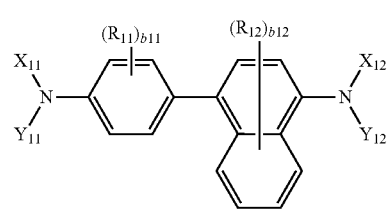

1-15

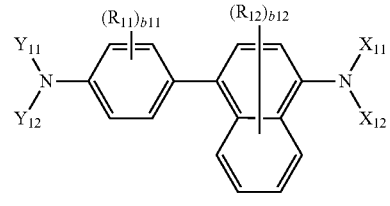

-continued 2-101A

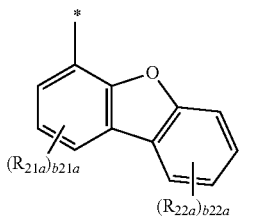

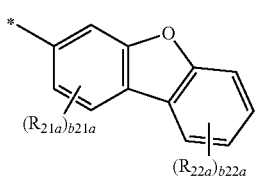

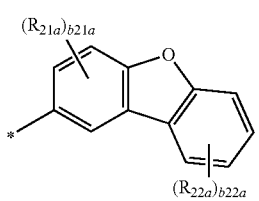

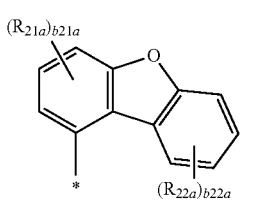

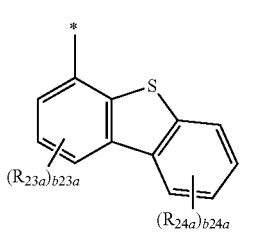

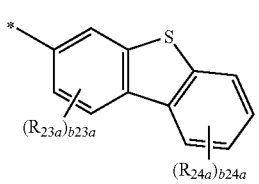

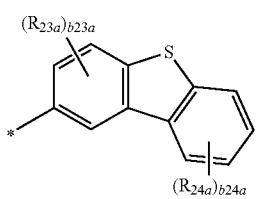

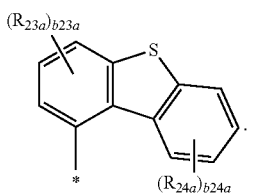

In Formulae 1-11 to 1-15, 2-101A to 2-101D, and 2-201A to 2-201D, in Formulae 1-1 and 1-2, $X_{11}$ may be represented by one selected from Formulae 2-101A to 2-101D and 2-201A to 2-201D, in Formulae 1-3 to 1-5, $X_{11}$ may be represented by Formula 2-101A, and $X_{12}$ may be represented by one selected from Formulae 2-101B to 2-101D and 2-201A to 2-201D;

$X_{11}$ may be represented by Formula 2-101B, and $X_{12}$ may be represented by one selected from Formulae 2-101A, 2-101C, 2-101D, and 2-201A to 2-201D;

$X_{11}$ may be represented by Formula 2-101C, and $X_{12}$ may be represented by one selected from Formulae 2-101A, 2-101B, 2-101D, and 2-201A to 2-201D;

$X_{11}$ may be represented by Formula 2-101D, and $X_{12}$ may be represented by one selected from Formulae 2-101A to 2-101C and 2-201A to 2-201D;

$X_{11}$ may be represented by Formula 2-201A, and $X_{12}$ may be represented by one selected from Formulae 2-101A to 2-101D and 2-201B to 2-201D;

$X_{11}$ may be represented by Formula 2-201B, and $X_{12}$ may be represented by one selected from Formulae 2-101A to 2-101D, 2-201A, 2-201C, and 2-201D;

$X_{11}$ may be represented by Formula 2-201C, and $X_{12}$ may be represented by one selected from Formulae 2-101A to 2-101D, 2-201A, 2-201B, and 2-201D; or $X_{11}$ may be represented by Formula 2-201D, and $X_{12}$ may be represented by one selected from Formulae 2-101A to 2-101D and 2-201A to 2-201C, and $Y_{11}$ to $Y_{13}$, $R_{11}$, $R_{12}$, $R_{21}$ to $R_{24}$, b11, and b12 may each independently be the same as described in Formulae 1-1 to 1-8.

In one or more embodiments, the diamine compound may be selected from Compounds 1 to 68, but embodiments of the present disclosure are not limited thereto:

1

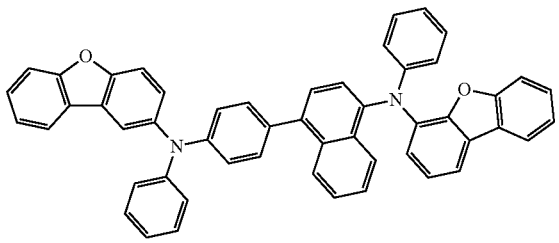

2

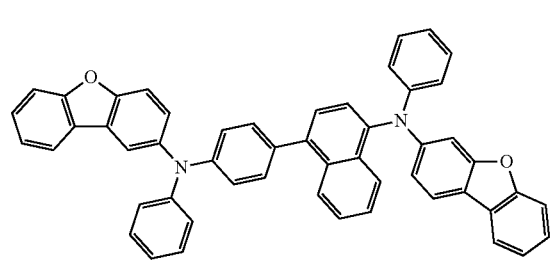

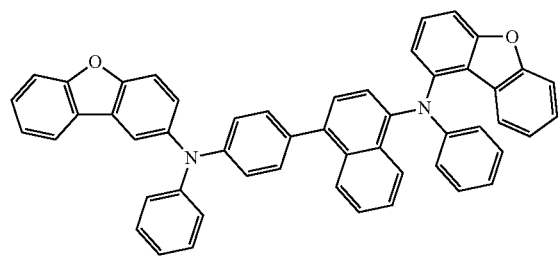
3
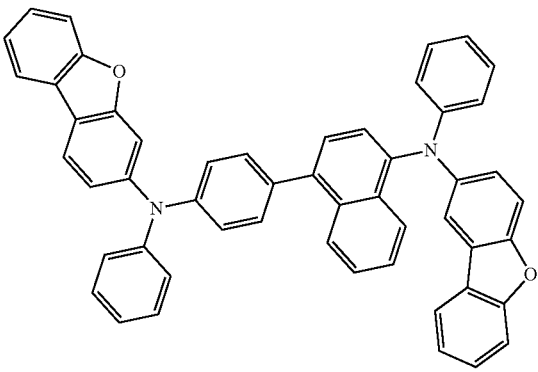
8
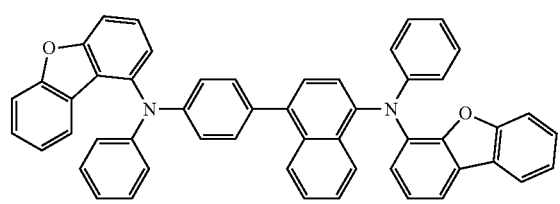
4
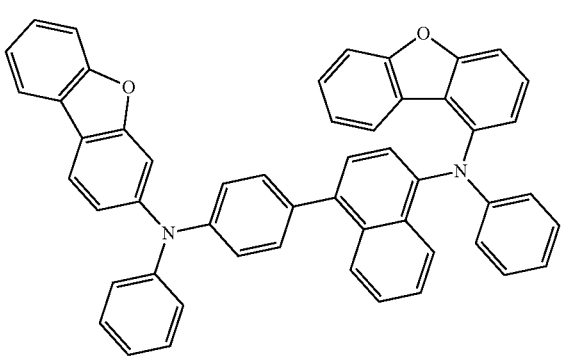
9
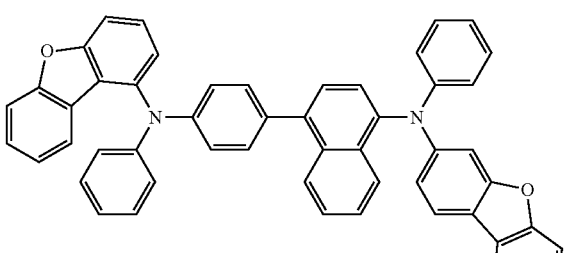
5
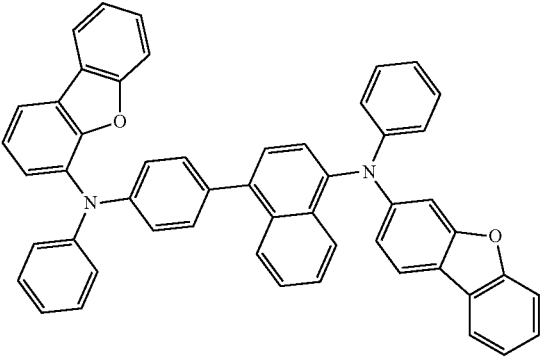
10
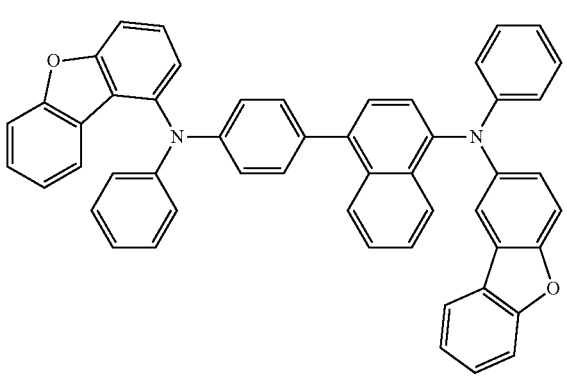
6
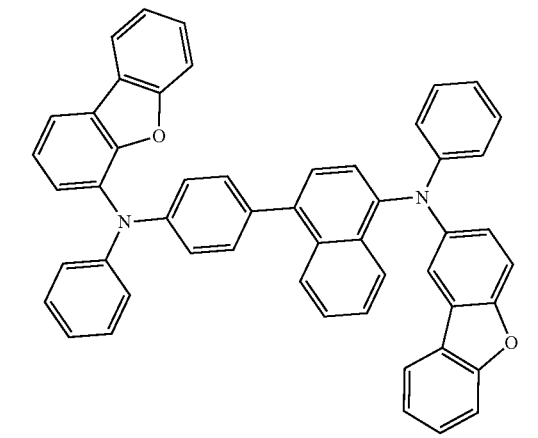
11
7

12
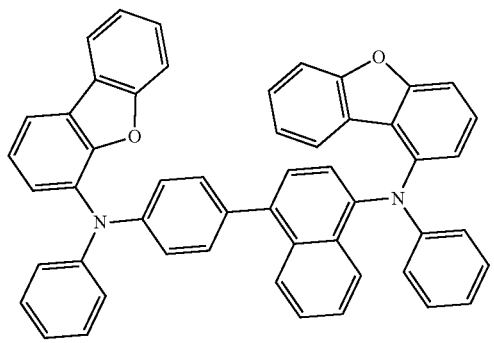
13
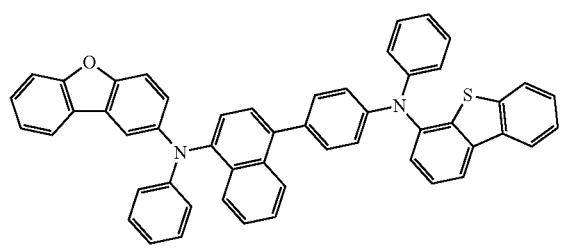
14
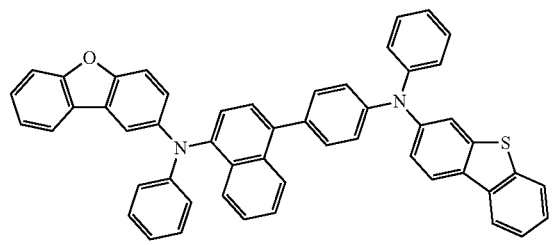
15
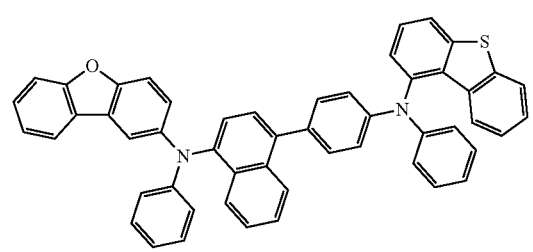
16
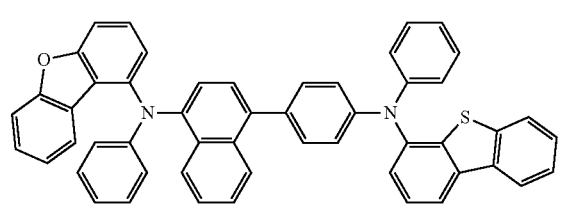
17
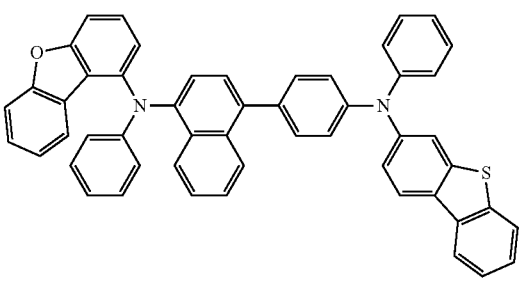
18
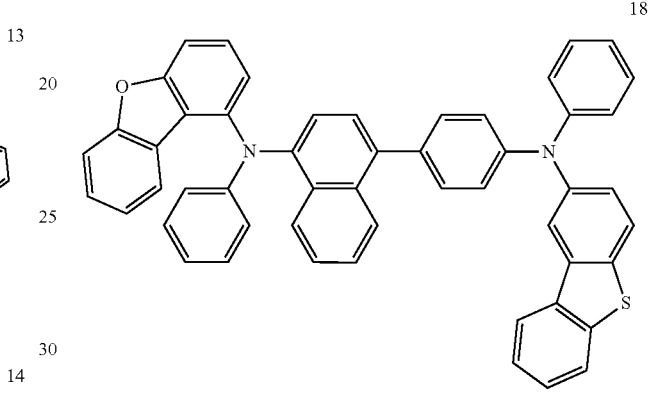
19
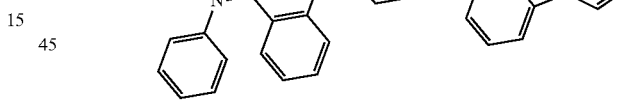
20
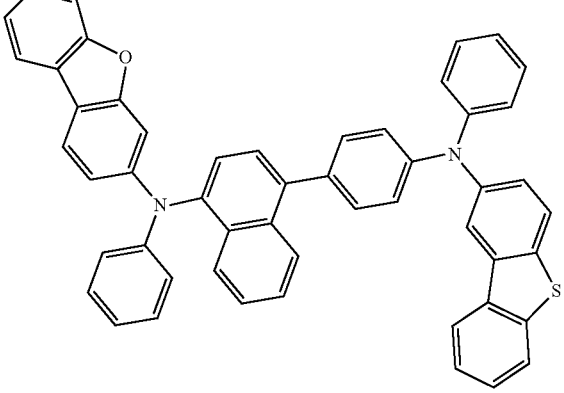

21
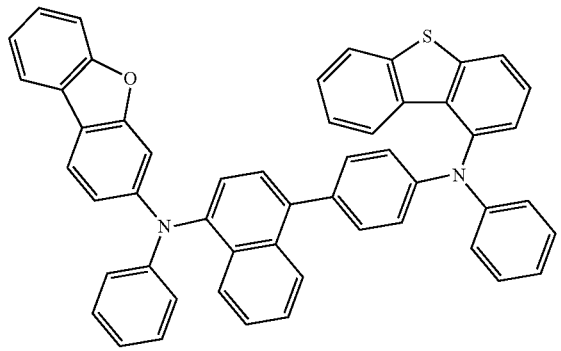
22
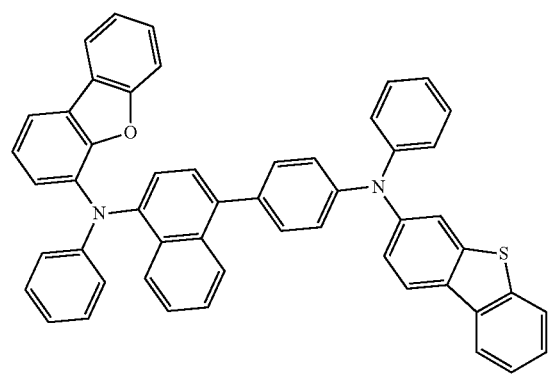
23
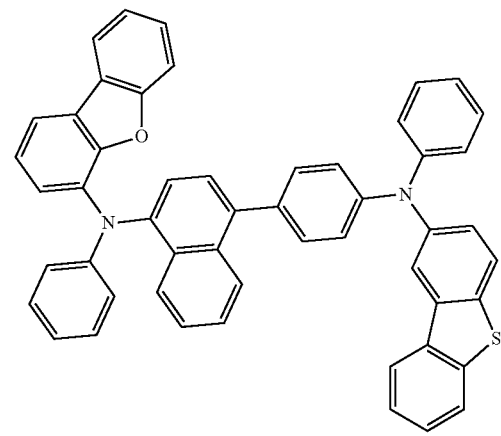
24
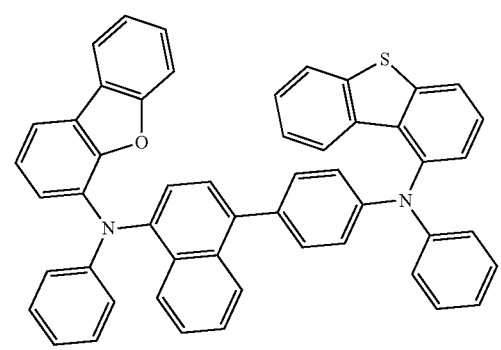
25
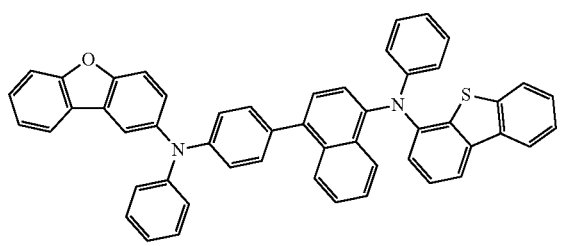
26
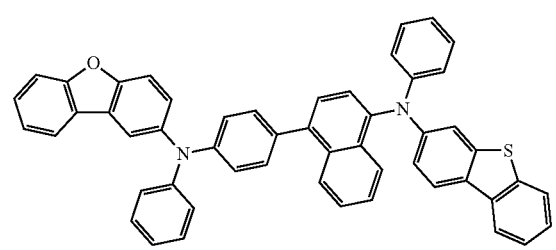
27
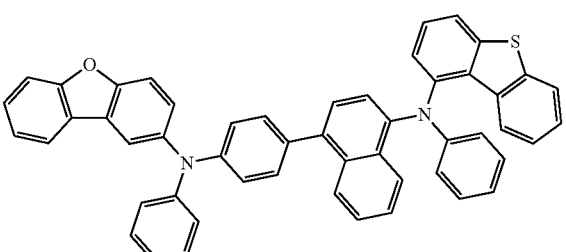
28
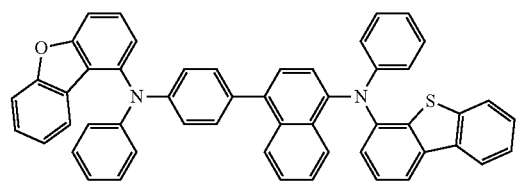
29
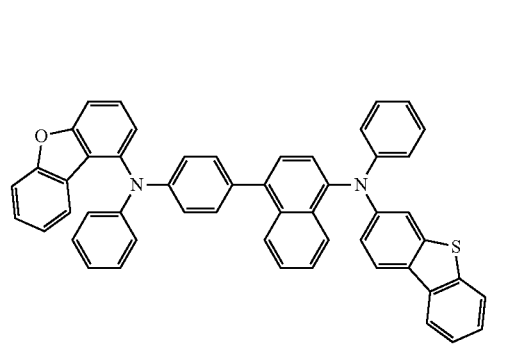

30
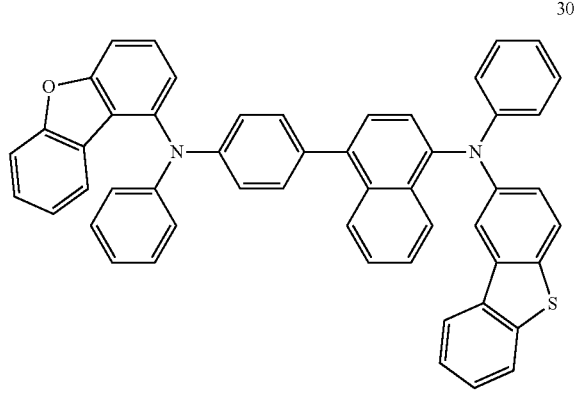
31
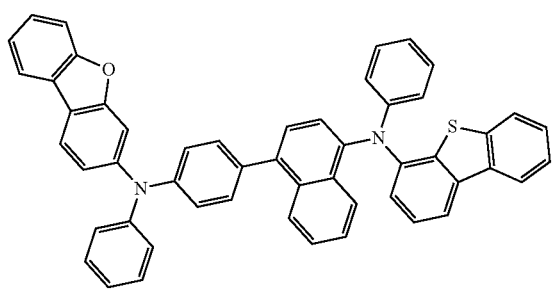
32
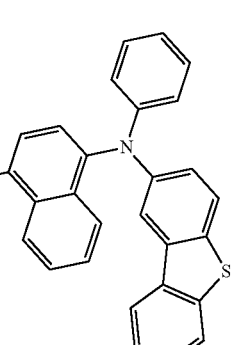
33
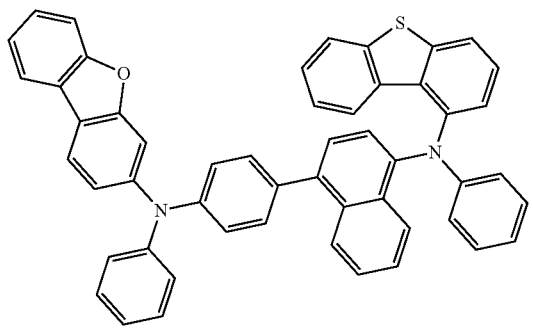
34
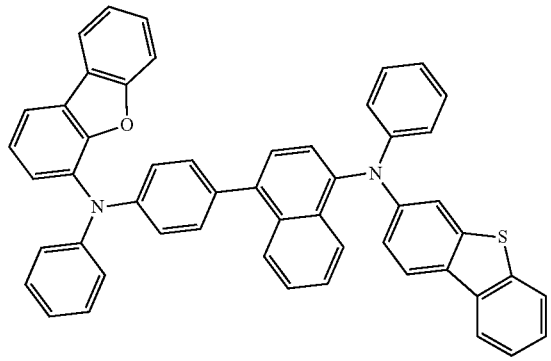
35
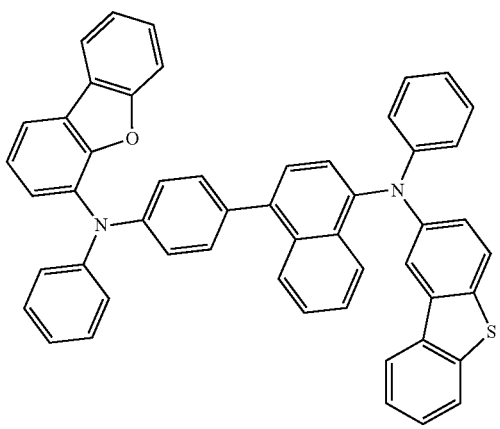
36
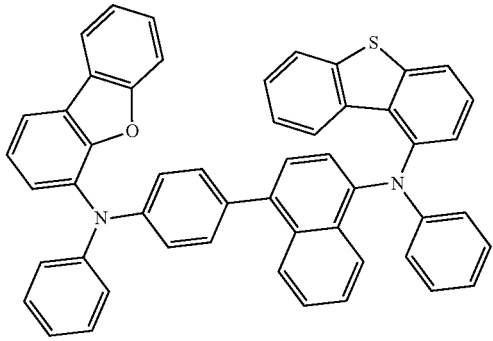
37
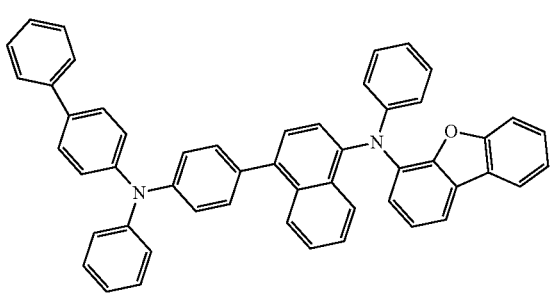

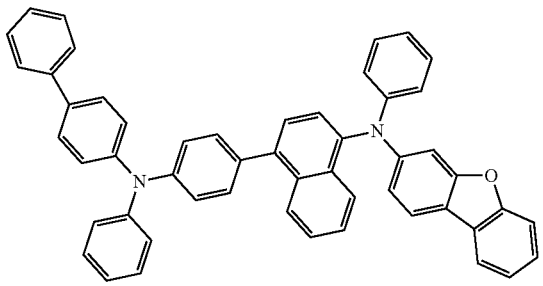
38
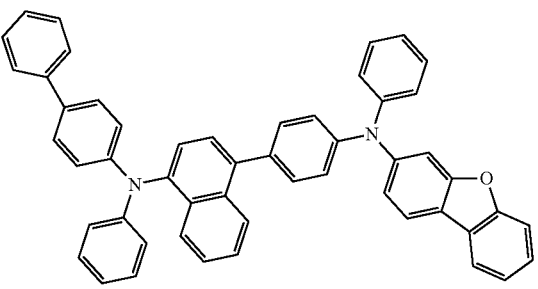
42
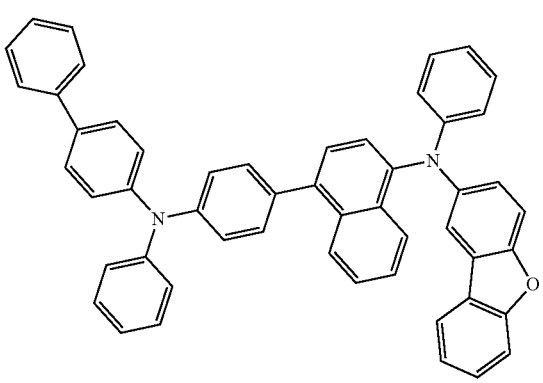
39
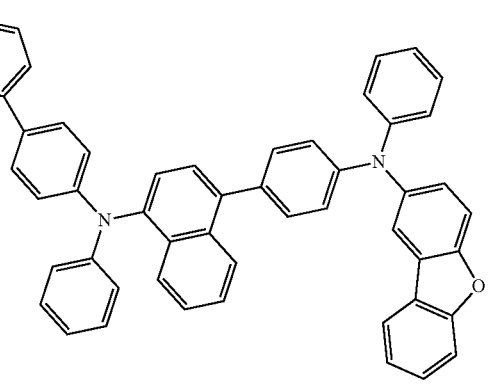
43
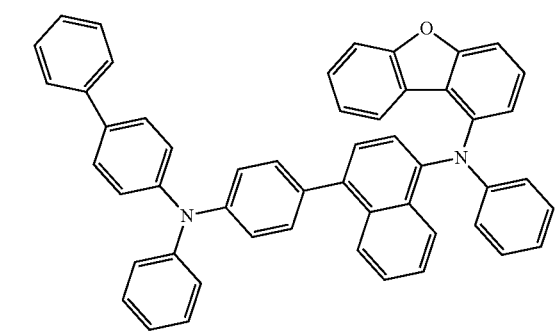
40
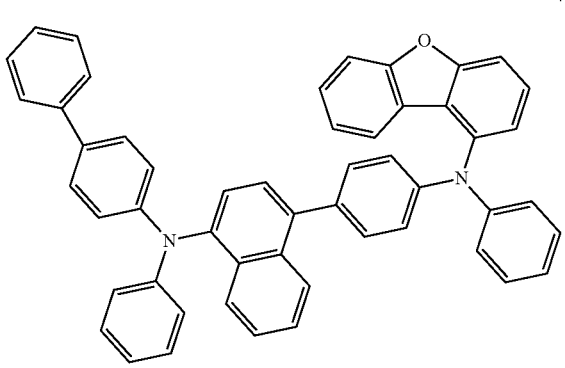
44
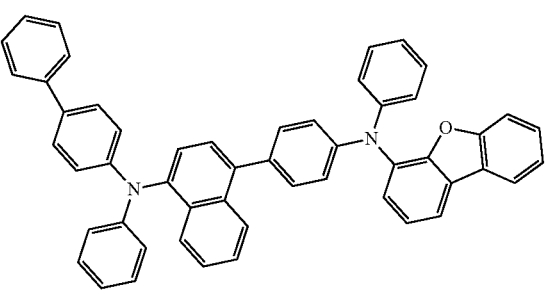
41
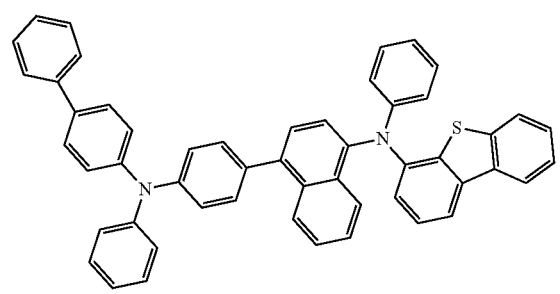
45

46
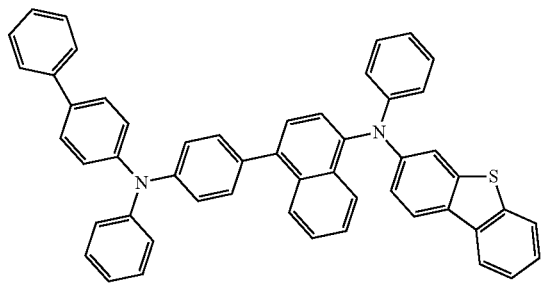
47
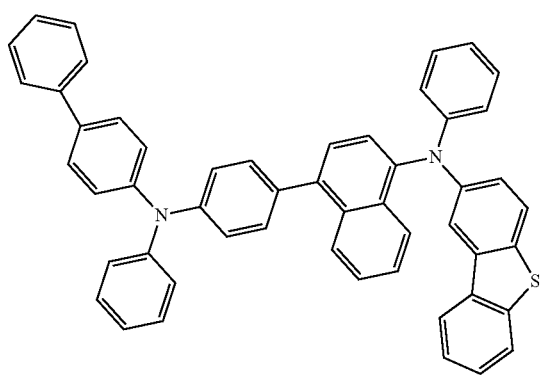
48
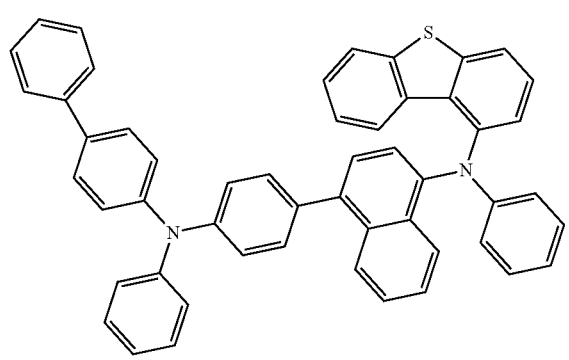
49
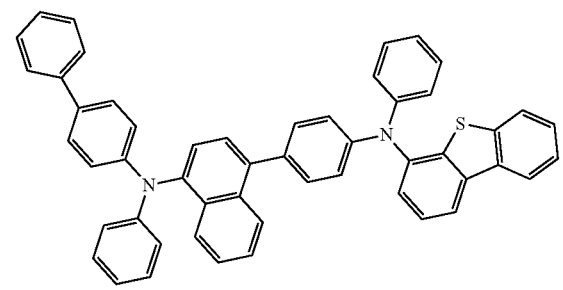
50
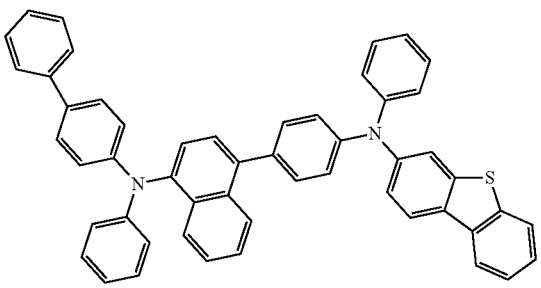
51
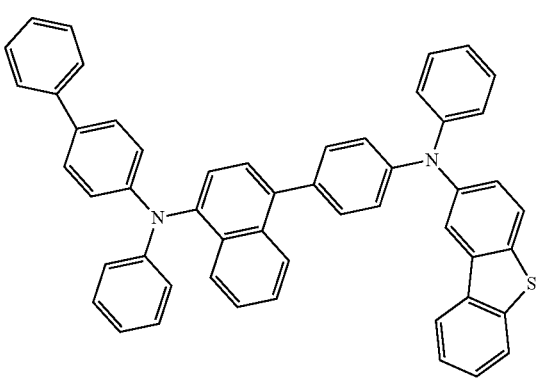
52
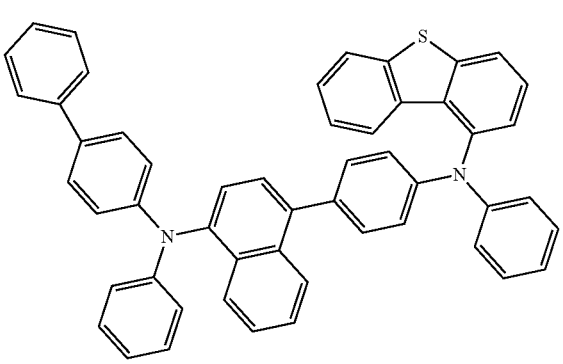
53
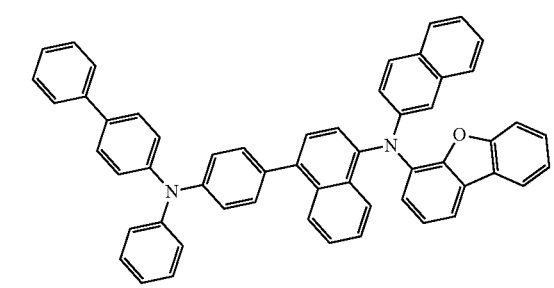

54
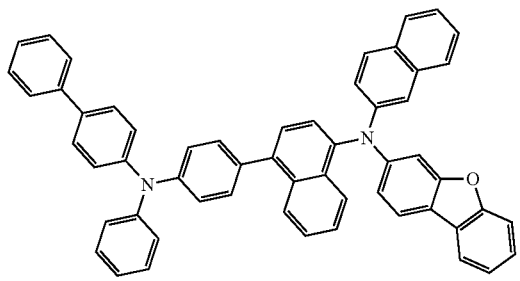
55
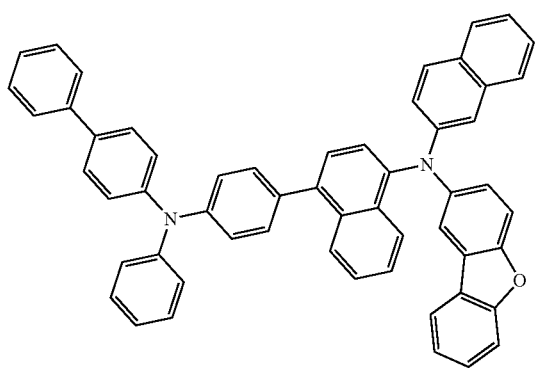
56
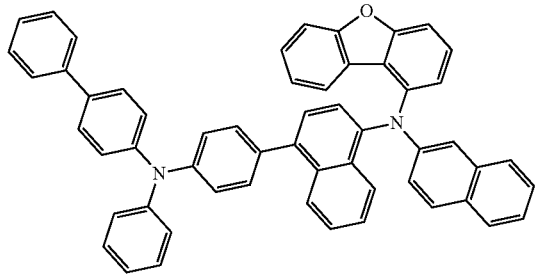
57
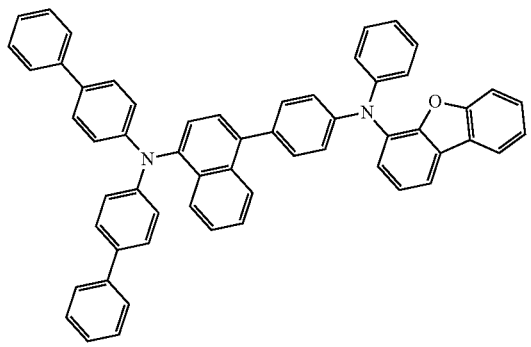
58
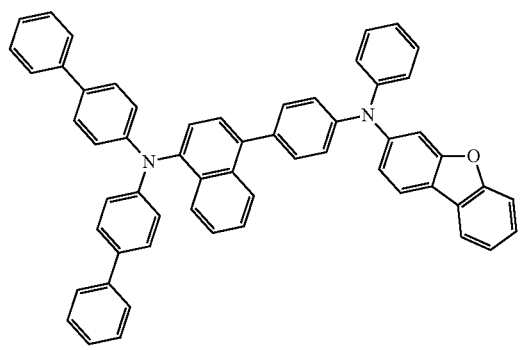
59
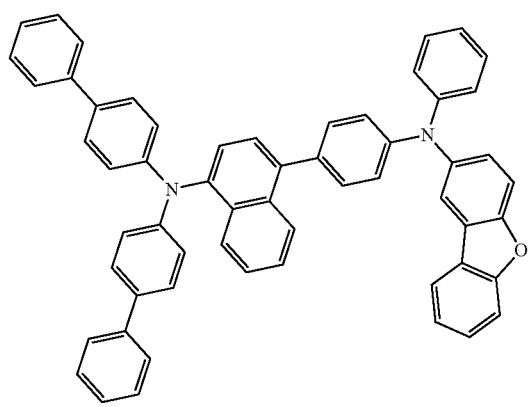
60
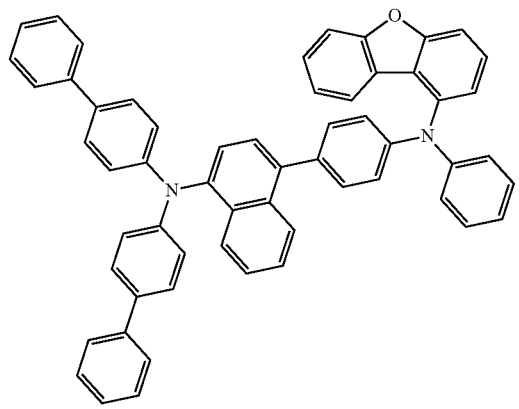
61
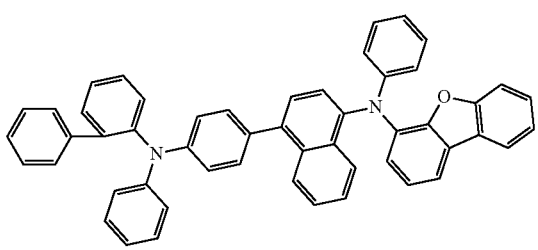

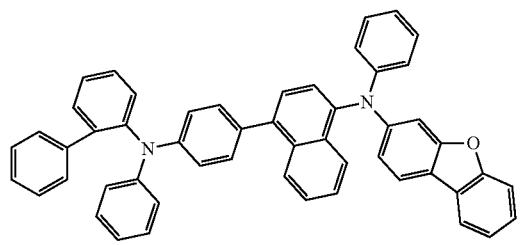
62

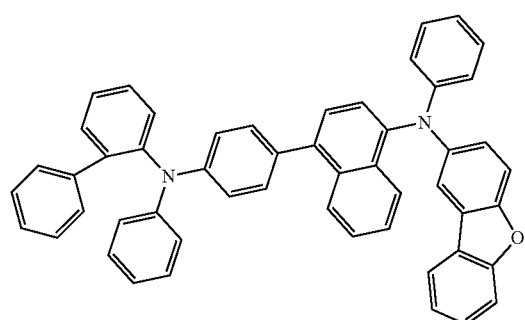
63

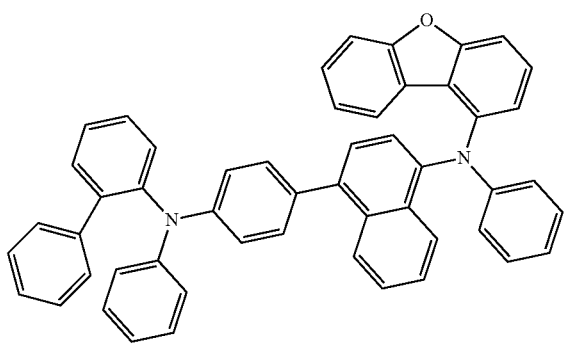
64

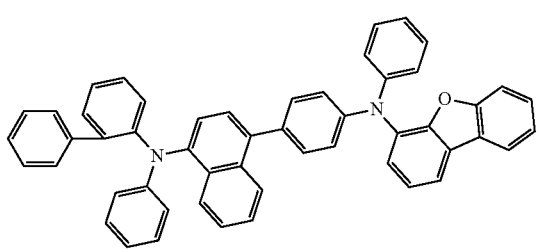
65

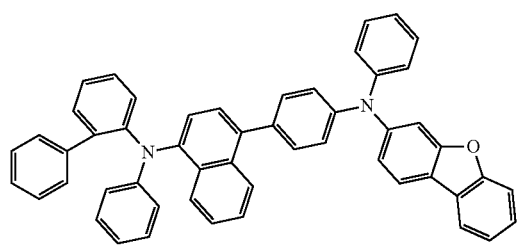
66

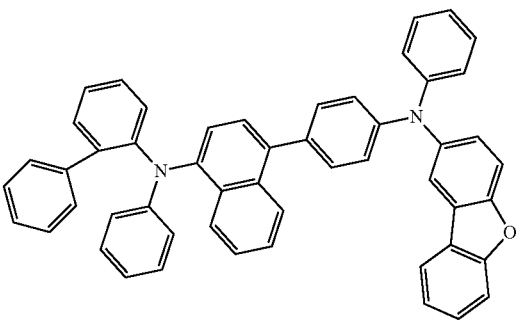
67

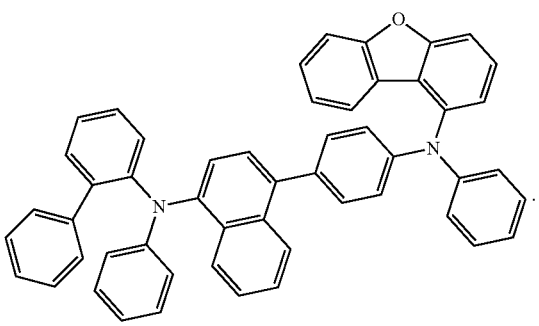
68

Since the diamine compound represented by one selected from Formulae 1-1 to 1-8 includes a naphthyl-phenyl linker, a plane formed by substituents of two amino groups may have a tilted structure, and the diamine compound may have a set (e.g., predetermined) dipole moment. Thus, when the diamine compound is deposited, the diamine compound tends to be densely laminated, thereby showing improved charge mobility. Therefore, an organic light-emitting device including the diamine compound represented by one selected from Formulae 1-1 to 1-8 may exhibit low driving voltage and high efficiency characteristics.

Since the diamine compound represented by one selected from Formulae 1-1 to 1-8 includes two or more dibenzofuran-based substituents and/or dibenzothiophene-based substituents having different structures, the glass transition temperature and/or the melting point of the diamine compound may be improved. Therefore, an organic light-emitting device including the diamine compound represented by Formula 1 may exhibit long lifespan characteristics, improved storage stability, and/or improved reliability.

The diamine compound represented by one selected from Formulae 1-1 to 1-8 may be synthesized by using any suitable organic synthesis methods available in the art. The synthesis method of the diamine compound may be recognized by those of skilled in the art by referring to Examples provided below.

The diamine compound represented by one selected from Formulae 1-1 to 1-8 may be used between a pair of electrodes of an organic light-emitting device.

As used herein, the expression "an (organic layer) includes at least one diamine compound" includes a case in which "an (organic layer) includes a diamine compound represented by one selected from Formulae 1-1 to 1-8 or a case in which an (organic layer) includes two or more different diamine compound represented by Formula 1".

For example, the organic layer may include, as the diamine compound, Compound 1 only. In this regard, Compound 1 may exist in a hole transport layer of the organic light-emitting device. In one embodiment, the organic layer may include, as the diamine compound, Compound 1 and Compound 2. In one or more embodiments, Compound 1 and Compound 2 may both exist in an identical layer (for example, Compound 1 and Compound 2 may both exist in a hole transport layer), or may exist in different layers (for example, Compound 1 may exist in a hole transport layer and Compound 2 may exist in a hole injection layer).

The organic layer includes i) a hole transport region that is between the first electrode (anode) and the emission layer and includes at least one of a hole injection layer, a hole transport layer, a buffer layer, and an electron blocking layer, and ii) an electron transport region that is between the emission layer and the second electrode (cathode) and includes at least one selected from a hole blocking layer, an electron transport layer, and an electron injection layer. For example, the hole transport region may include at least one of the diamine compounds represented by Formula 1.

The term "organic layer," as used herein, refers to a single layer and/or a plurality of layers between the first electrode and the second electrode of the organic light-emitting device. A material included in the "organic layer" is not limited to an organic material. For example, the organic layer may also include an inorganic material.

Description of FIG. 1

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Organic Layer 150]

The organic layer 150 is on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include the diamine compound.

The hole transport region may further include, in addition to the diamine compound, at least one selected from m-MTDATA, TDATA, 2-TNATA, NPB(NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

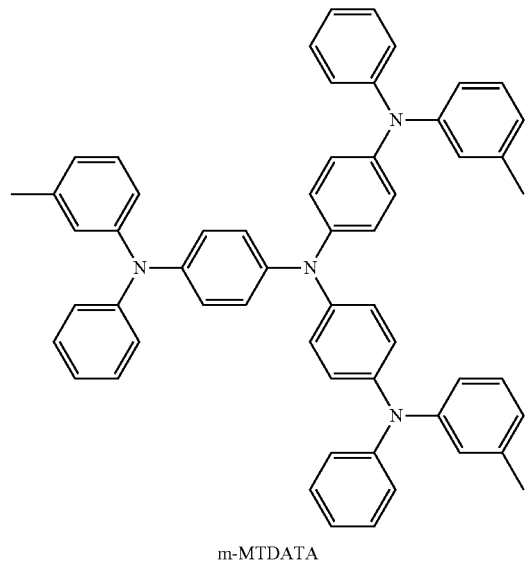

m-MTDATA

-continued
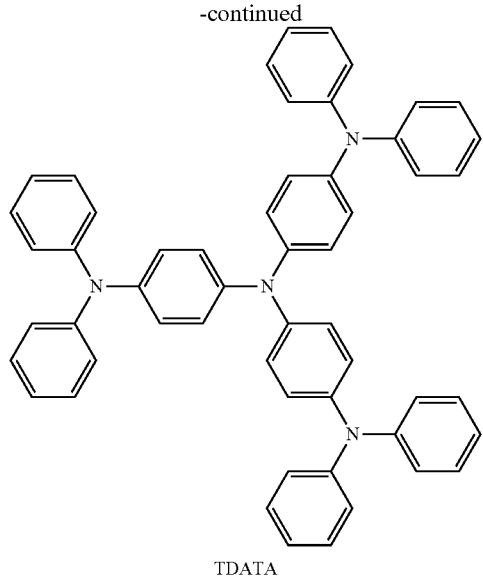
TDATA
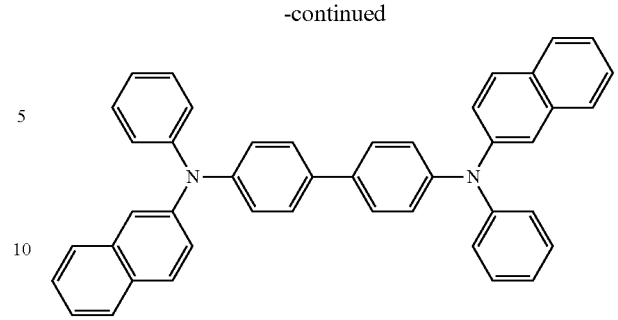
β-NPB
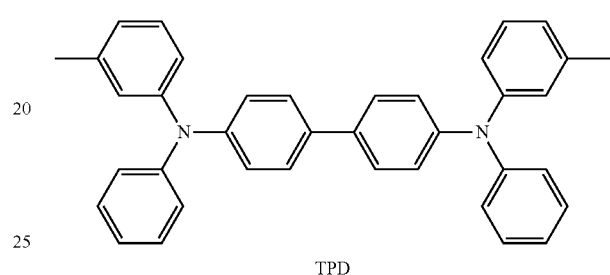
TPD
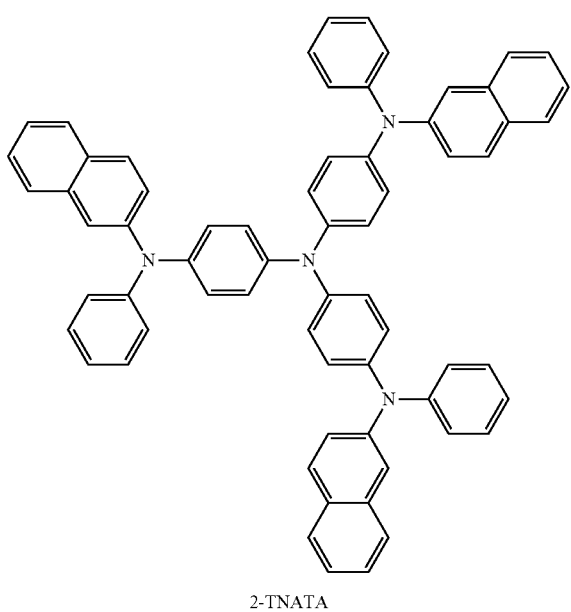
2-TNATA
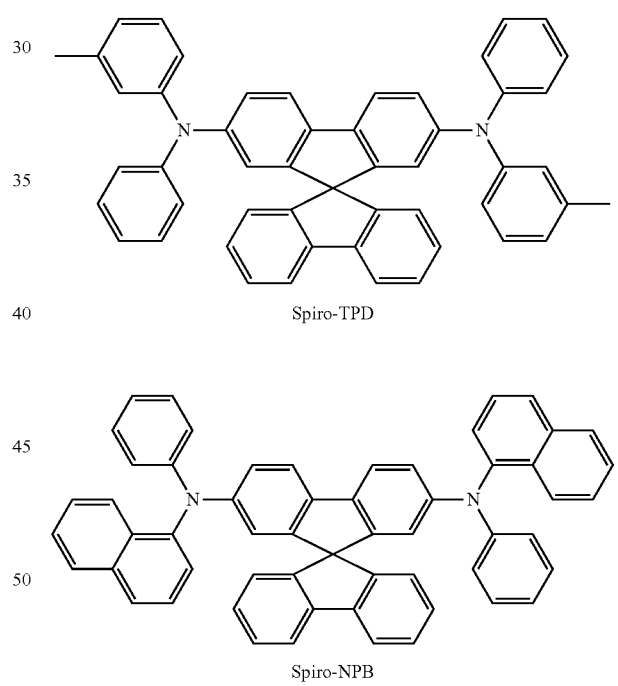
Spiro-TPD
Spiro-NPB
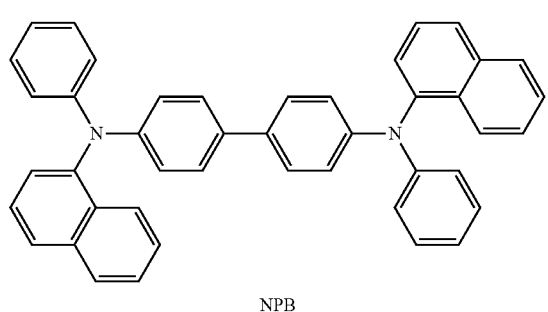
NPB
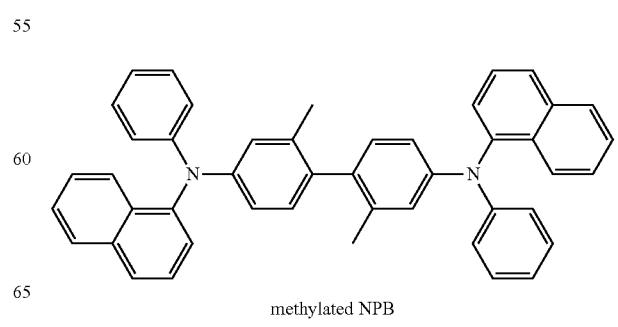
methylated NPB

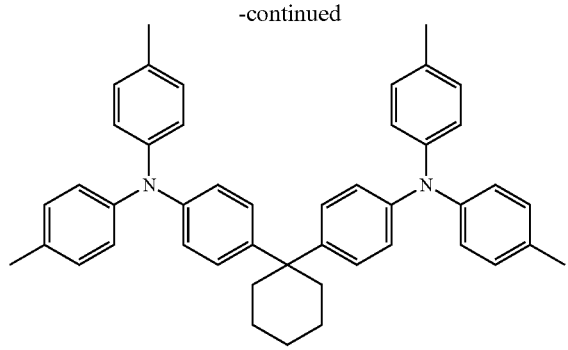

TAPC

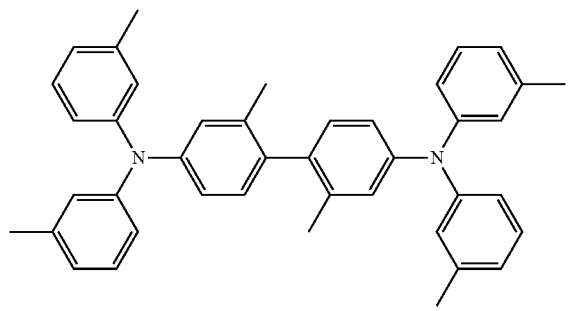

HMTPD

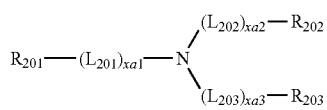

Formula 201

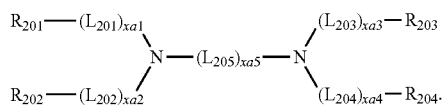

Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one embodiment, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_0$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be the same as described above.

In one or more embodiments, in Formula 201, at least one selected from $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202, i) $R_{201}$ and $R_{202}$ may be linked via a single bond, and/or ii) $R_{203}$ and $R_{204}$ may be linked via a single bond.

In one or more embodiments, in Formula 202, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201 may be represented by Formula 201A:

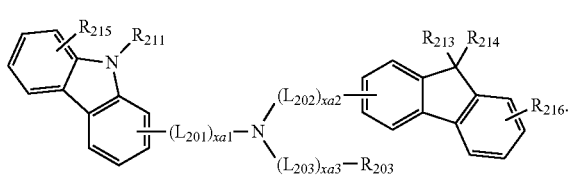

Formula 201A

In one embodiment, the compound represented by Formula 201 may be represented by Formula 201A(1) below, but embodiments of the present disclosure are not limited thereto:

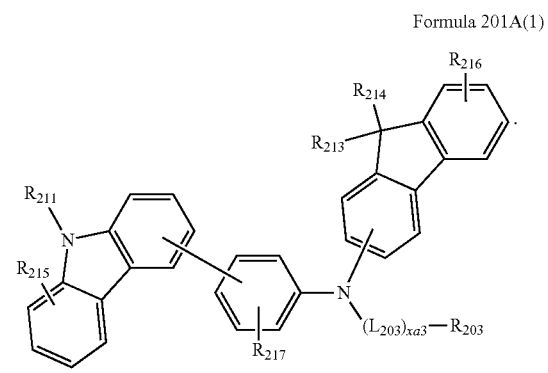

Formula 201A(1)

In one embodiment, the compound represented by Formula 201 may be represented by Formula 201A-1 below, but embodiments of the present disclosure are not limited thereto:

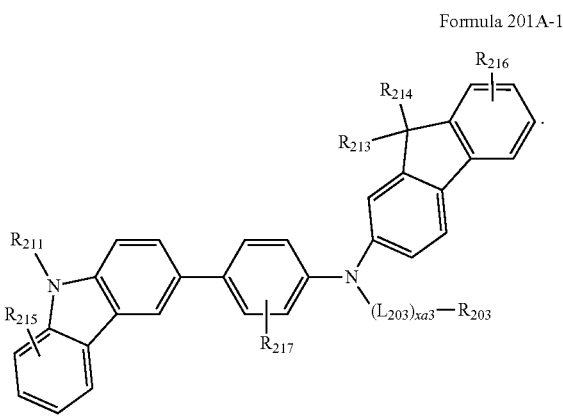

Formula 201A-1

In one embodiment, the compound represented by Formula 202 may be represented by Formula 202A:

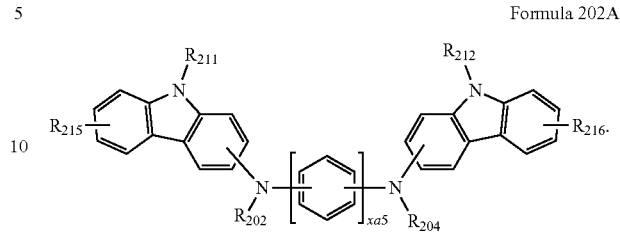

Formula 202A

In one or more embodiments, the compound represented by Formula 202 may be represented by Formula 202A-1:

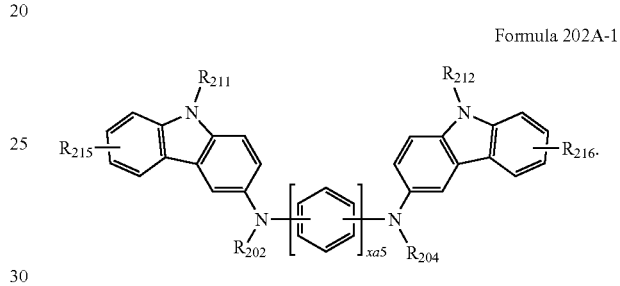

Formula 202A-1

In Formulae 201A, 201A(1), 201A-1, 202A, and 202A-1, $L_{201}$ to $L_{203}$, xa1 to xa3, xa5, and $R_{202}$ to $R_{204}$ may each independently be the same as described above, $R_{211}$ and $R_{212}$ may each independently be the same as described in connection with $R_{203}$, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

61 HT1 62 HT2
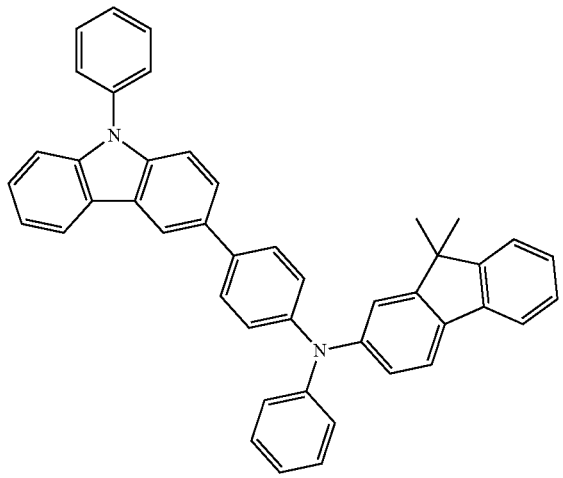
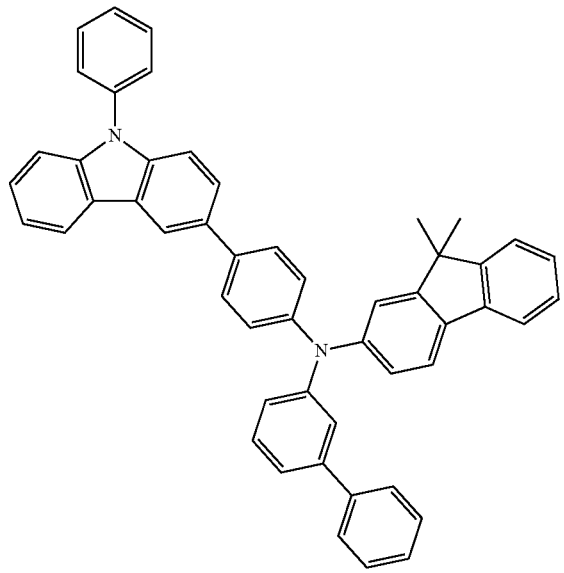
HT3 HT4
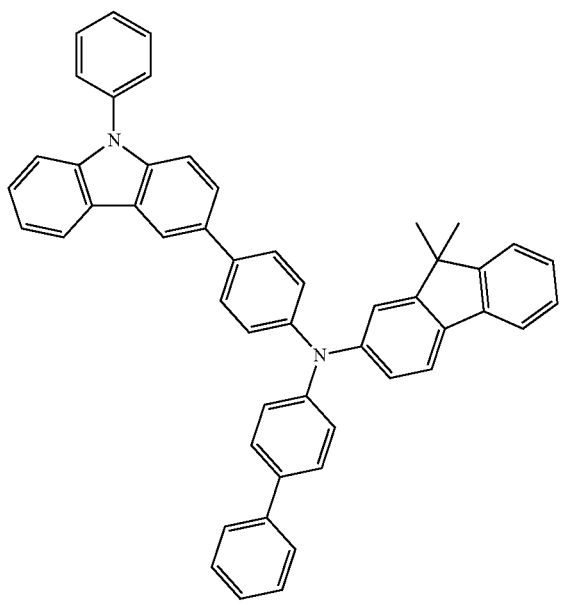
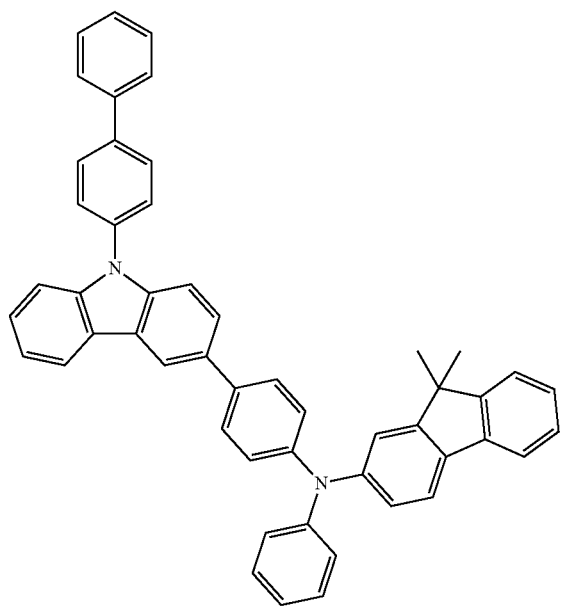

-continued
HT5
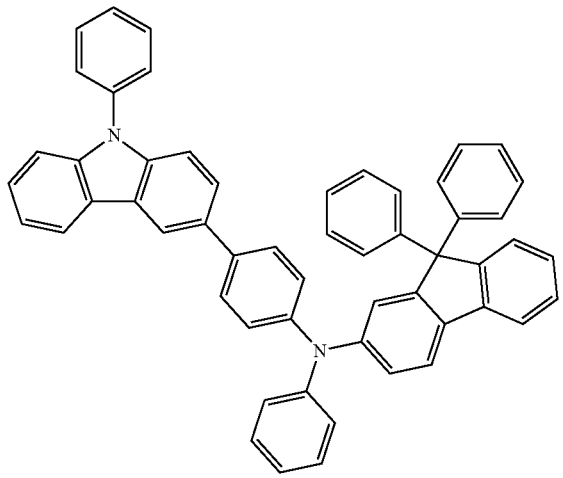
HT6
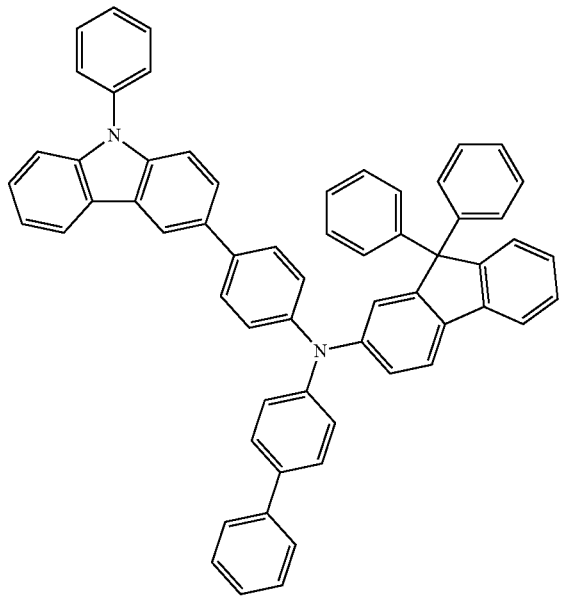
HT7
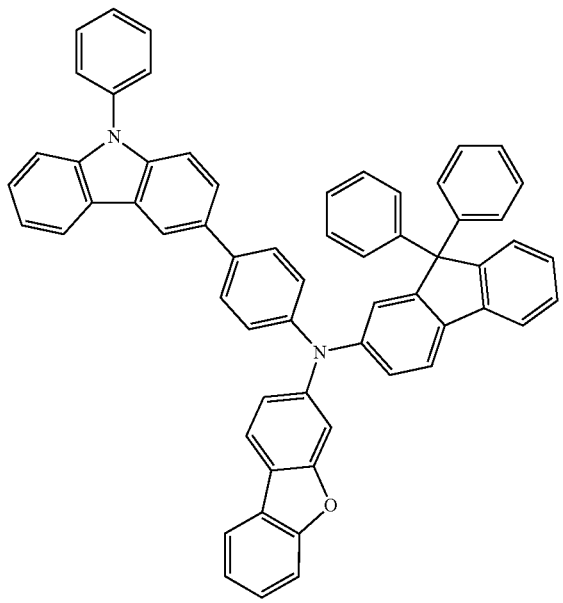
HT8
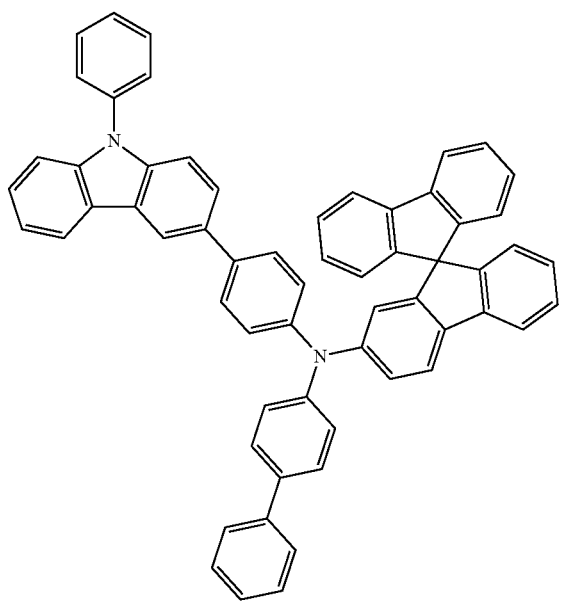

-continued
HT9
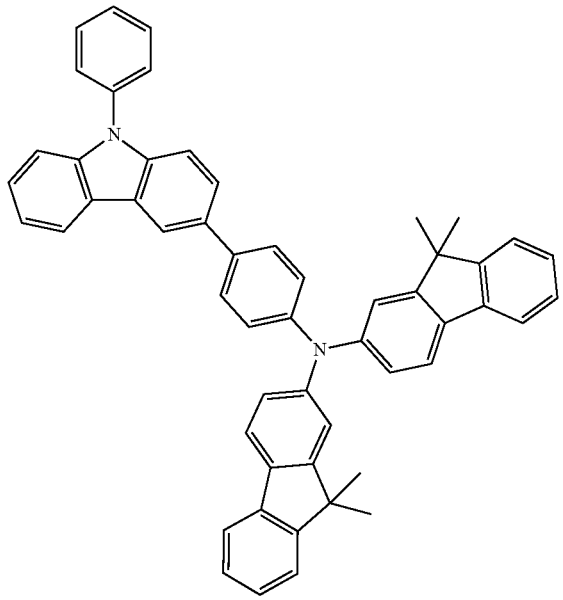
HT10
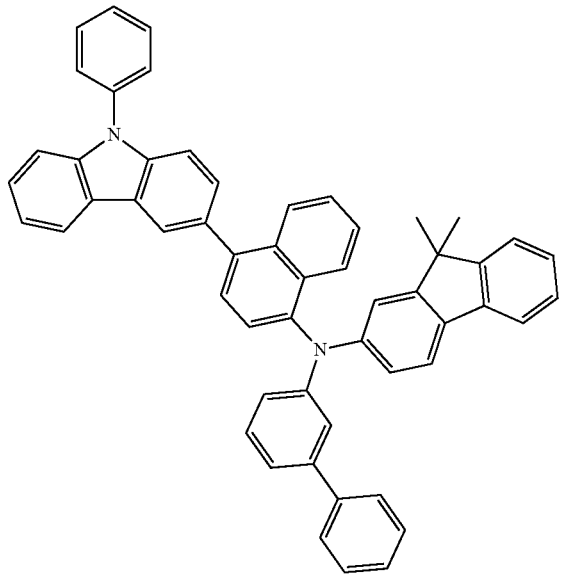
HT11
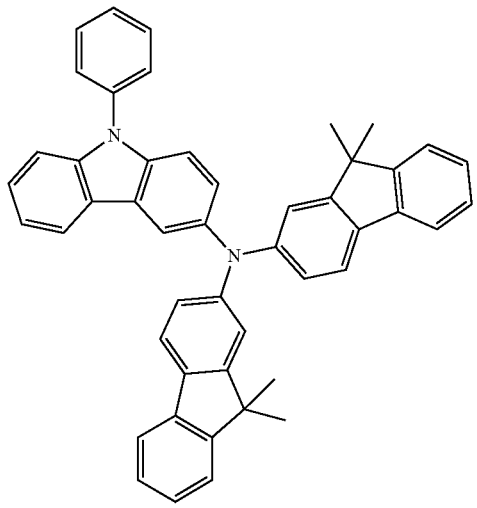
HT12
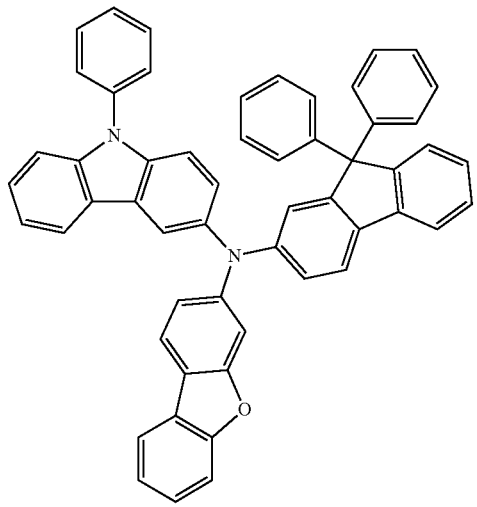

-continued
HT13
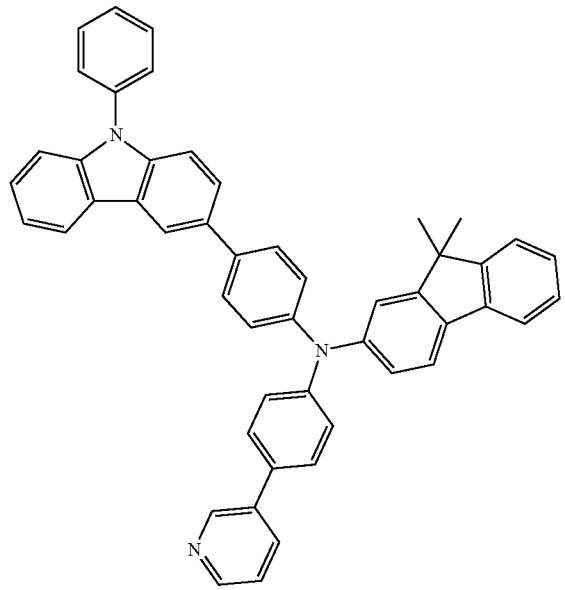
HT14
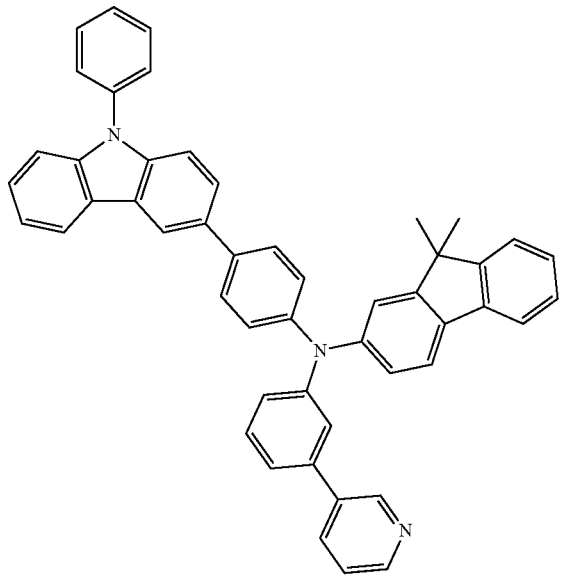
HT15
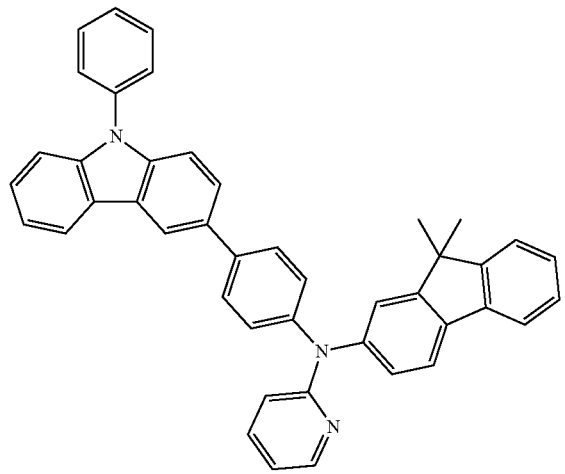
HT16
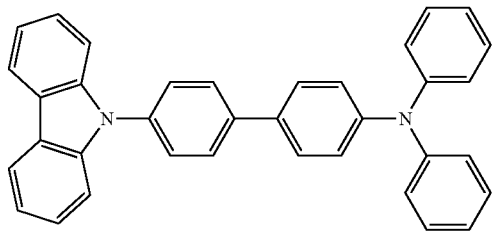
HT17
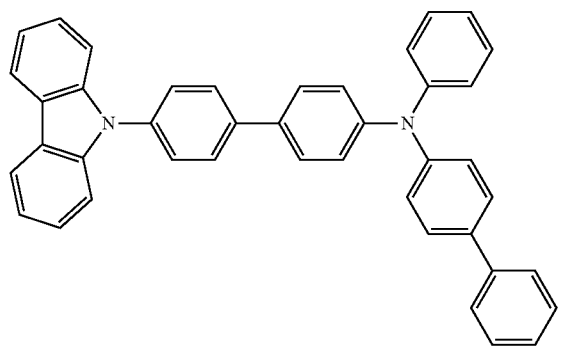
HT18
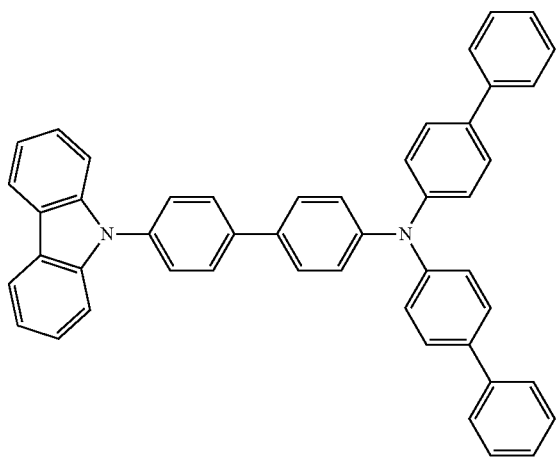

-continued
HT19
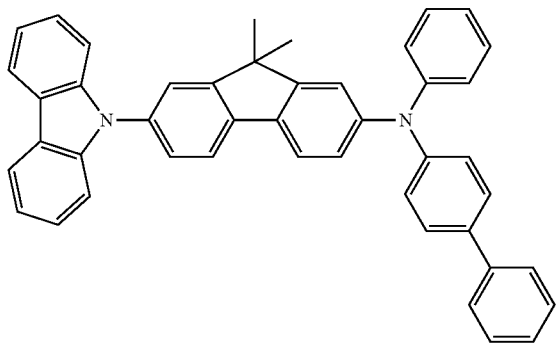
HT20
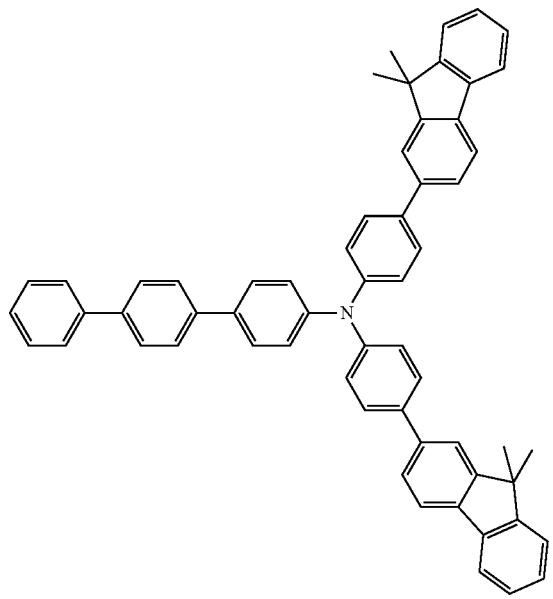
HT21
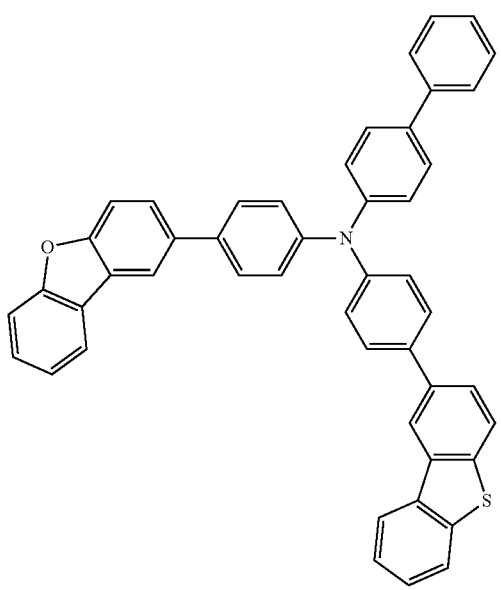
HT22
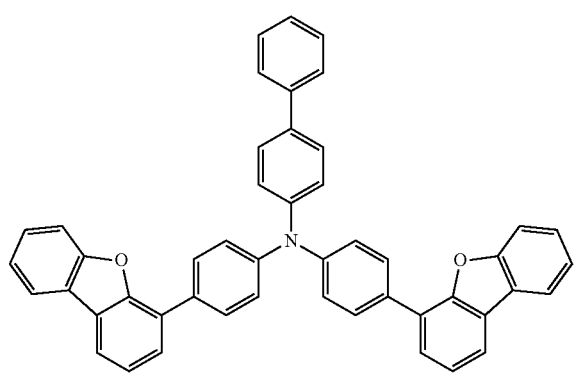

HT23
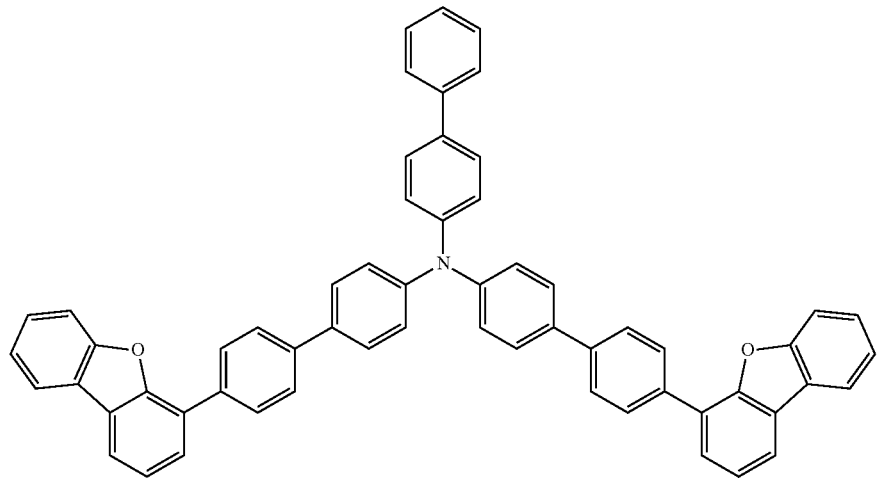
HT24
HT25
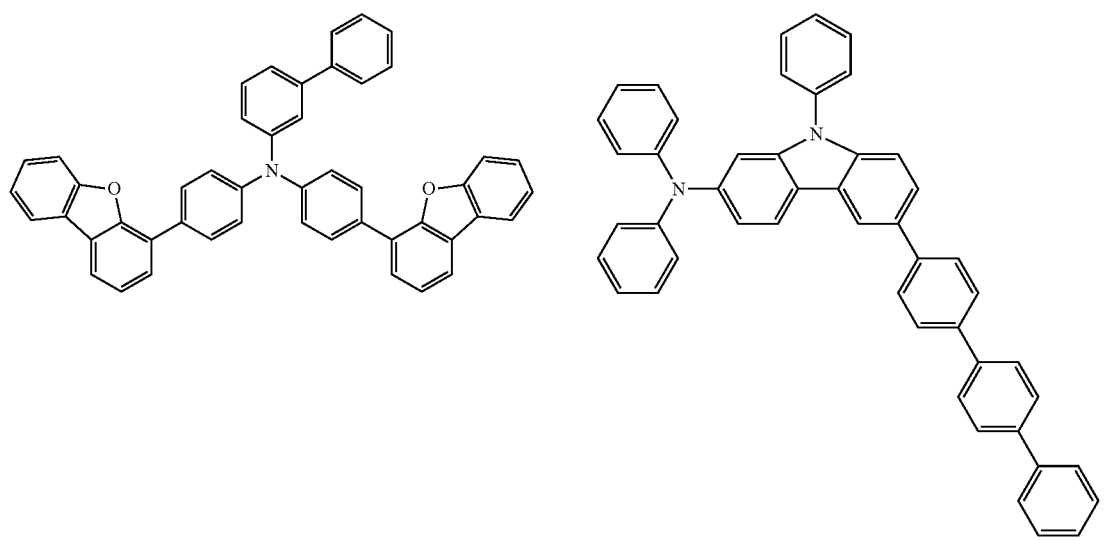
HT26
HT27
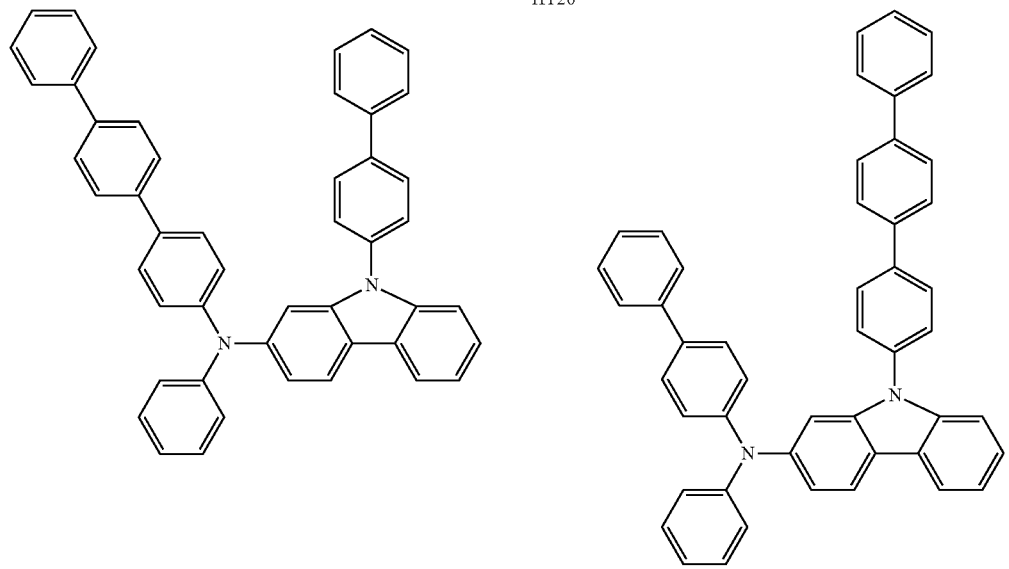

-continued
HT28
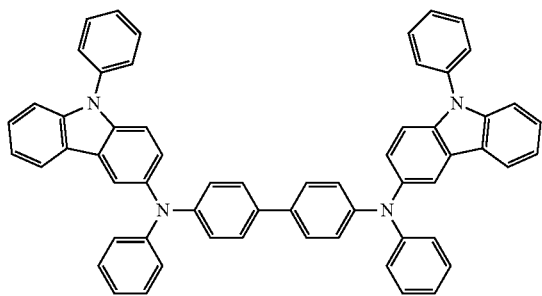
HT29
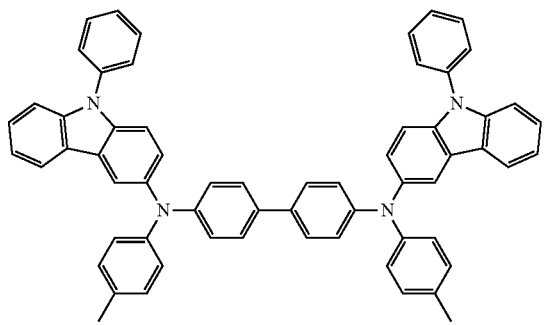
HT30
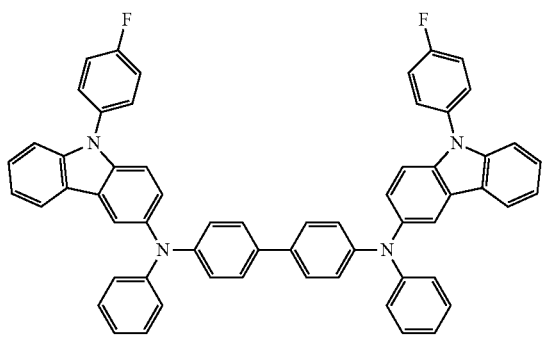
HT31
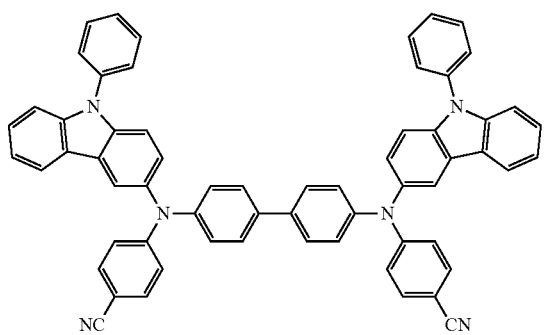
HT32
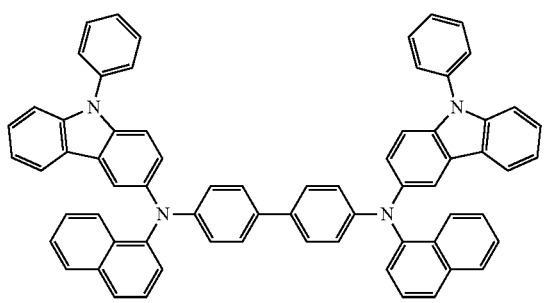
HT33
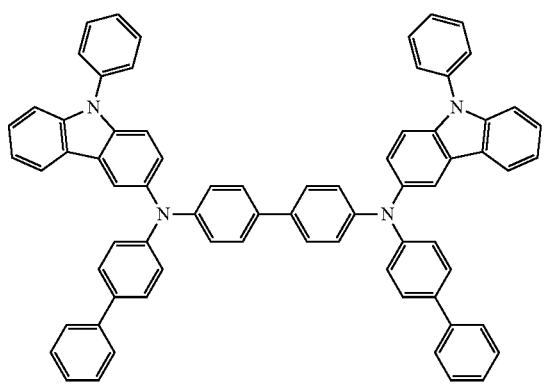
HT34
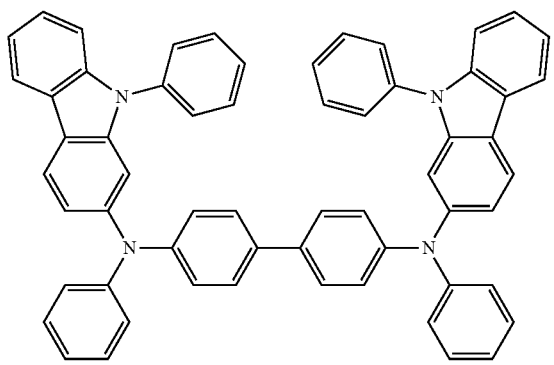
HT35
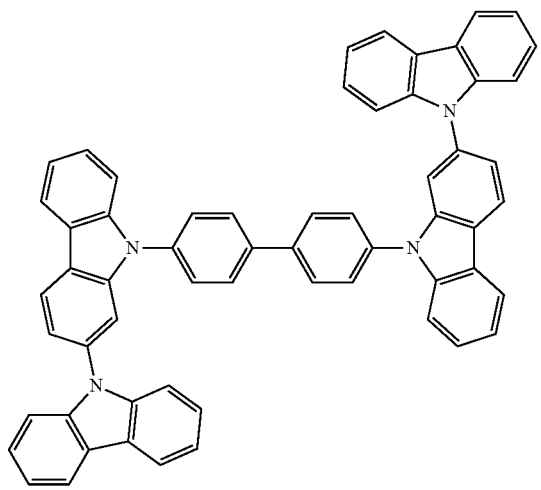

-continued

HT36
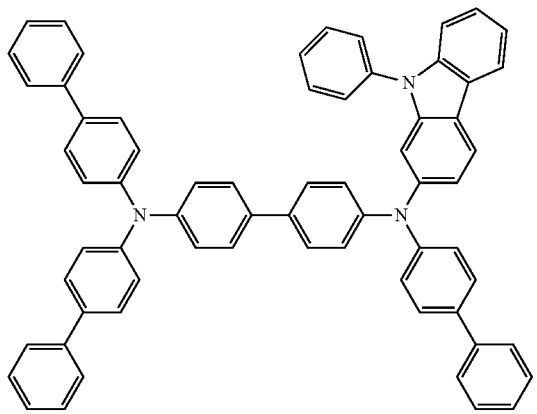

HT37
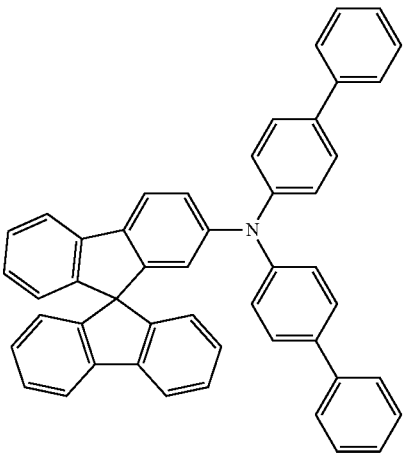

HT38
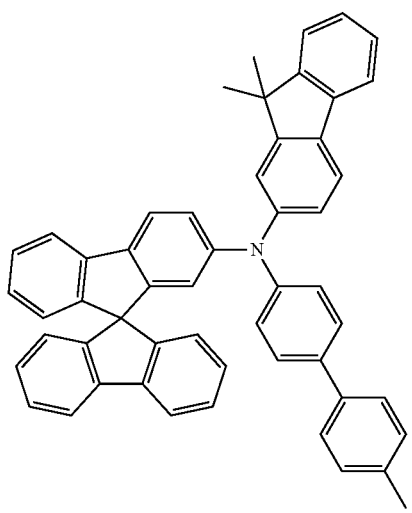

HT39
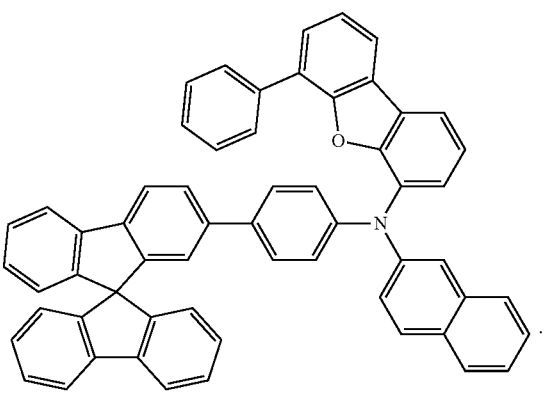

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

p-dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) level of −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:

a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,12-hexaazatriphenylene-hexacarbonitrile (HAT-CN); and a compound represented by Formula 221, but embodiments of the present disclosure are not limited thereto:

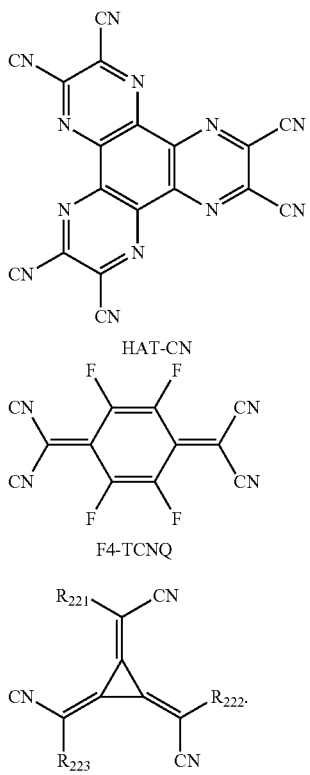

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

The emission layer may include a host and a dopant. The dopant may include at least one selected from a phosphorescent dopant and a fluorescent dopant.

In the emission layer, an amount of the dopant may be in a range of about 0.01 parts by weight to about 15 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Host in Emission Layer

In one or more embodiments, the host may include a compound represented by Formula 301:

$$[Ar_{301}]_{xb11}\text{-}[(L_{301})_{xb1}\text{-}R_{301}]_{xb21}. \quad \text{Formula 301}$$

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

When xb11 in Formula 301 is two or more, two or more of Ar301(s) may be linked via a single bond.

In one or more embodiments, the compound represented by Formula 301 may be represented by Formula 301-1 or 301-2:

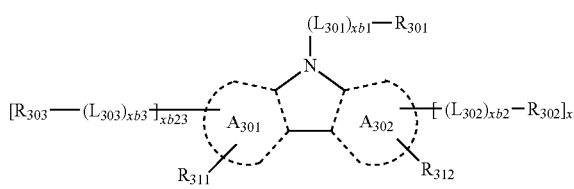

Formula 301-1

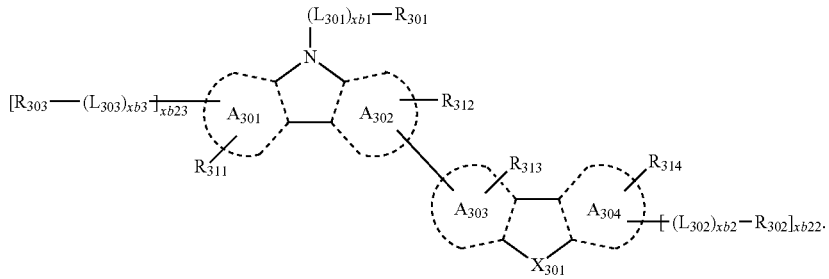

Formula 301-2

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$, and $Q_{31}$ to $Q_{33}$ may each independently be the same as described above, $L_{302}$ to $L_{304}$ may each independently be the same as described in connection with $L_{301}$, xb2 to xb4 may each independently be the same as described in connection with xb1, and $R_{302}$ to $R_{304}$ may each independently be the same as described in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may each independently be the same as described above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, and $Q_{31}$ to $Q_{33}$ may each independently be the same as described above.

In one or more embodiments, the host may include an alkaline earth metal complex. For example, the host may be selected from a Be complex (for example, Compound H55), a Mg complex, and a Zn complex.

The host may include at least one selected from 9,10-di (2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

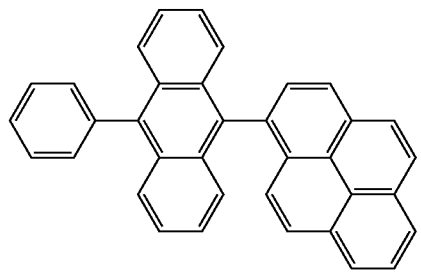

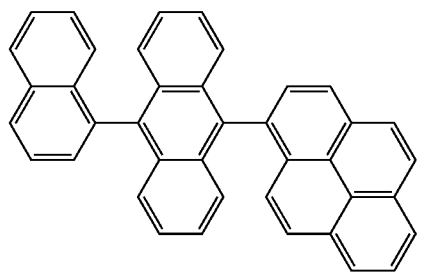

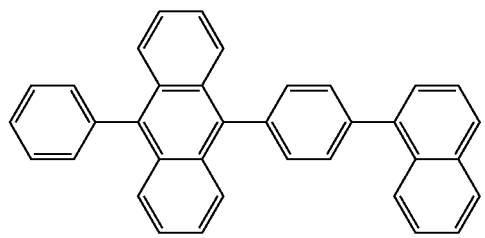

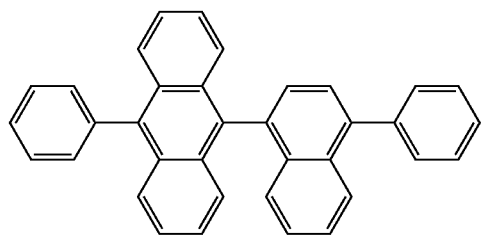

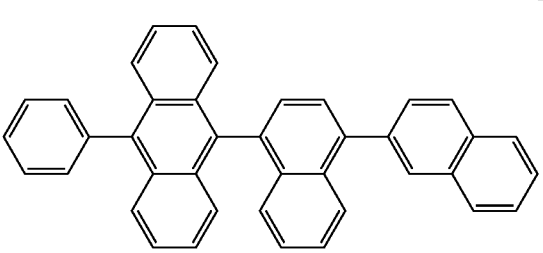

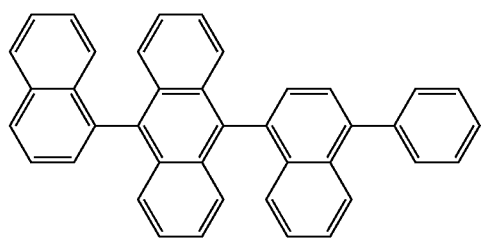

-continued
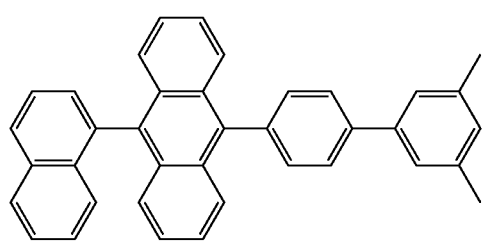
H11
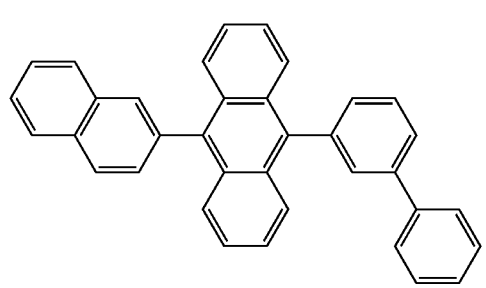
HT12
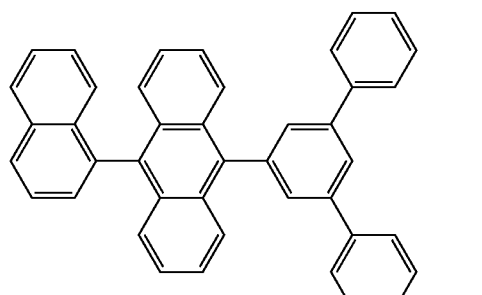
HT13
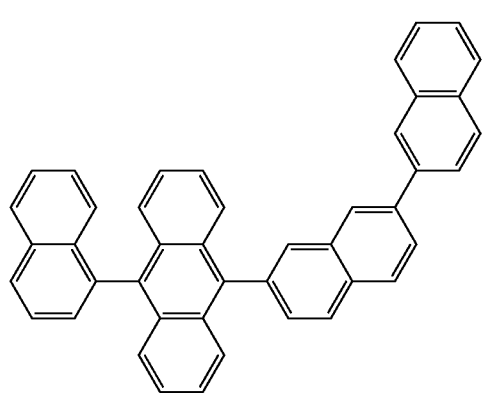
HT14
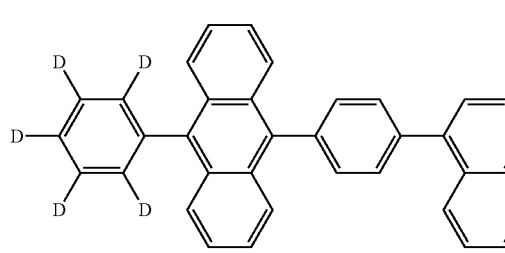
H15
-continued
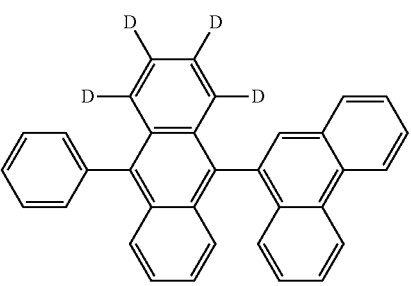
H16
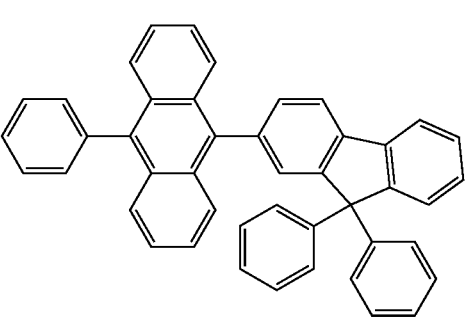
H17
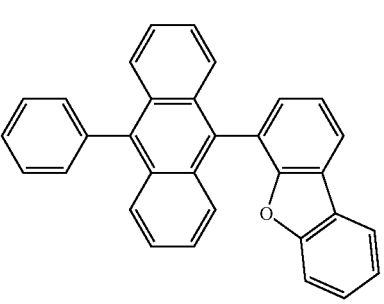
H18
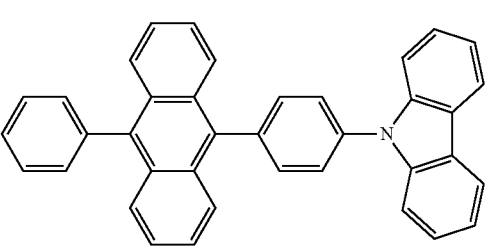
H19
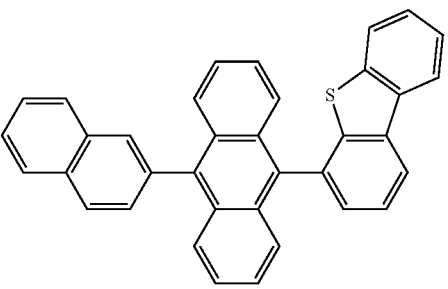
H20

H21
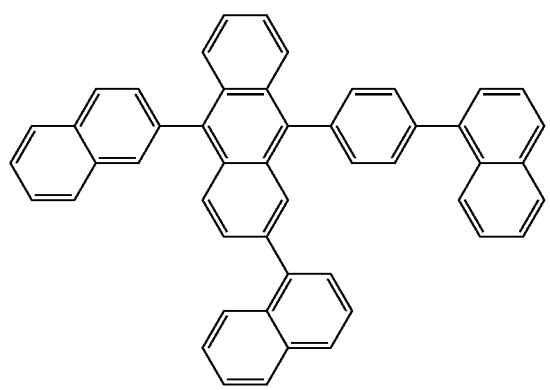
H22
H23
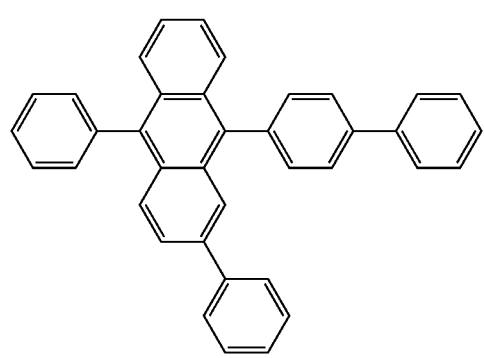
H24
H25
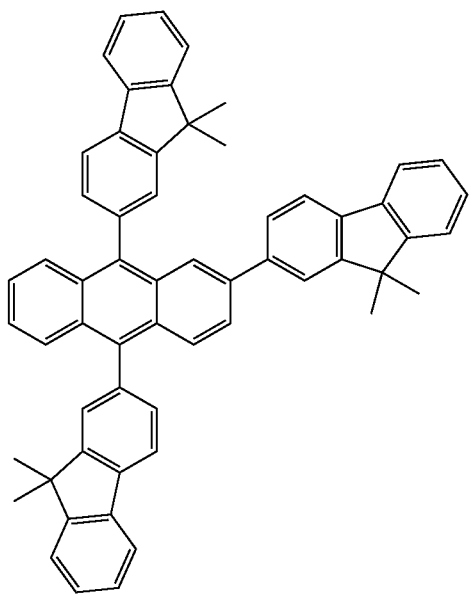
H26
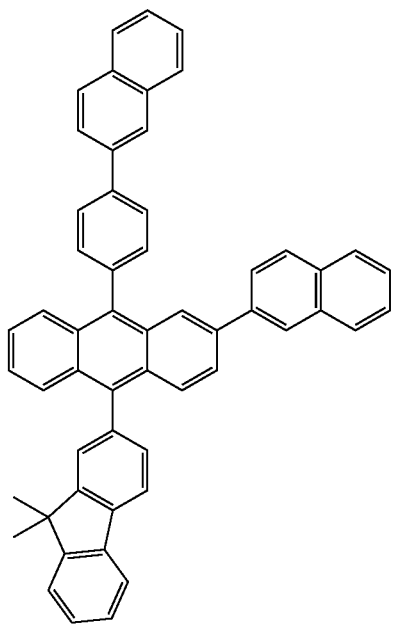

-continued
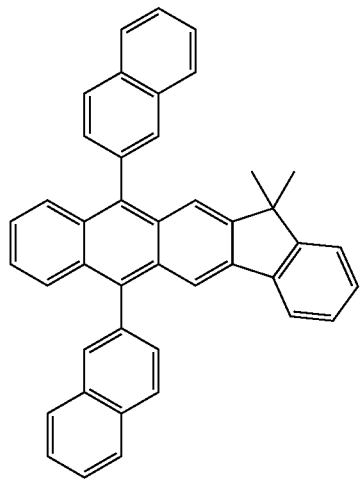
H27
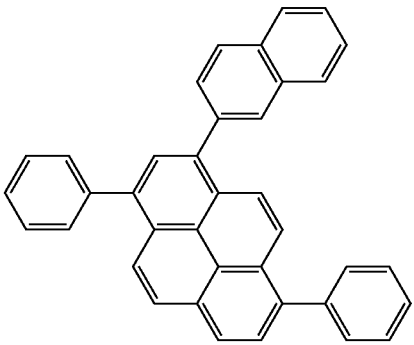
H30
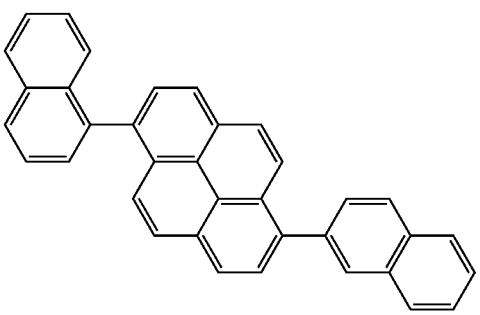
H31
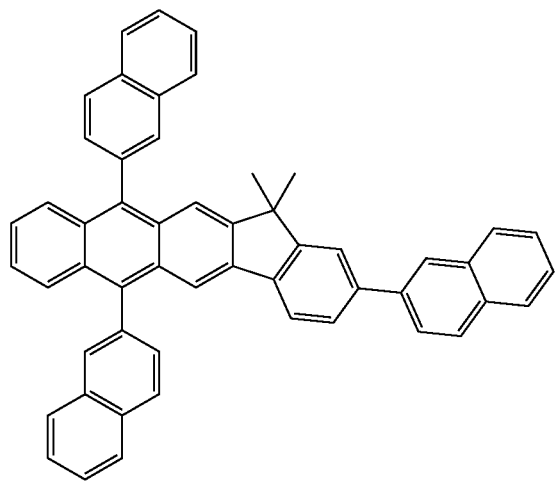
H28
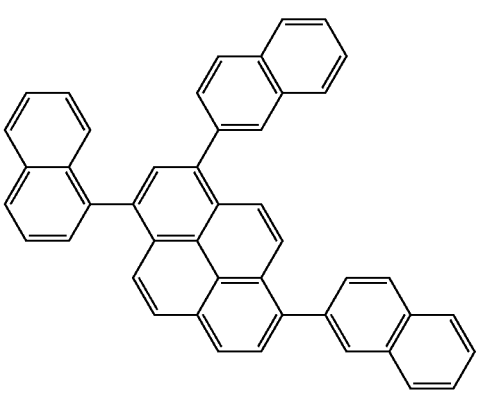
H32
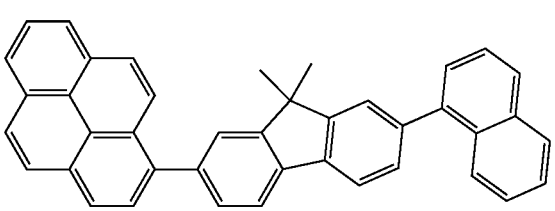
H33
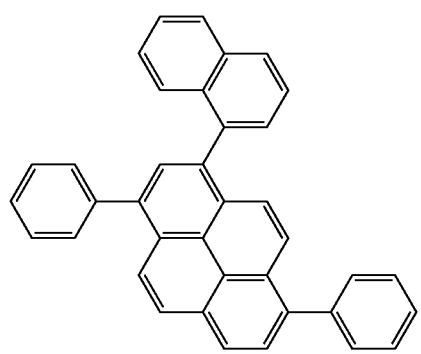
H29
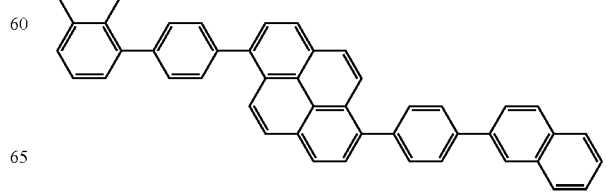
H34

H35
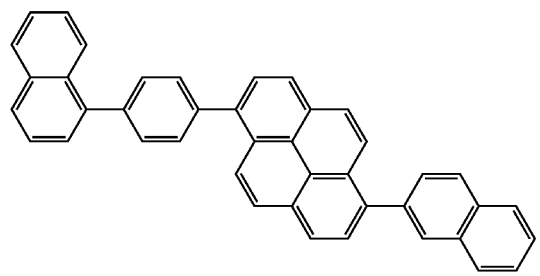
H36
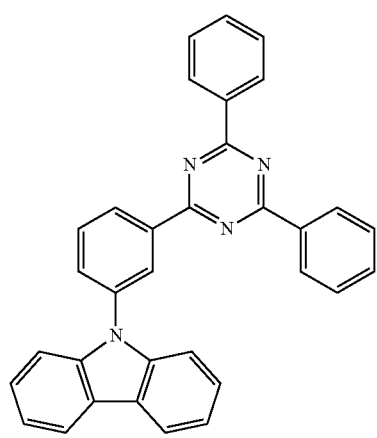
H37
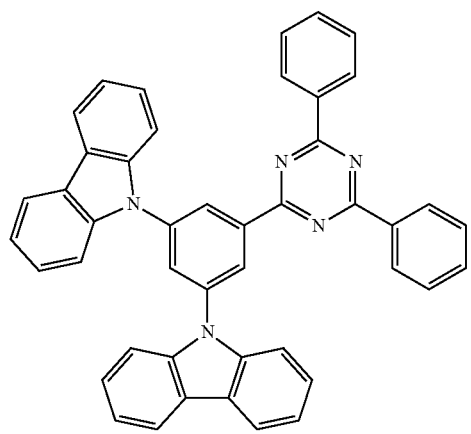
H38
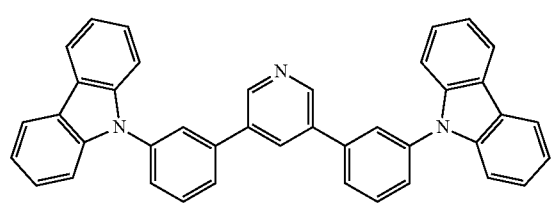
H39
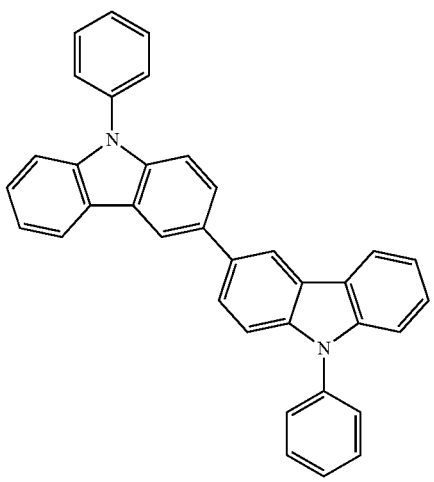
H40
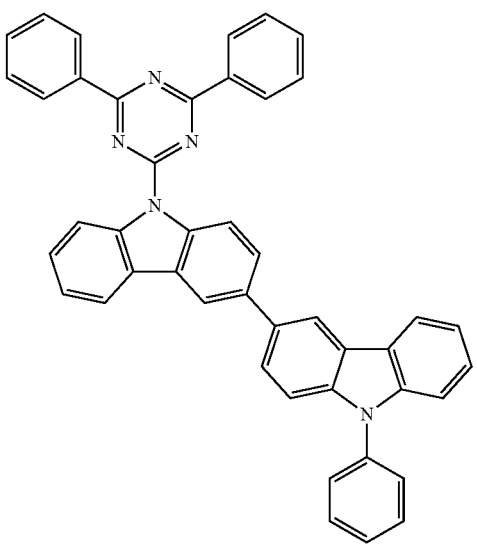
H41
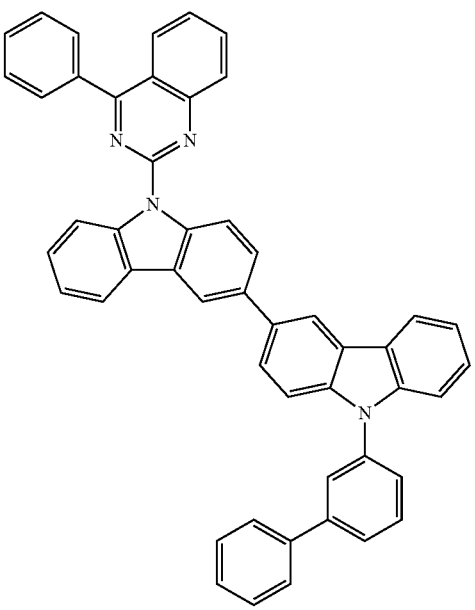

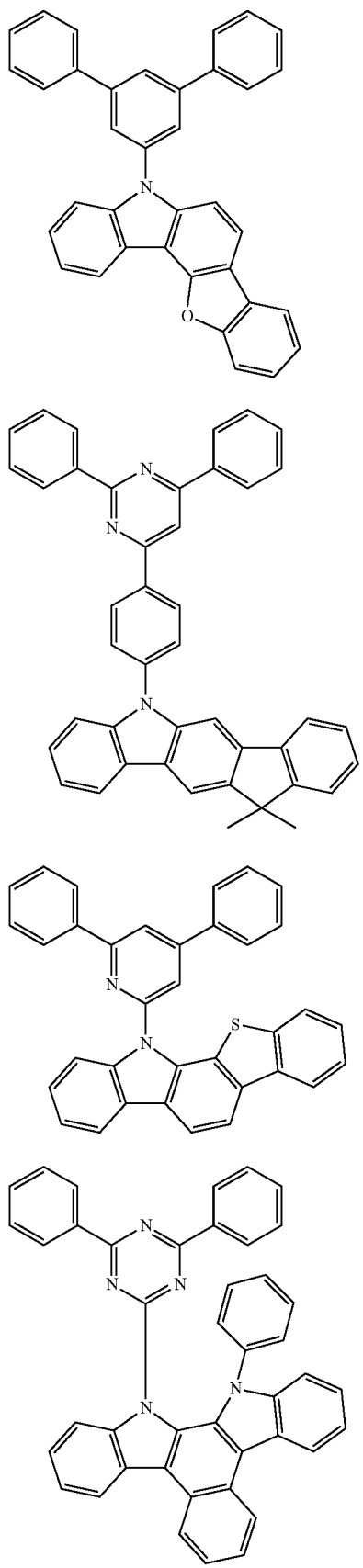
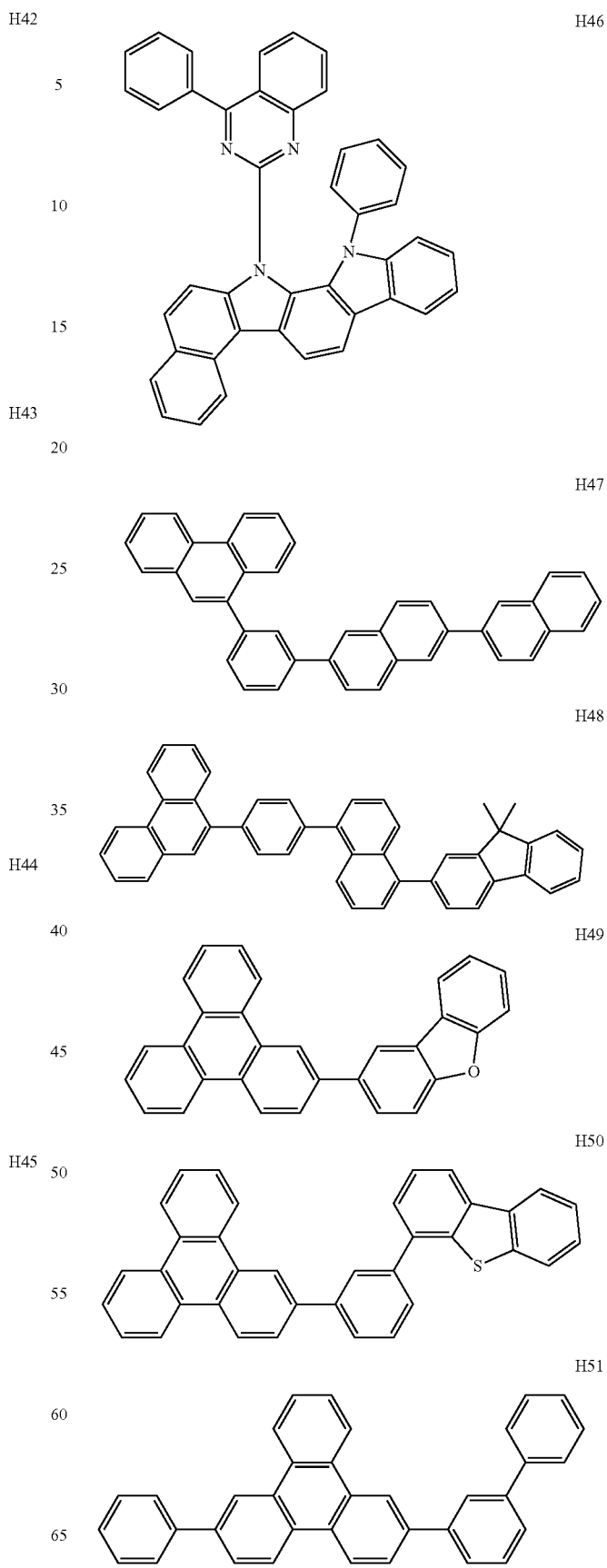

-continued

H52 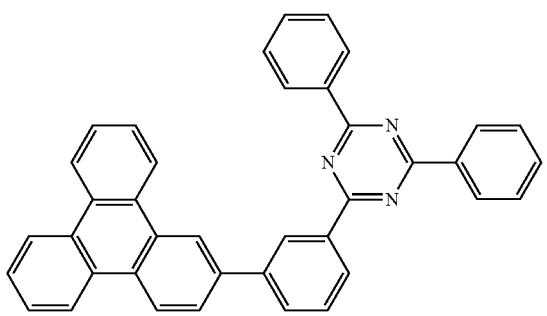

H53 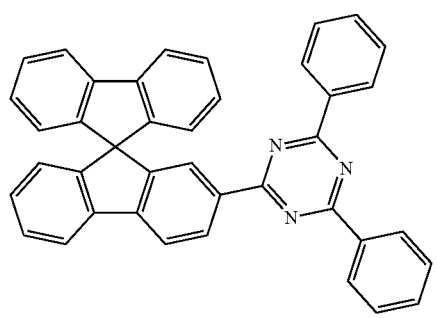

H54 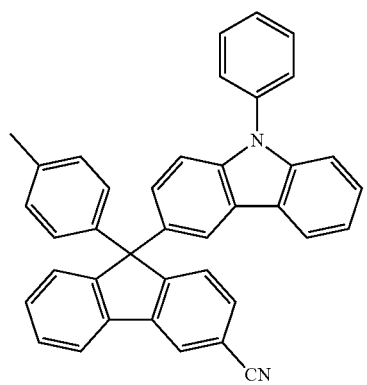

H55 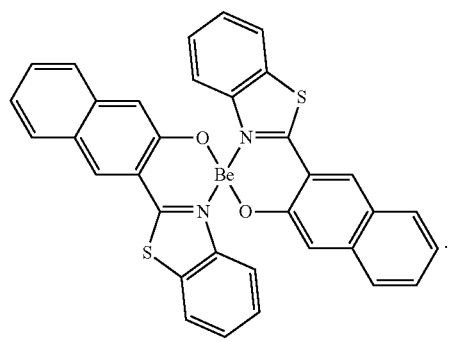

Phosphorescent Dopant Included in Emission Layer in Organic Layer 150

The phosphorescent dopant may include an organometallic complex represented by Formula 401 below:

$$M(L_{401})_{xc1}(L_{402})_{xc2}$$ Formula 401

Formula 402

(diagram of ligand structure with $A_{401}$, $A_{402}$, $X_{401}$–$X_{406}$, $R_{401}$, $R_{402}$)

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}$(s) may be identical to or different from each other, $L_{402}$ may be an organic ligand, and xc2 may be an integer from 0 to 4, wherein, when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be a $C_5$-$C_{60}$ carbocyclic group or $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*, *—C($Q_{411}$)=C($Q_{412}$)-*', *—C($Q_{411}$)=*', or *=C=*', wherein $Q_{411}$ and $Q_{412}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$ ($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer from 0 to 10, and

* and *' in Formula 402 each indicate a binding site to M in Formula 401.

In one embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may be both nitrogen.

In one or more embodiments, in Formula 402, $R_{401}$ and $R_{402}$ may each independently be selected from:
hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;
a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;
a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;
a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, in Formula 401, when xc1 is two or more, two $A_{401}$(S) among two or more of $L_{401}$(S) may optionally be linked via a linking group, such as $X_{407}$, or when xc2 is two or more, two $A_{402}$(s) among two or more $L_{402}$(s) may optionally be linked via a linking group, such as $X_{408}$ (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but embodiments of the present disclosure are not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite), but embodiments of the present disclosure are not limited thereto.

In one or more embodiments, the phosphorescent dopant may be selected from, for example, Compounds PD1 to PD25, but embodiments of the present disclosure are not limited thereto:

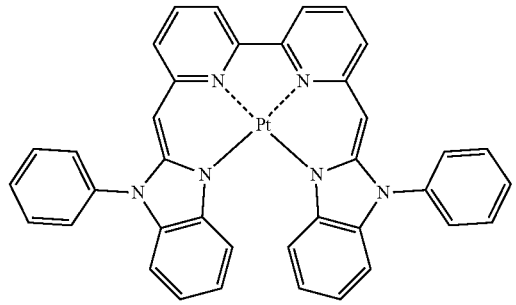

PD1

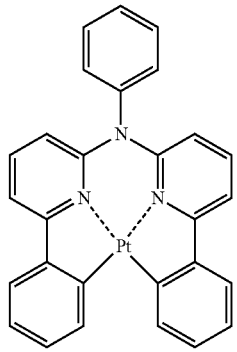

PD2

-continued
PD3
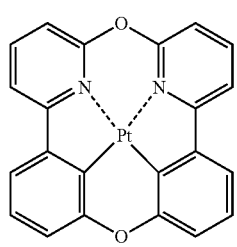
PD4
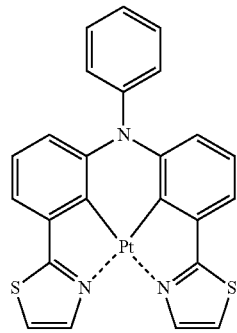
PD5
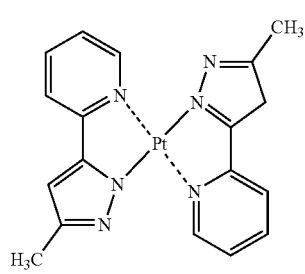
PD6
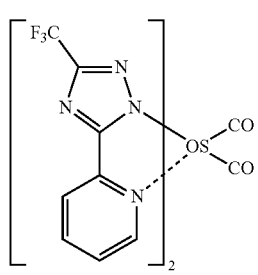
PD7
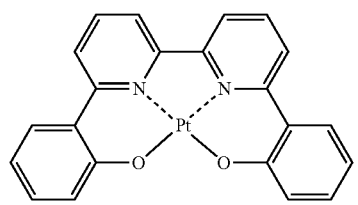
PD8
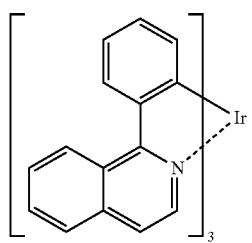
-continued
PD9
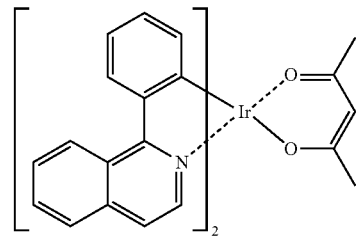
PD10
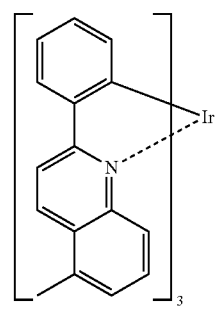
PD11
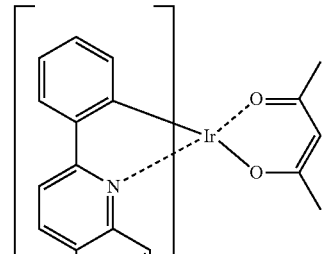
PD12
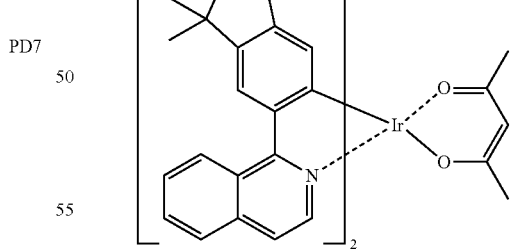
PD13
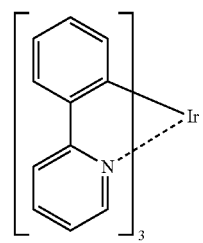

PD14 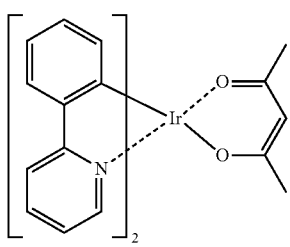
PD15 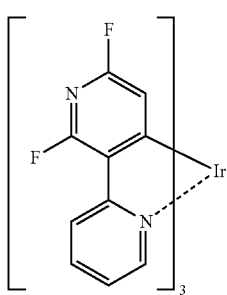
PD16 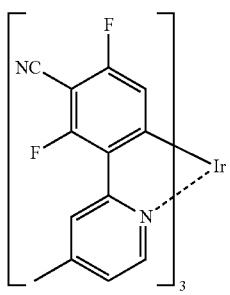
PD17 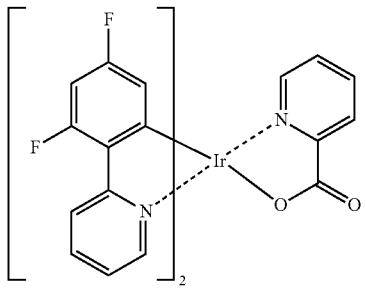
PD18 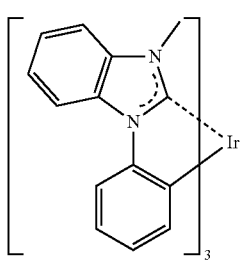
PD19 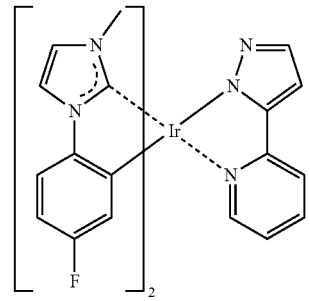
PD20 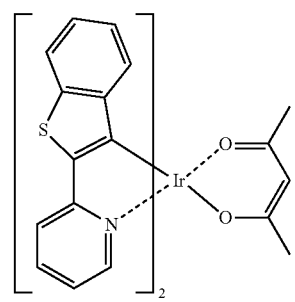
PD21 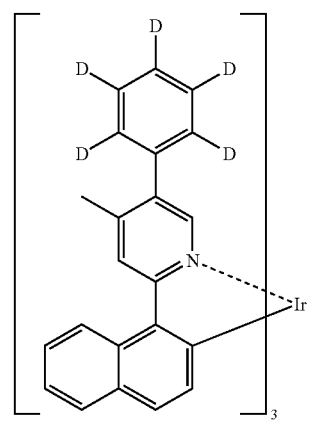
PD22 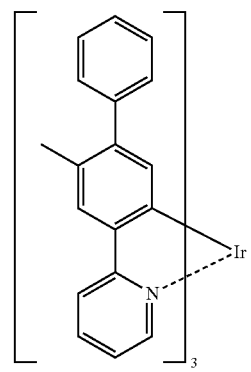

-continued

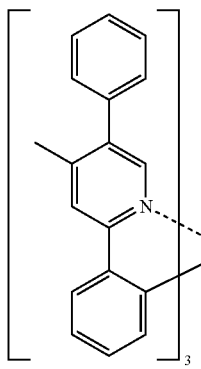
PD23

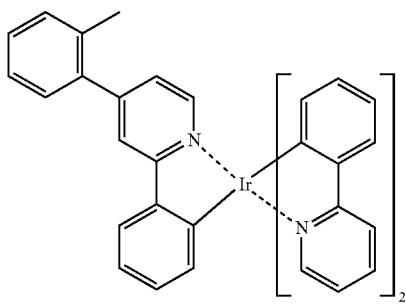
PD24

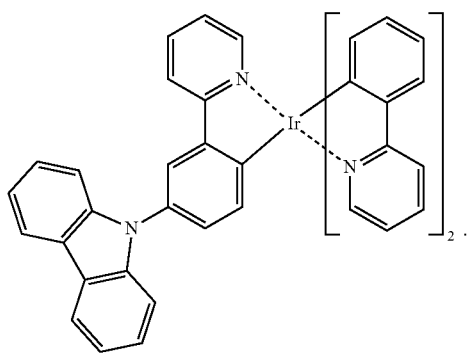
PD25.

Fluorescent Dopant in Emission Layer

The fluorescent dopant may include an arylamine compound or a styrylamine compound.

The fluorescent dopant may include a compound represented by Formula 501:

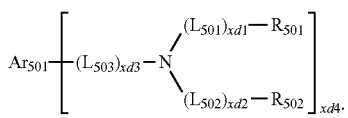
Formula 501

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{00}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, in Formula 501, xd4 may be 2, but embodiments of the present disclosure are not limited thereto.

For example, the fluorescent dopant may be selected from Compounds FD1 to FD22:

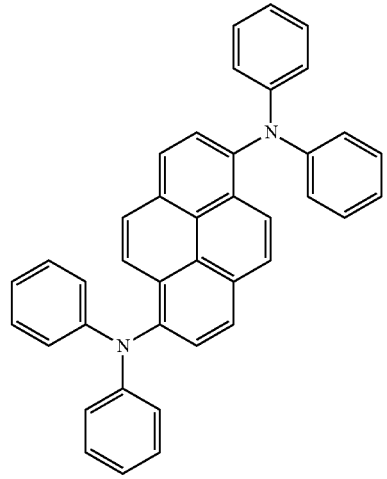

FD1

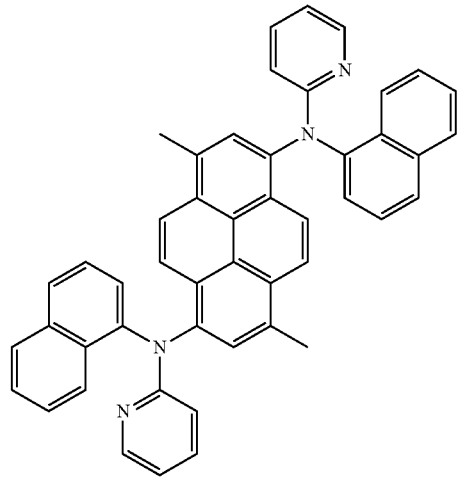

FD2

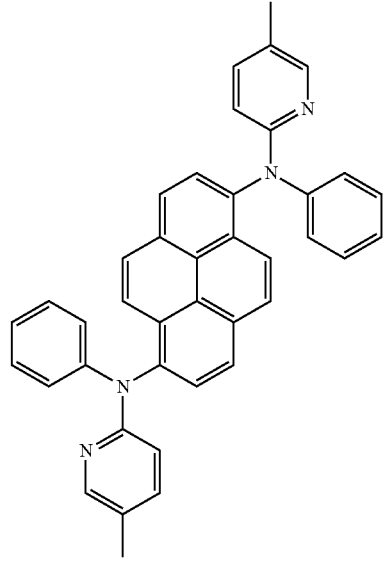

FD3

FD4
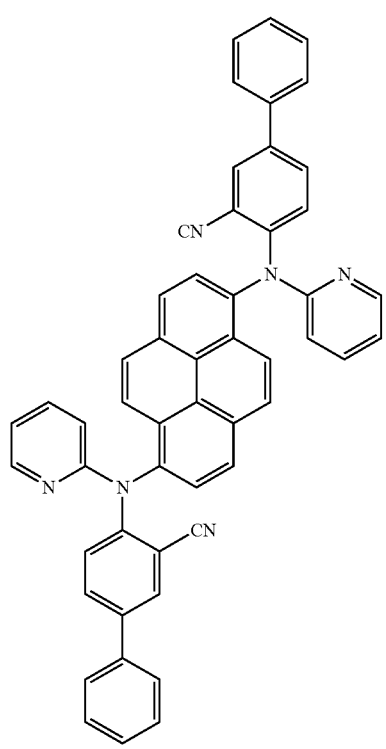
FD5
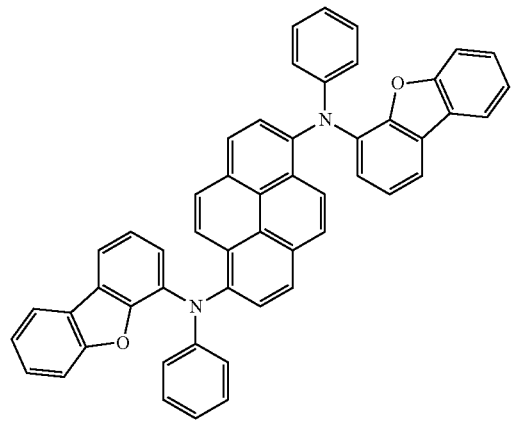
FD6
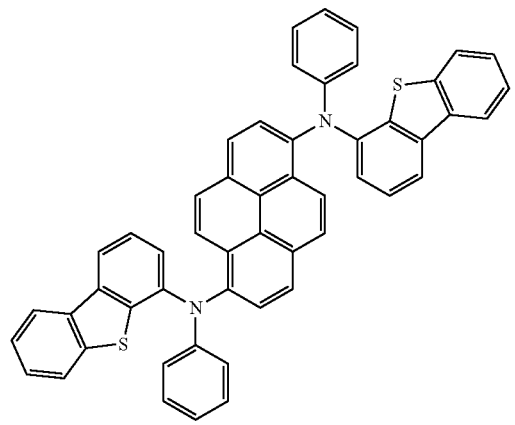
FD7
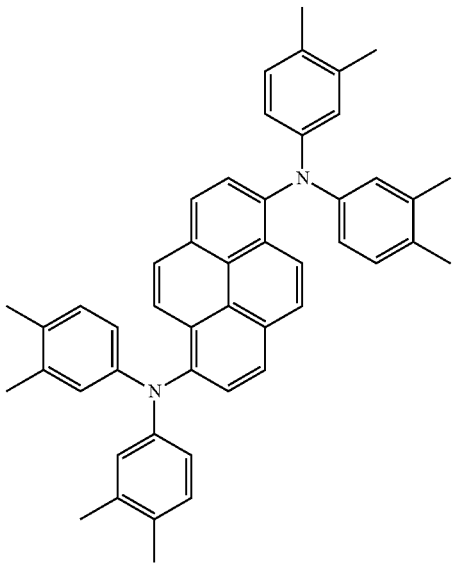
FD8
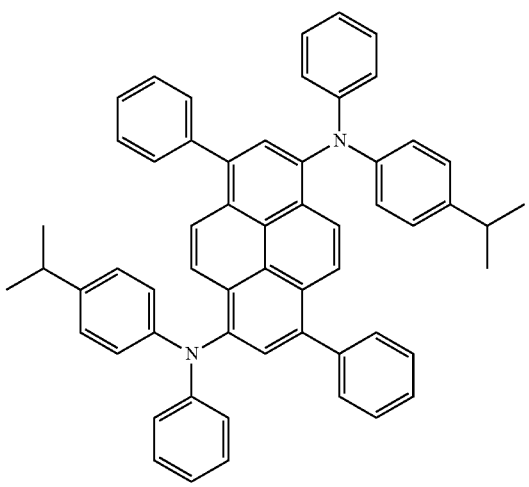
FD9
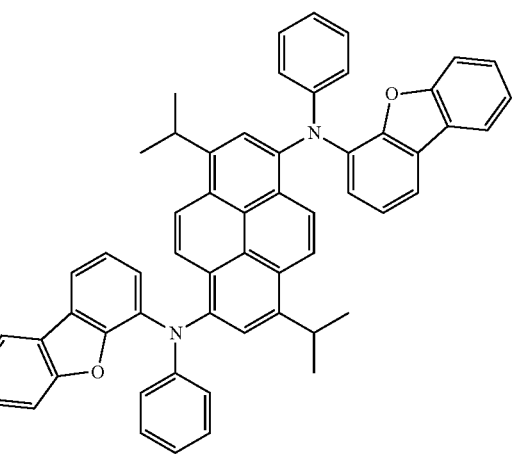

FD10
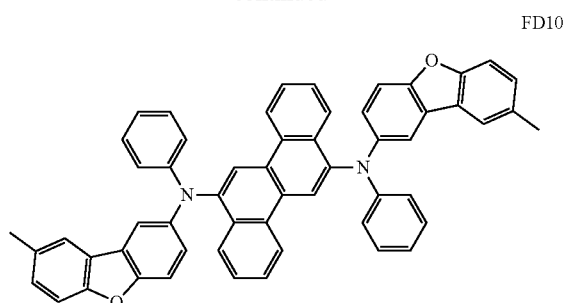
FD11
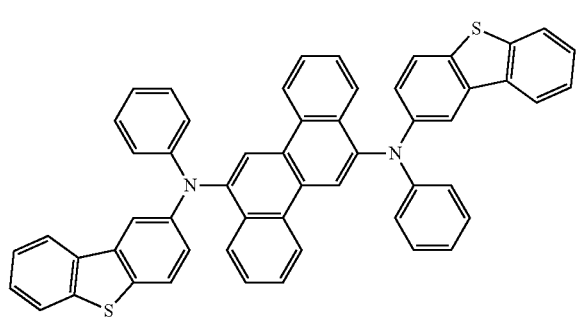
FD12
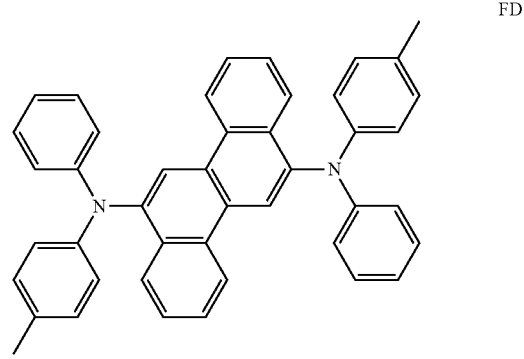
FD13
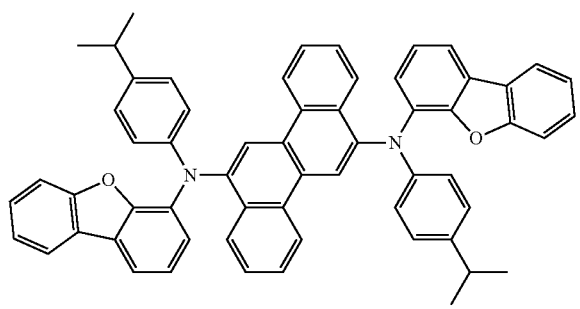
FD14
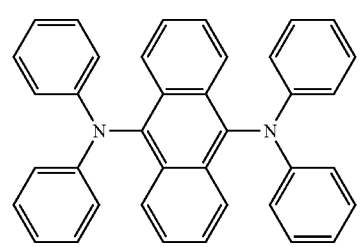
FD15
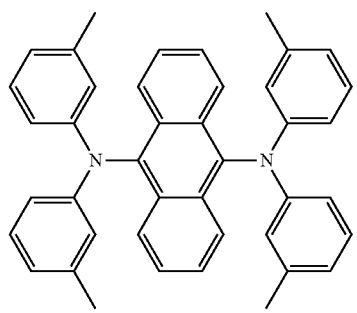
FD16
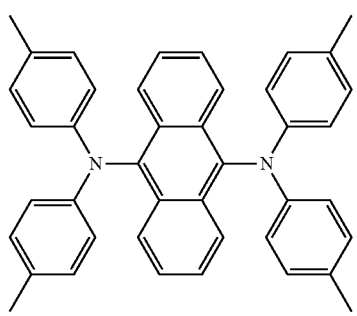
FD17
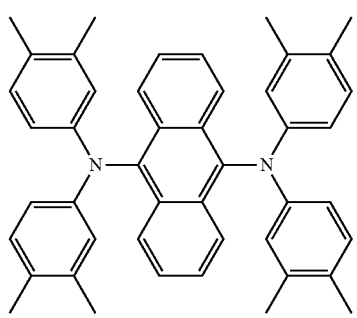
FD18
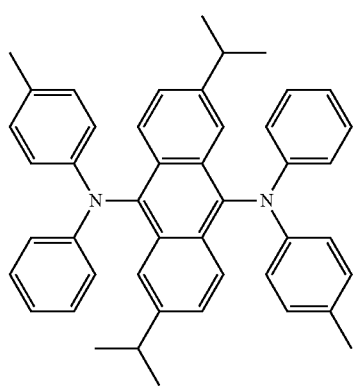

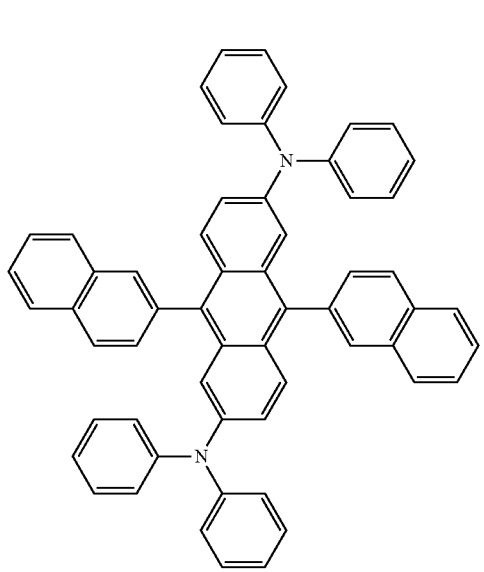
FD19
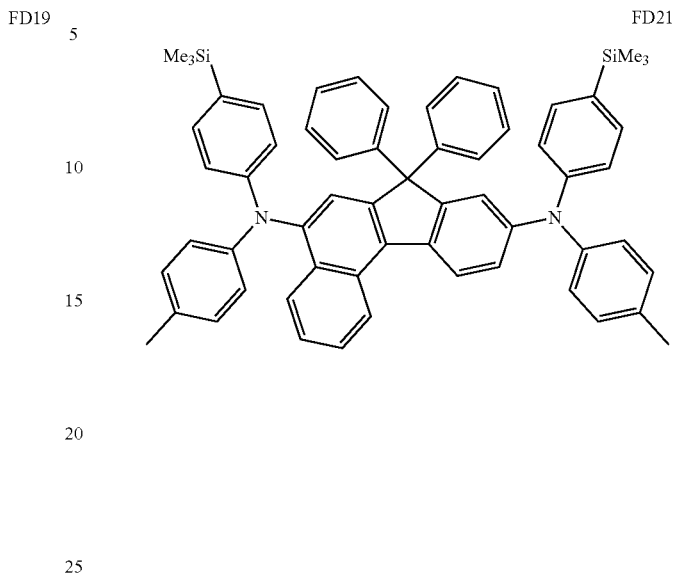
FD21
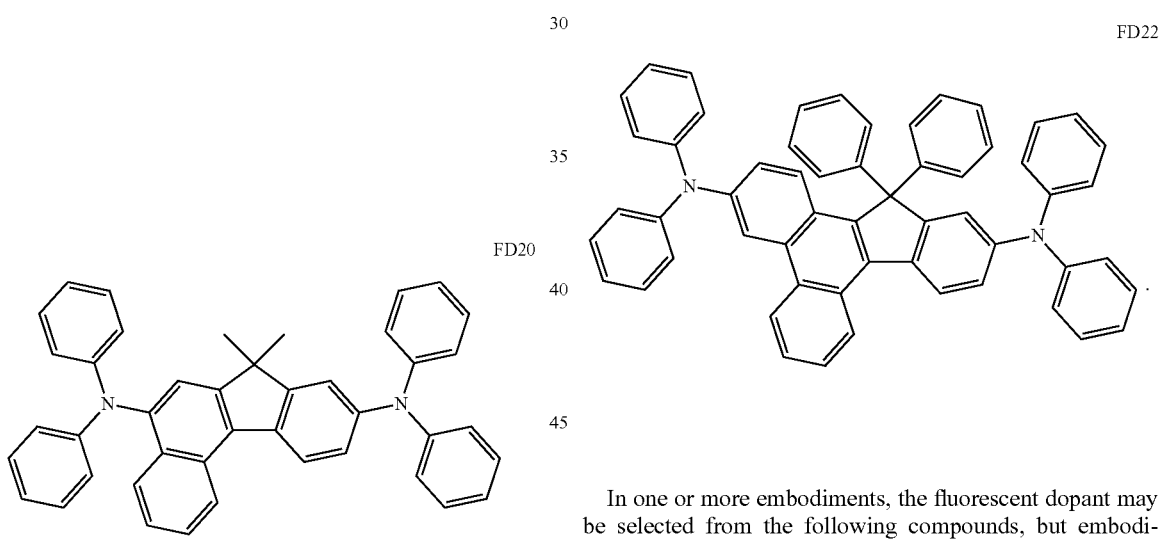
FD20
FD22
In one or more embodiments, the fluorescent dopant may be selected from the following compounds, but embodiments of the present disclosure are not limited thereto.
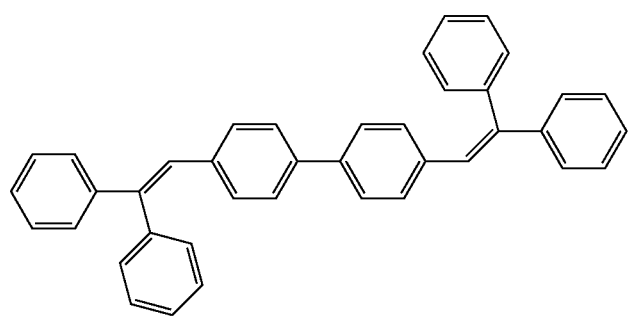
DPVBi

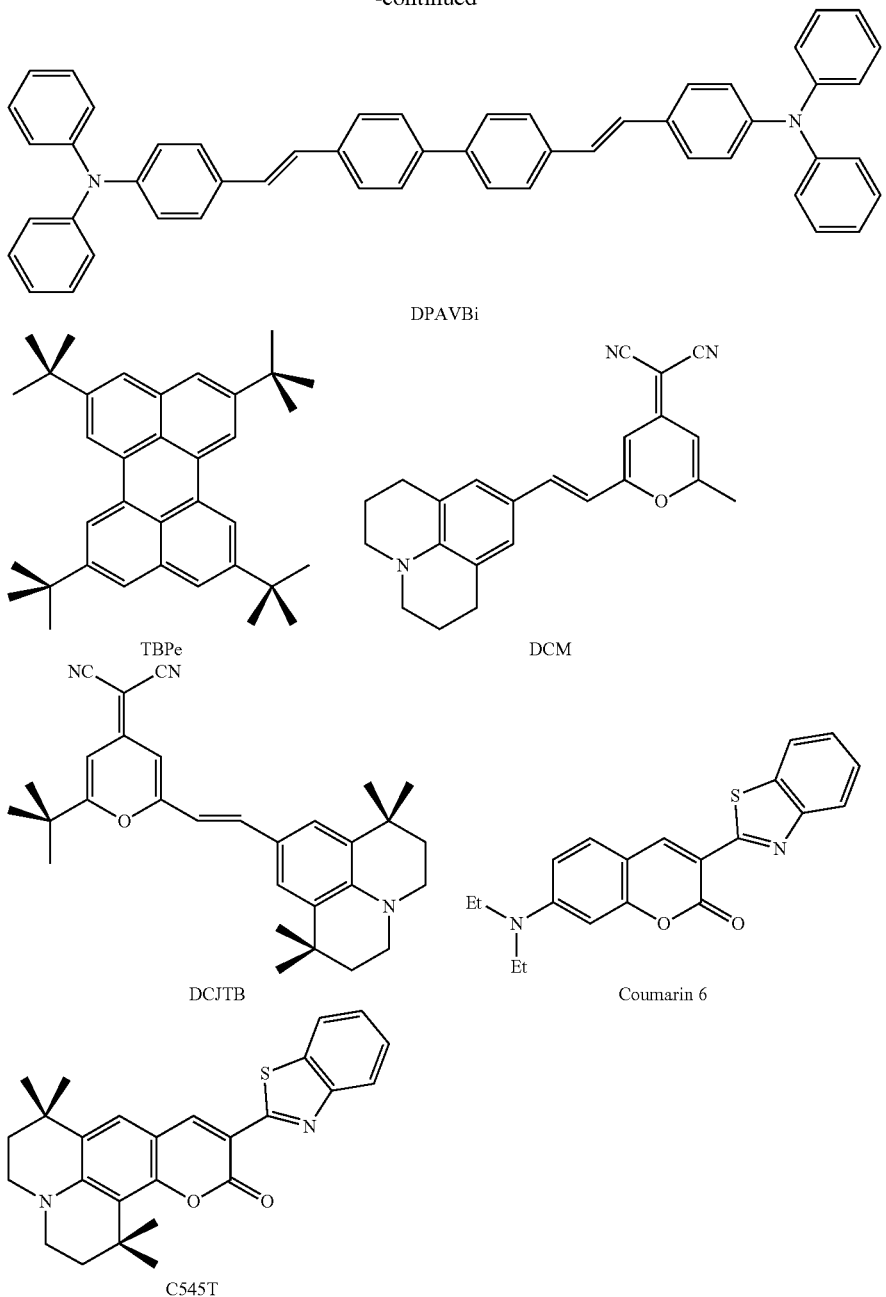

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, embodiments of the structure of the electron transport region are not limited thereto.

The electron transport region (for example, a buffer layer, a hole blocking layer, an electron control layer, or an electron transport layer in the electron transport region) may include a metal-free compound containing at least one π electron-depleted nitrogen-containing ring.

As used herein, the term "π electron-depleted nitrogen-containing ring" indicates a $C_1$-$C_{60}$ heterocyclic group having at least one *—N=*' moiety as a ring-forming moiety.

For example, the "π electron-depleted nitrogen-containing ring" may be i) a 60-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but are not limited thereto.

For example, the electron transport region may include a compound represented by Formula 601:

$$[Ar_{601}]_{xe11}\text{-}[(L_{601})_{xe1}\text{-}R_{601}]_{xe21}. \qquad \text{Formula 601}$$

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{00}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In one embodiment, at least one of $Ar_{601}$(S) in the number of xe11 and $R_{601}$(s) in the number of xe21 may include the π electron-depleted nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar601(s) may be linked via a single bond.

In one or more embodiments, $Ar_{601}$ in Formula 601 may be an anthracene group.

In one or more embodiments, the compound represented by 601 may be represented by Formula 601-1:

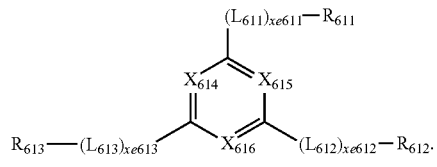

Formula 601-1

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, in Formulae 601 and 601-1, xe1 and xe611 to xe613 may each independently be 0, 1, or 2.

In one or more embodiments, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ may each independently be the same as described above.

The electron transport region may include at least one compound selected from Compounds ET1 to ET36, but embodiments of the present disclosure are not limited thereto:

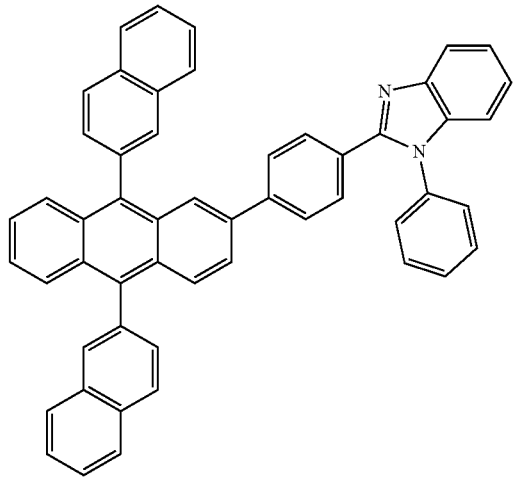

ET1

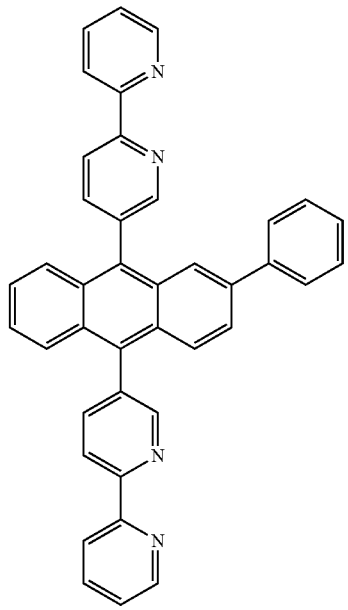

ET2

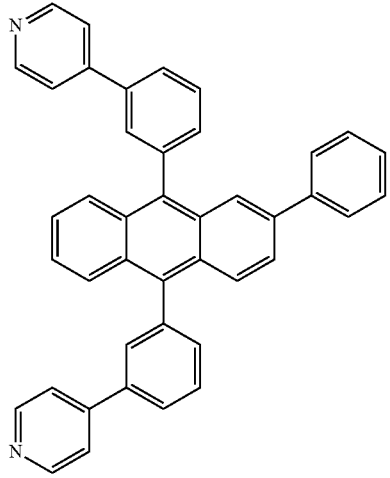

ET3

-continued
ET4
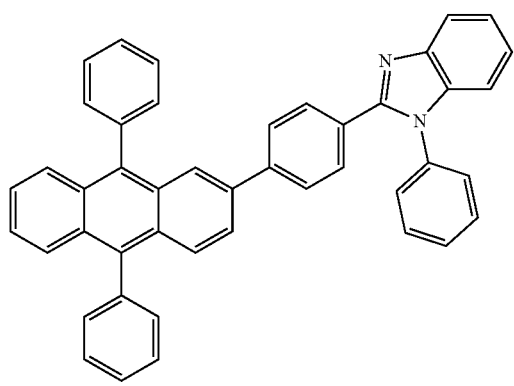
ET5
ET6
-continued
ET7
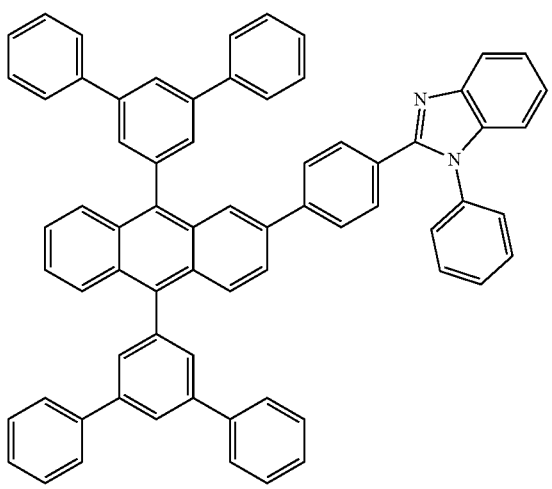
ET8
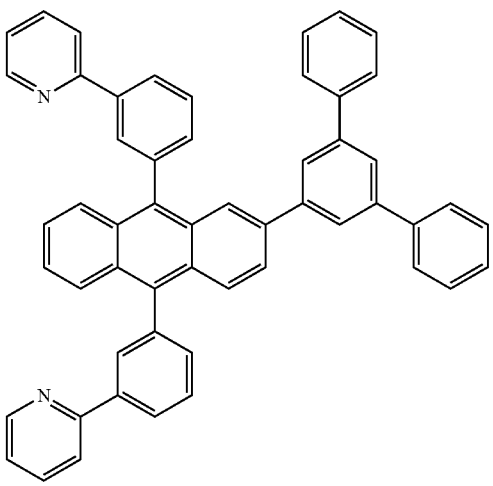
ET9
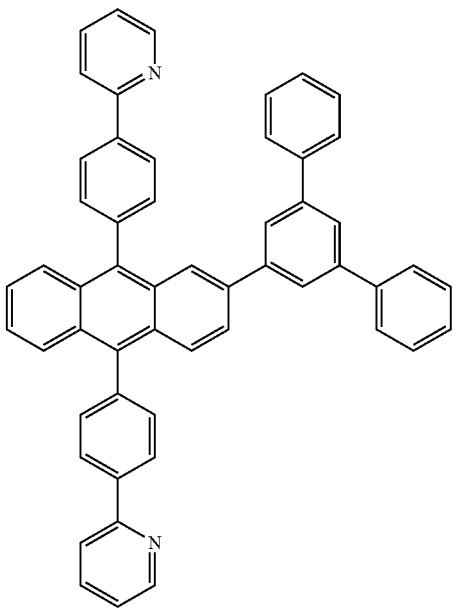

ET10
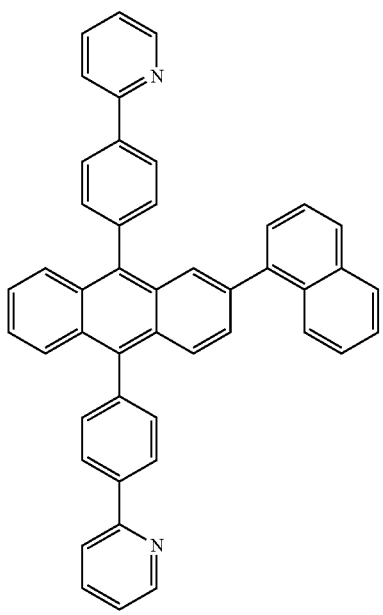
ET11
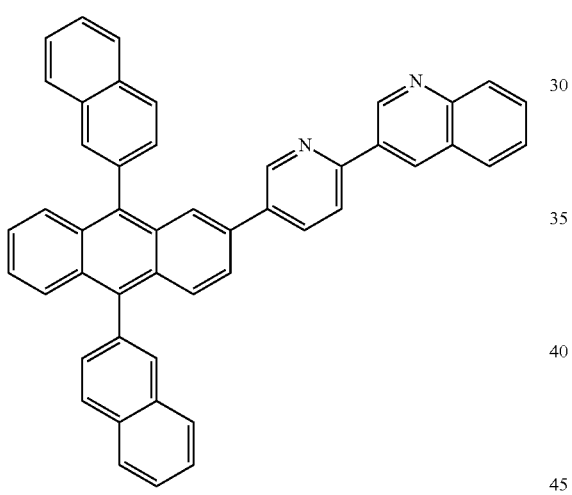
ET12
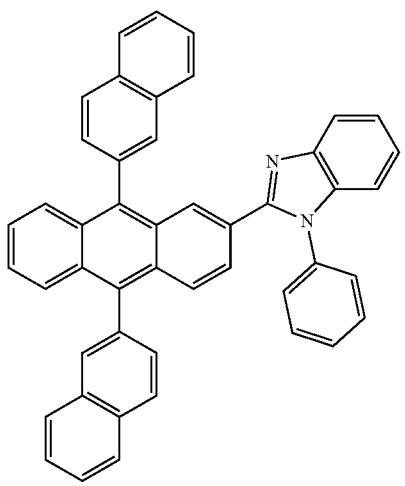
ET13
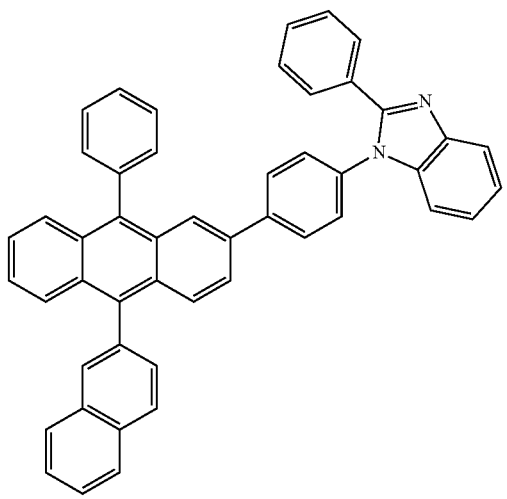
ET14
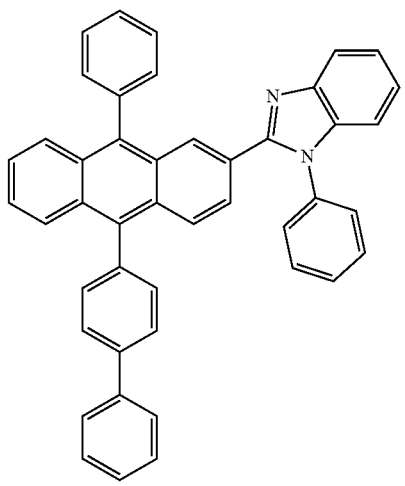
ET15
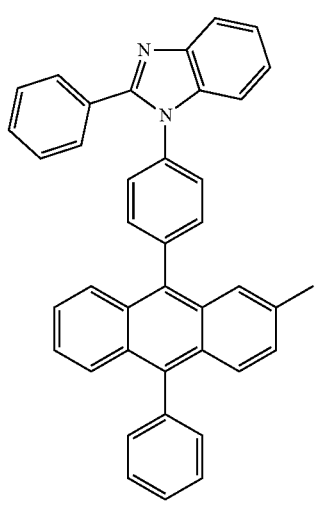

ET16
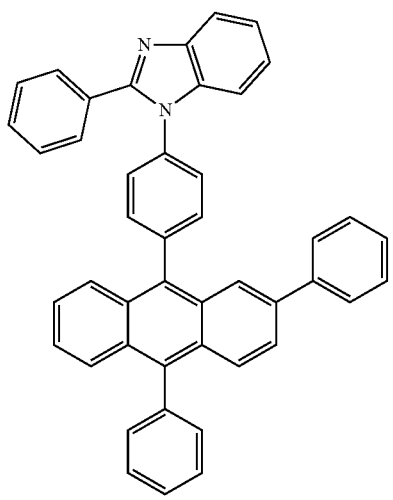
ET19
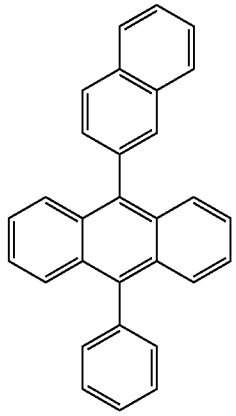
ET17
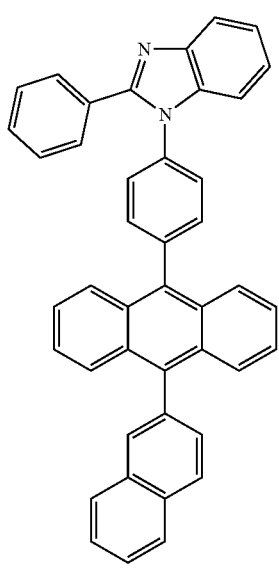
ET20
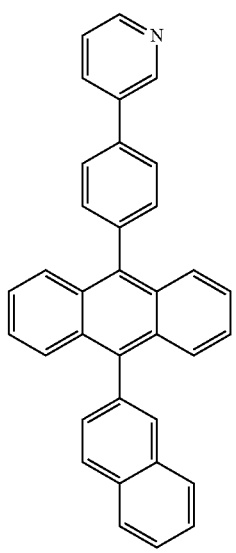
ET18
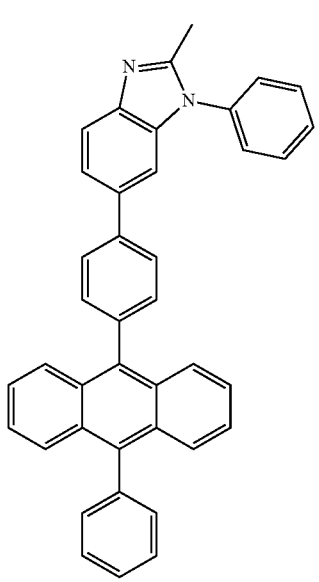
ET21
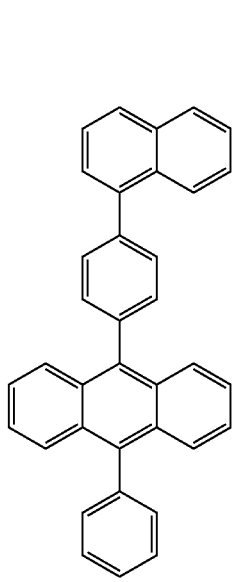

ET22
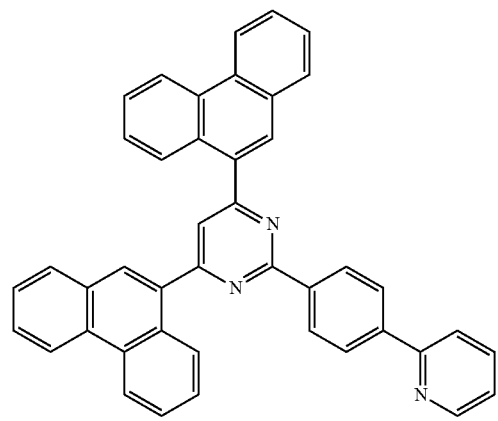
ET23
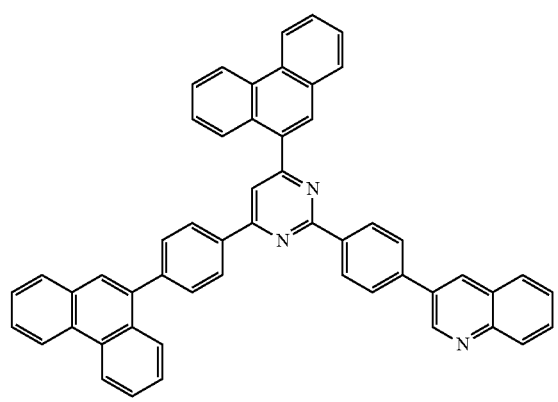
ET24
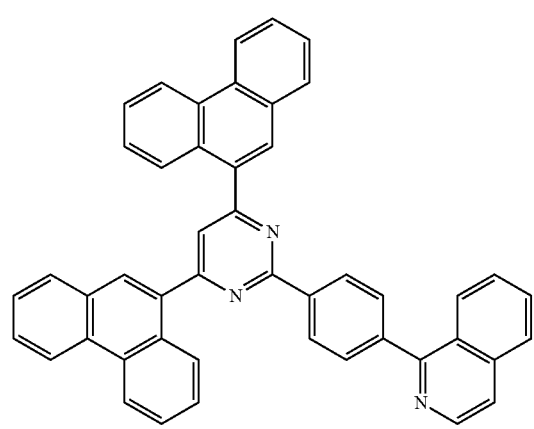
ET25
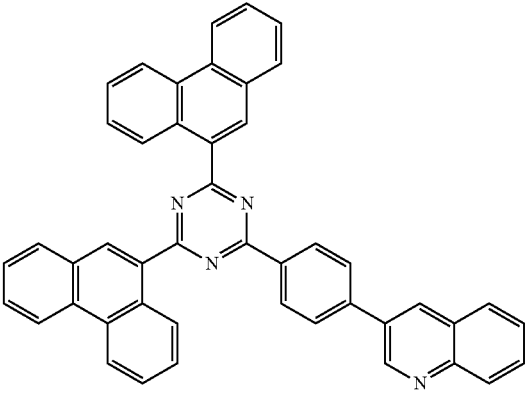
ET26
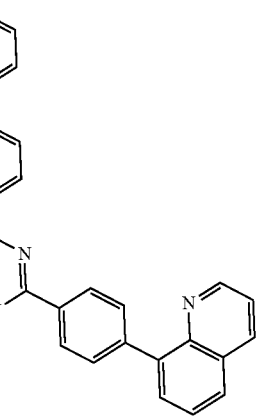
ET27
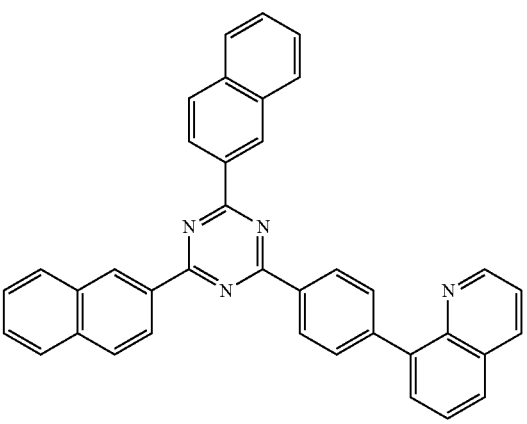
ET28
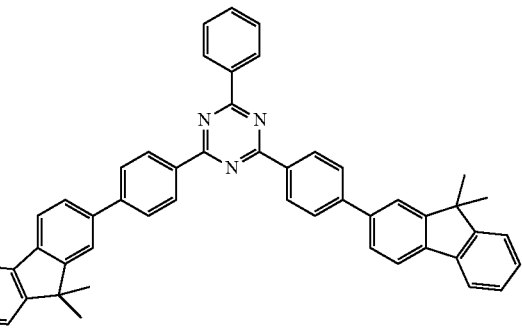

ET29
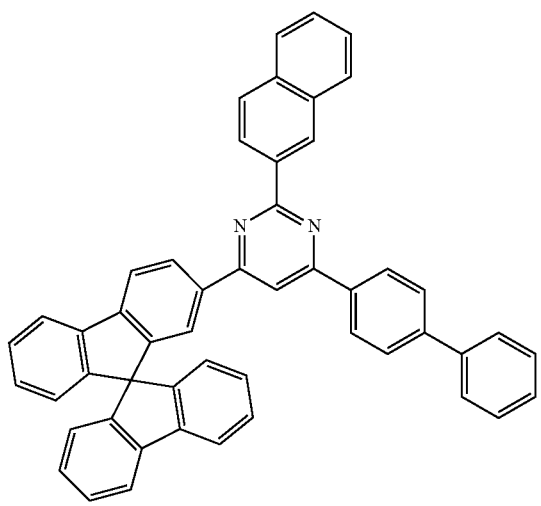
ET32
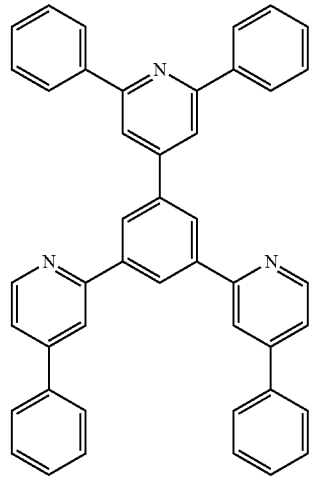
ET30
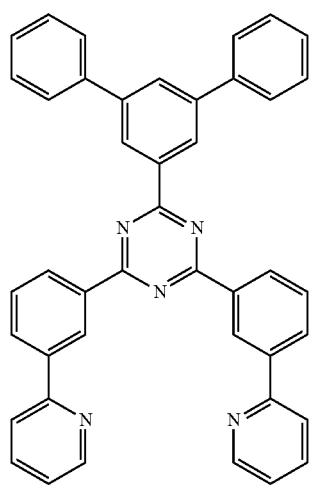
ET33
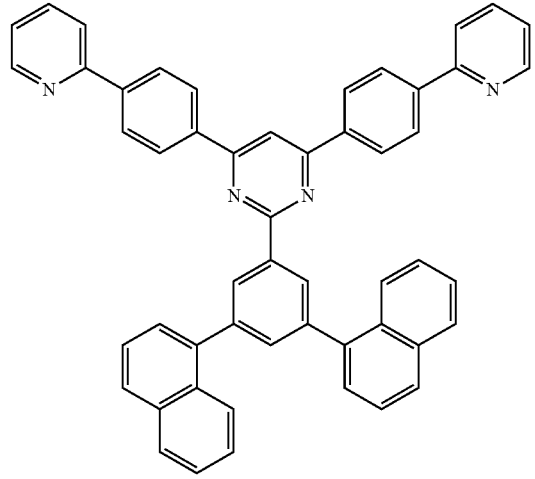
ET31
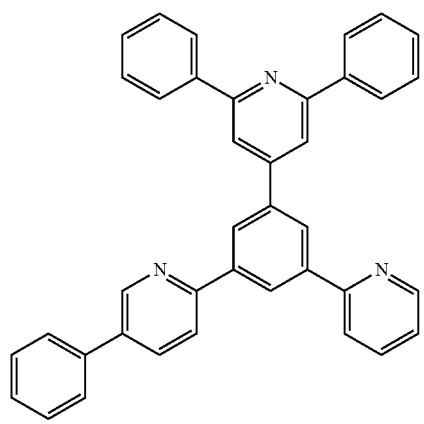
ET34
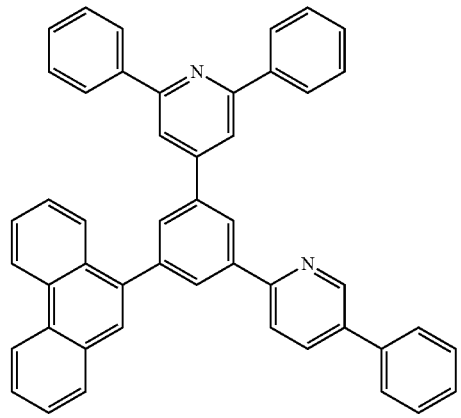

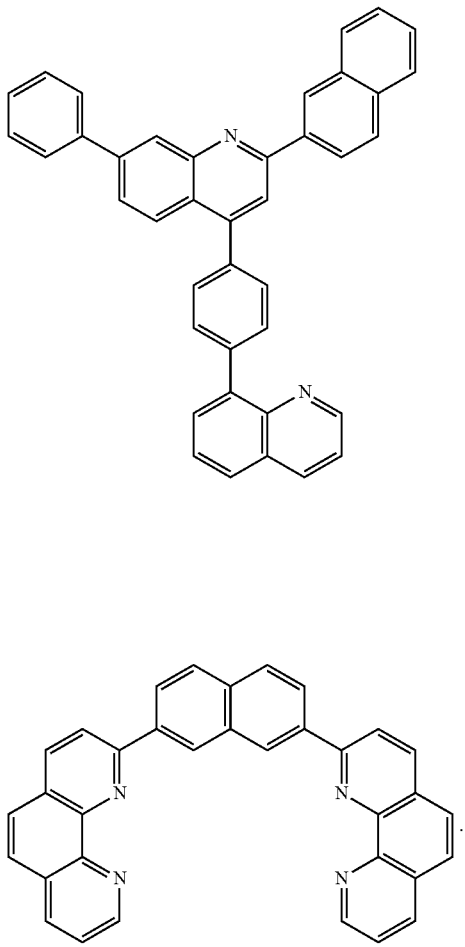

ET35

ET36

Alq₃

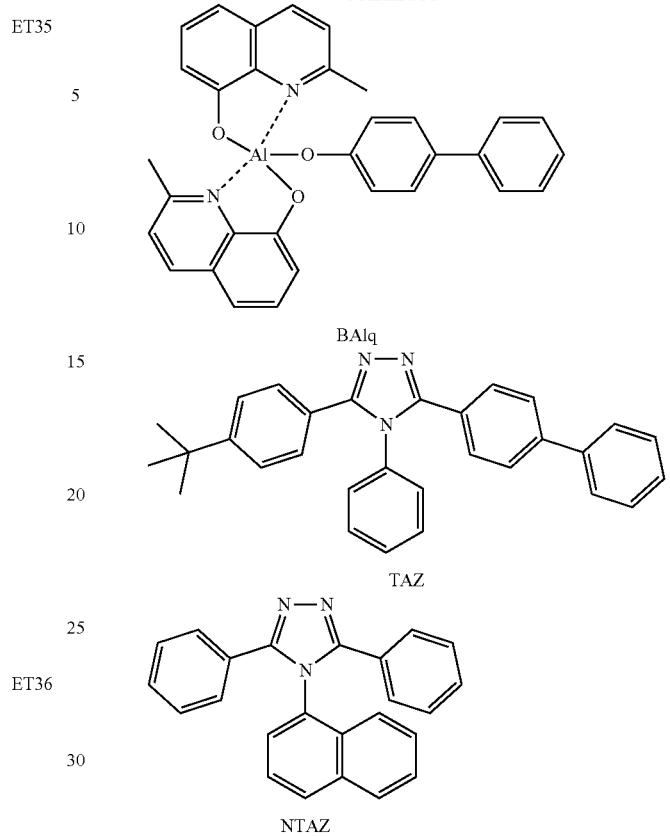

BAlq

TAZ

NTAZ

In one or more embodiments, the electron transport region may include at least one selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have suitable or satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2.

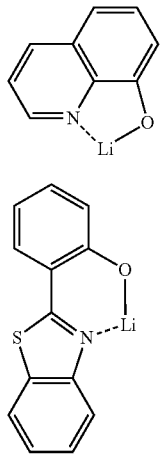

ET-D1

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, or Cs. In one or more embodiments, the alkali metal may be Li or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}O$ (0<x<1), $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have suitable or satisfactory electron injection characteristics without a substantial increase in driving voltage.

Second Electrode 190

The second electrode 190 may be on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 2:
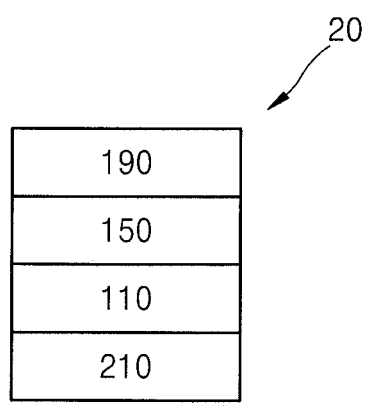
FIG. 2 is a schematic cross-sectional view of an organic light-emitting device according to another embodiment.
Figure 3:
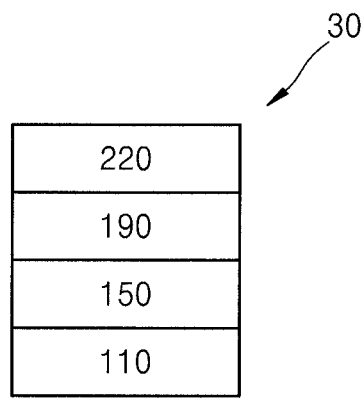
FIG. 3 is a schematic cross-sectional view of an organic light-emitting device according to another embodiment.
Figure 4:
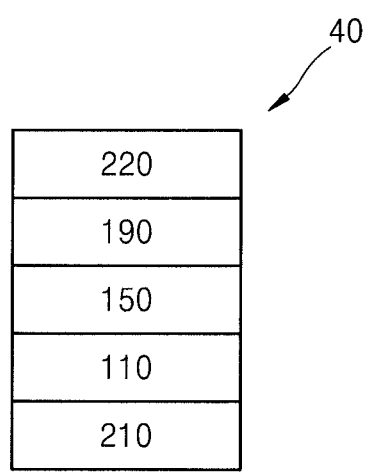
FIG. 4 is a schematic cross-sectional view of an organic light-emitting device according to another embodiment.

Description of FIGS. 2-4

An organic light-emitting device 20 of FIG. 2 includes a first capping layer 210, a first electrode 110, an organic layer 150, and a second electrode 190 which are sequentially stacked in this stated order, an organic light-emitting device 30 of FIG. 3 includes a first electrode 110, an organic layer 150, a second electrode 190, and a second capping layer 220 which are sequentially stacked in this stated order, and an organic light-emitting device 40 of FIG. 4 includes a first capping layer 210, a first electrode 110, an organic layer 150, a second electrode 190, and a second capping layer 220.

Regarding FIGS. 2-4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescence efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, a naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

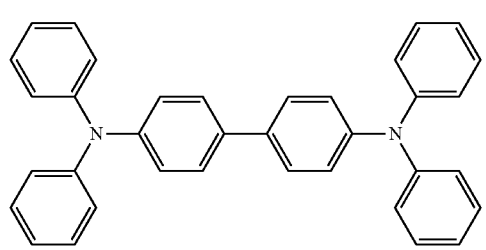
CP1

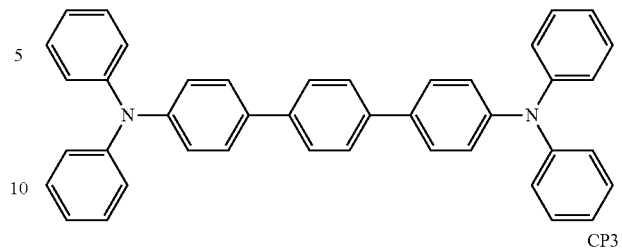
CP2

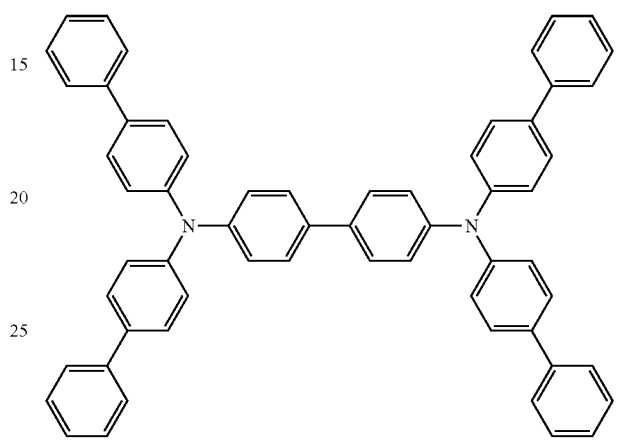
CP3

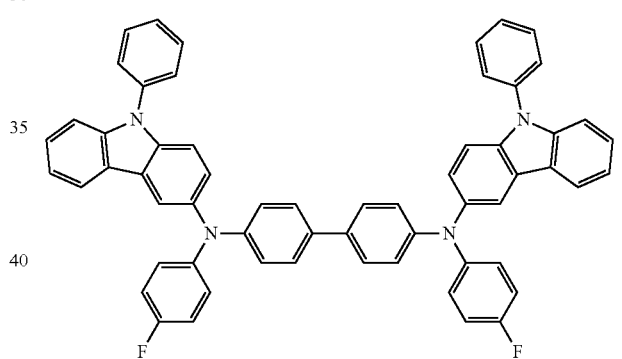
CP4

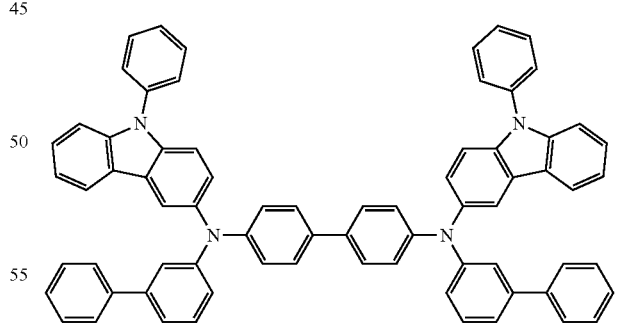
CP5

Hereinbefore, the organic light-emitting device according to an embodiment has been described in connection with FIGS. 1-4. However, embodiments of the present disclosure are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about 10-3 torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed, and the structure of a layer to be formed.

General Definition of Some of the Substituents

The term "$C_1$-$C_{60}$ alkyl group," as used herein, refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminus of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminus of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., ring and/or group is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 1 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group," as used herein, indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

The term "$C_1$-$C_{60}$ heteroaryloxy group," as used herein, indicates —$OA_{104}$ (wherein $A_{104}$ is the $C_1$-$C_{60}$ heteroaryl group), and the term "$C_6$-$C_{60}$ heteroarylthio group," as used herein, indicates —$SA105$ (wherein $A_{105}$ is the $C_1$-$C_{60}$ heteroaryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire molecule is not aromatic). An example of the monovalent non-aromatic condensed polycyclic group is a fluorenyl group. The term "divalent non-aromatic condensed polycyclic group,"

as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire molecule is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_5$-$C_{60}$ carbocyclic group, except that as a ring-forming atom, at least one heteroatom selected from N, O, Si, P, and S is used in addition to carbon (the number of carbon atoms may be in a range of 1 to 60).

At least one selected from substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{00}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ hetero aryloxy group, the substituted $C_1$-$C_{60}$ hetero arylthio group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, a biphenyl group, and a terphenyl group.

The term "Ph," as used herein, represents a phenyl group, the term "Me," as used herein, represents a methyl group, the term "Et," as used herein, represents an ethyl group, the term "ter-Bu" or "Bu$^t$," as used herein, represents a tert-butyl group, and the term "OMe," as used herein, represents a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *', as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical molar equivalent of B was used in place of A.

EXAMPLES

Synthesis Example 1: Synthesis of Compound 3

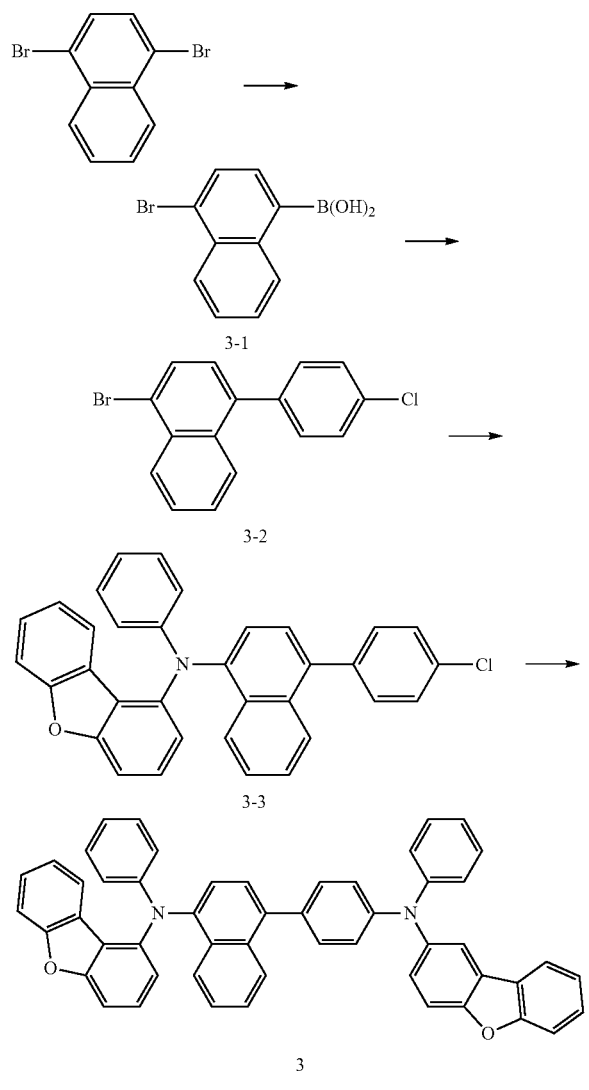

(1) Synthesis of Intermediate 3-1

1,4-dibromonaphthalene (2.86 g) was diluted with tetrahydrofuran (THF) (50 mL) and cooled to a temperature of −78° C. n-BuLi (2.5M in hexane, 4.3 mL) was slowly added dropwise thereto. After the reaction mixture was stirred for 1 hour while maintaining the temperature thereof, trimethyl borate (1.1 g) was added thereto and heated to room temperature. When the reaction was completed after stirring at room temperature for 15 hours, 12N HCl (1 mL) was added dropwise thereto and stirred again for 1 hour. An organic layer extracted therefrom there times by using diethyl ether was dried by using $MgSO_4$, filtered under reduced pressure, and distilled under reduced pressure. The residue obtained therefrom was washed by using hexane to obtain Intermediate 3-1 (2.1 g, 82%).

$C_{10}H_8BBrO_2$ [M]+ Calcd. 249.98 Found 249.98.

(2) Synthesis of Intermediate 3-2

Intermediate 3-1 (2.1 g), 1-bromo-4-chlorobenzene (2.8 g), $Pd(PPh_3)_4$(570 mg), $K_2CO_3$ (4.1 g) were diluted with THF (20 mL) and water (5 ml) and stirred at a temperature of 65° C. for 4 hours under reflux. After the reaction was completed, the reaction product was cooled to room temperature. An organic layer extracted therefrom three times by using diethyl ether was dried by using $MgSO_4$, filtered under reduced pressure, and distilled under reduced pressure. The residue obtained therefrom was separated and purified by column chromatography to obtain Intermediate 3-2 (2.5 g, %).

$C_{16}H_{10}Br_2$ [M]+ Calcd. 359.91 Found 359.93.

(3) Synthesis of Intermediate 3-3

Intermediate 3-2 (2.5 g) and N-phenyldibenzo[b,d]furan-1-amine (2.6 g) were diluted with toluene (30 mL), and $Pd_2(dba)_3$ (368 mg), $P(t-Bu)_3$ (0.250 ml), and NaOtBu (3 g) were sequentially added dropwise thereto. The reaction mixture was stirred at a temperature of 100° C. for 1 hour under reflux. After the reaction was completed, the reaction product was cooled to room temperature, and the reaction was terminated with water. An organic layer extracted therefrom three times by using diethyl ether was dried by using $MgSO_4$, filtered under reduced pressure, and distilled under reduced pressure. The residue obtained therefrom was separated and purified by column chromatography to obtain Intermediate 3-3 (3.6 g, 90%).

$C_{16}H_{10}BrCl$ [M]+ Calcd. 495.14 Found 495.16.

(4) Synthesis of Intermediate 3

Compound 3 (3.9 g, 75%) was obtained in substantially the same manner as in Intermediate 3-3, except that Intermediate 3-3 was used instead of Intermediate 3-2 and N-phenyldibenzo[b,d]furan-2-amine was used instead of N-phenyldibenzo[b,d]furan-1-amine.

Synthesis Example 2: Synthesis of Compound 6

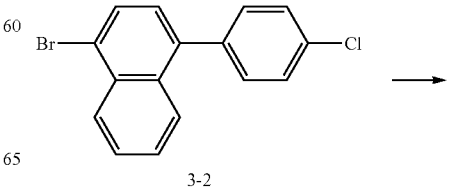

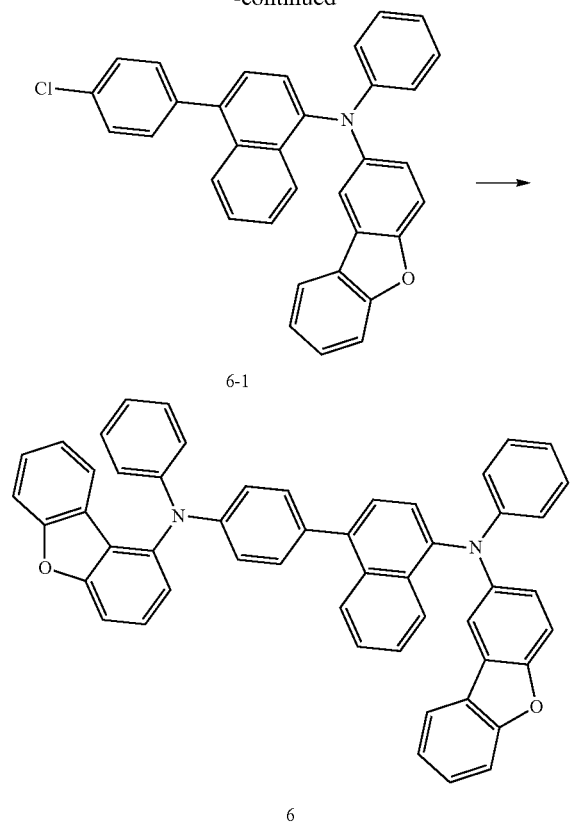

6-1

6

(1) Synthesis of Intermediate 6-1

Intermediate 6-1 (4.3 g, 82%) was obtained in substantially the same manner as in Intermediate 3-3, except that N-phenyldibenzo[b,d]furan-2-amine was used instead of N-phenyldibenzo[b,d]furan-1-amine.
$C_{34}H_{22}ClO$ [M]+ Calcd. 495.14 Found 495.16.

(2) Synthesis of Compound 6

Compound 6 (3.8 g, 61%) was obtained in substantially the same manner as in Intermediate 3-3, except that Intermediate 6-1 was used instead of Intermediate 3-2.

Synthesis Example 3: Synthesis of Compound 7

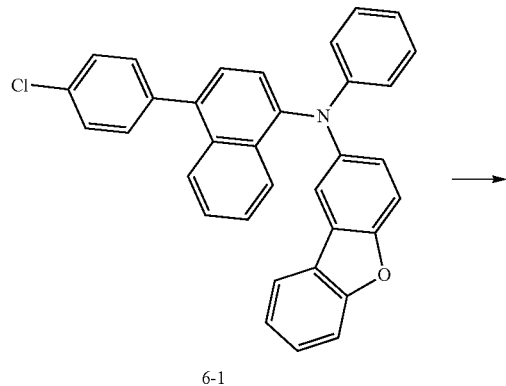

6-1

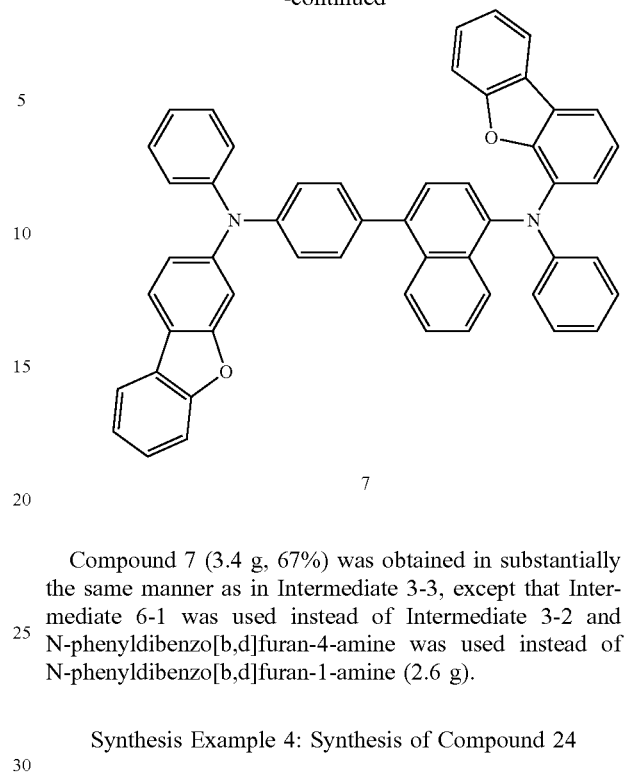

7

Compound 7 (3.4 g, 67%) was obtained in substantially the same manner as in Intermediate 3-3, except that Intermediate 6-1 was used instead of Intermediate 3-2 and N-phenyldibenzo[b,d]furan-4-amine was used instead of N-phenyldibenzo[b,d]furan-1-amine (2.6 g).

Synthesis Example 4: Synthesis of Compound 24

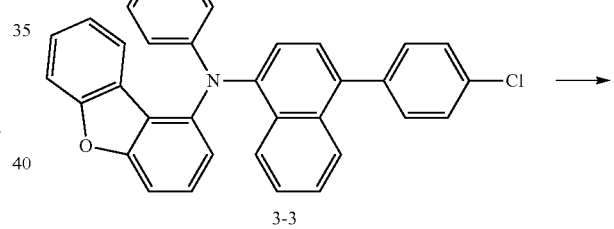

3-3

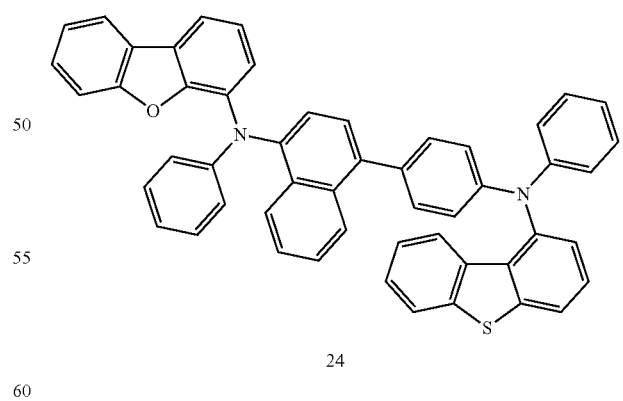

24

Compound 24 (3.8 g, 76%) was obtained in substantially the same manner as in Intermediate 3-3, except that Intermediate 3-3 was used instead of Intermediate 3-2 and N-phenyldibenzo[b,d]thiophene-1-amine was used instead of N-phenyldibenzo[b,d]furan-1-amine.

Synthesis Example 5: Synthesis of Compound 30

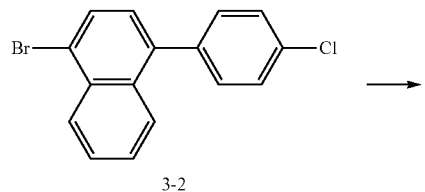

3-2

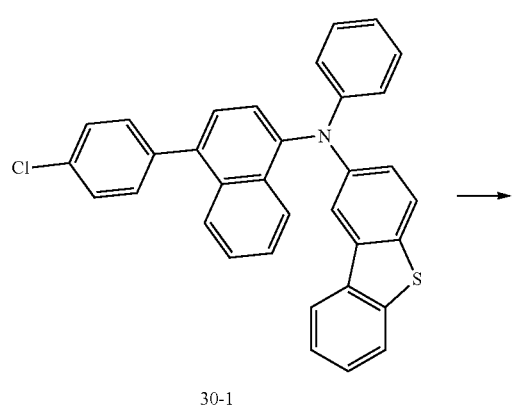

30-1

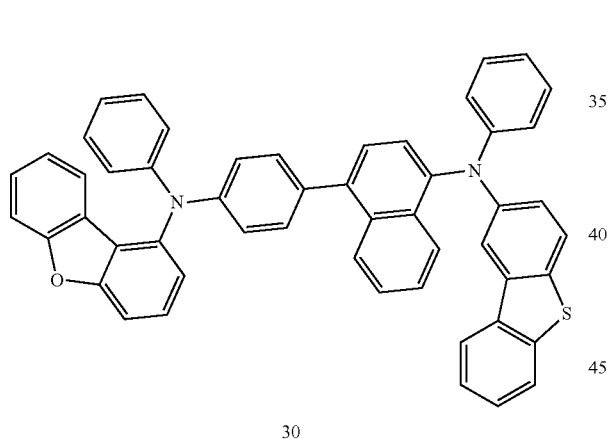

30

(1) Synthesis of Intermediate 30-1

Intermediate 30-1 (4 g, 78%) was obtained in substantially the same manner as in Intermediate 3-3, except that N-phenyldibenzo[b,d]thiophene-2-amine was used instead of N-phenyldibenzo[b,d]furan-1-amine.

$C_{34}H_{22}ClNS$ [M]+ Calcd. 511.12 Found 511.15.

(2) Synthesis of Compound 30

Compound 24 (4.1 g, 82%) was obtained in substantially the same manner as in Intermediate 3-3, except that Intermediate 30-1 was used instead of Intermediate 3-2.

Synthesis Example 6: Synthesis of Compound 42

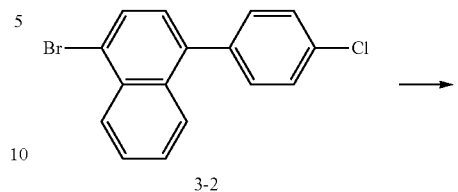

3-2

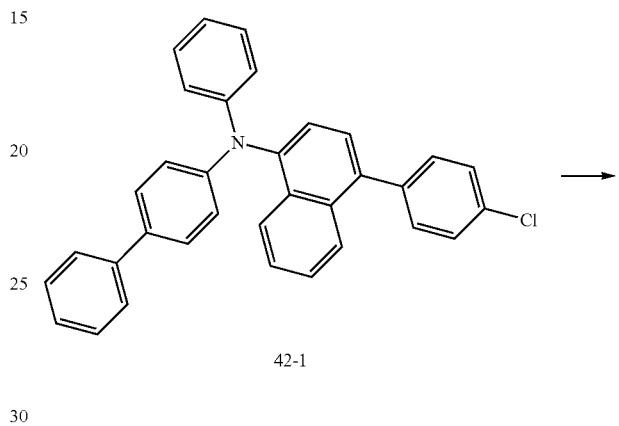

42-1

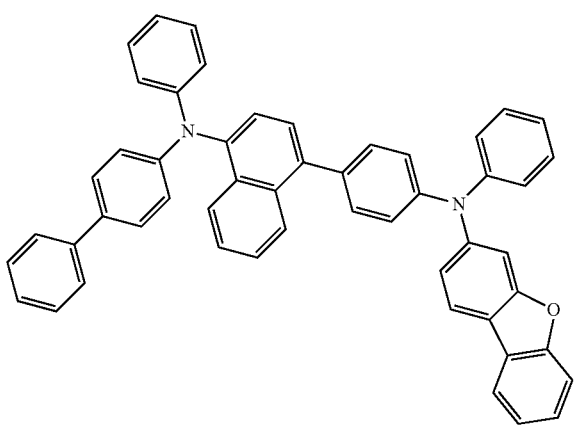

42

(1) Synthesis of Intermediate 42-1

Compound 42-1 (4.3 g, 89%) was obtained in substantially the same manner as in Intermediate 3-3, except that N-phenyl-[1,1'-biphenyl]-4-amine was used instead of N-phenyldibenzo[b,d]furan-1-amine.

$C_{34}H_{24}ClN$ [M]+ Calcd. 481.16 Found 481.17.

(2) Synthesis of Compound 42

Compound 42 (5.1 g, 82%) was obtained in substantially the same manner as in Intermediate 3-3, except that Intermediate 42-1 was used instead of Intermediate 3-2 and N-phenyldibenzo[b,d]furan-3-amine was used instead of N-phenyldibenzo[b,d]furan-1-amine.

Synthesis Example 7: Synthesis of Compound 43

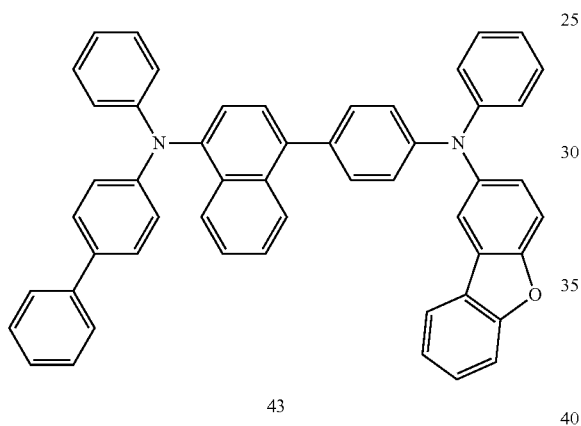

Compound 43 (5.4 g, 87%) was obtained in substantially the same manner as in Intermediate 3-3, except that Intermediate 42-1 was used instead of Intermediate 3-2 and N-phenyldibenzo[b,d]furan-2-amine was used instead of N-phenyldibenzo[b,d]furan-1-amine.

Synthesis Example 8: Synthesis of Compound 64

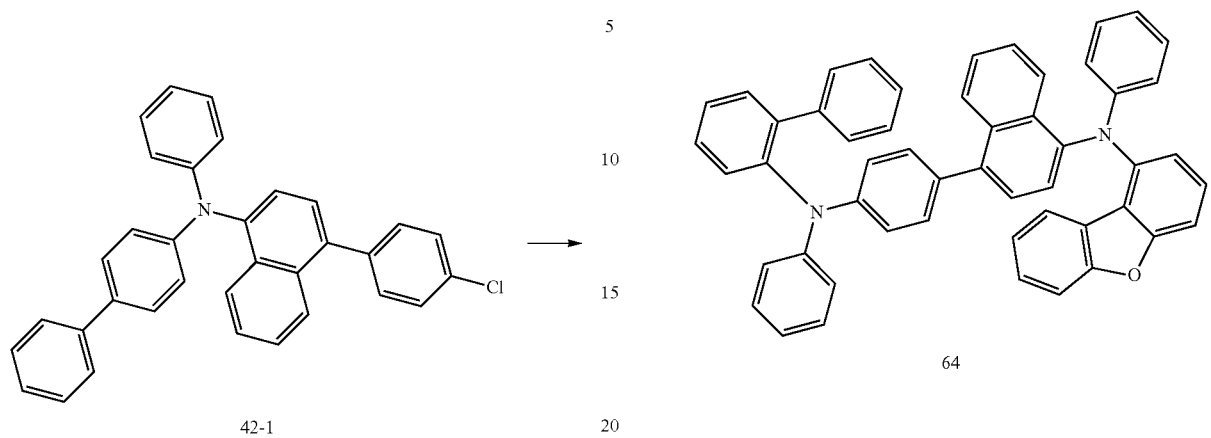

Compound 64 (3.9 g, 76%) was obtained in substantially the same manner as in Intermediate 3-3, except that Intermediate 3-3 was used instead of Intermediate 3-2 and N-phenyl-[1,1'-biphenyl]-2-amine was used instead of N-phenyldibenzo[b,d]furan-1-amine.

Synthesis Example 9: Synthesis of Compound 66

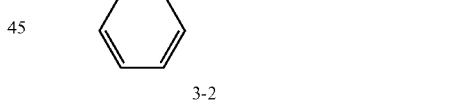

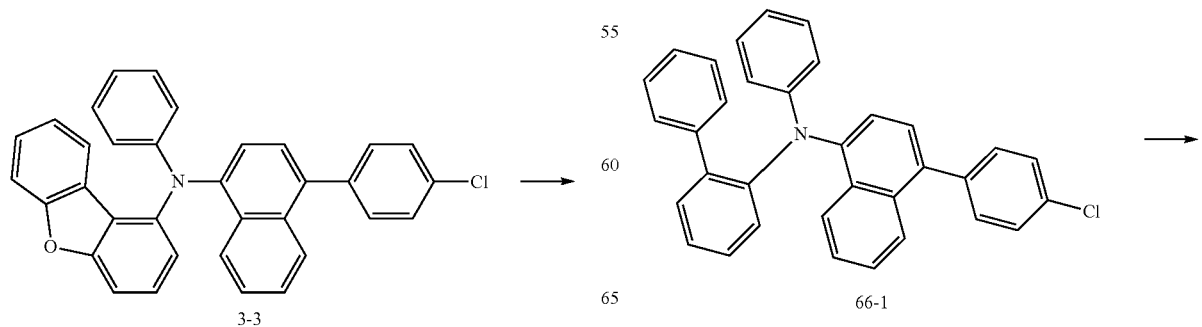

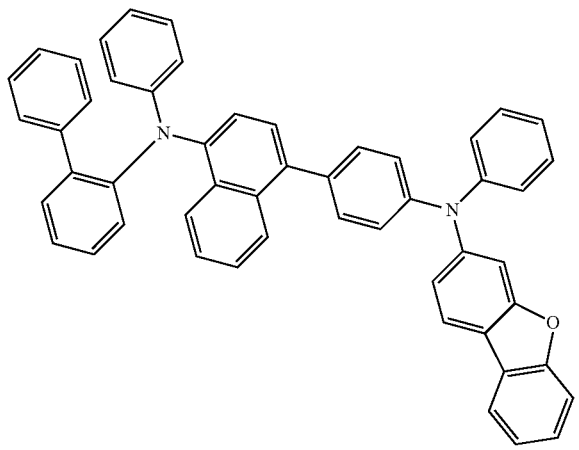

66

(1) Synthesis of Intermediate 66-1

Intermediate 66-1 (4 g, 83%) was obtained in substantially the same manner as in Intermediate 3-3, except that N-phenyl-[1,1'-biphenyl]-2-amine was used instead of N-phenyldibenzo[b,d]furan-1-amine.

$C_{34}H_{24}ClN$ [M]+ Calcd. 481.16 Found 481.17.

(2) Synthesis of Compound 66

Compound 66 (4.8 g, 82%) was obtained in substantially the same manner as in Intermediate 3-3, except that Intermediate 66-1 was used instead of Intermediate 3-2 and N-phenyldibenzo[b,d]furan-3-amine was used instead of N-phenyldibenzo[b,d]furan-1-amine.

$^1$H NMR and MS/FAB of Compounds synthesized according to Synthesis Examples 1 to 9 are shown in Table 1.

Methods of synthesizing compounds other than Compounds shown in Table 1 are recognizable by those of ordinary skill in the art by referring to the synthesis path and source materials described above.

TABLE 1

| Compound | $^1$H NMR (CDCl$_3$, 400 MHz) | MS/FAB Calcd. | Found |
|---|---|---|---|
| 3 | 8.95(d, 1H), 8.27(d, 1H), 8.22(s, 1H), 7.98(d, 2H), 7.61-7.53(m, 7H), 7.49-7.30(m, 9H), 7.25-6.98(m, 11H), 6.97(dd, 2H) | 718.27 | 718.26 |
| 6 | 8.95(d, 1H), 8.27(d, 1H), 8.22(s, 1H), 7.98(d, 2H), 7.61-7.30(m, 16H), 7.25-7.08(9H), 7.00-6.92(m, 4H) | 718.27 | 718.26 |
| 7 | 8.95(d, 1H), 8.27(d, 1H), 8.03(s, 1H), 7.98(dd, 2H), 7.90(d, 1H), 7.65-7.27(m, 16H), 7.24-6.93(m, 12H) | 718.28 | 718.26 |
| 24 | 8.95(d, 1), 8.45(d, 1H), 8.27(d, 1H), 8(m, 2H), 7.65-7.22(m, 22H), 7.08-6.96(m, 7H) | 734.26 | 734.24 |
| 30 | 8.95(d, 1), 8.45(d, 1H), 8.27(d, 1H), 7.98-7.90(m, 3H), 7.85(d, 1H). 7.64-7.18(m, 20H), 7.08(m, 4H), 7.00(t, 2H), 6.91(d, 1H) | 734.25 | 734.24 |
| 42 | 8.95(d, 1), 8.27(d, 1H), 8.03(s, 1)H, 7.98(d, 1H), 7.80(d, 1H). 7.75(m, 2H), 7.61-7.18(m, 22H), 7.08(d, 3H), 7.00(t, 2H). 6.91(d, 1H) | 704.27 | 704.28 |
| 43 | 8.95(d, 1), 8.27(d, 1H), 8.22(s, 1)H, 7.98(d, 1H), 7.75(d, 2H). 7.61-7.18(m, 23H), 7.08-6.95(m, 7H) | 704.29 | 704.28 |
| 64 | 8.95(d, 1H), 8.28(d, 1H). 8.10(d, 1H). 7.98(d, 1H), 7.61-7.20(m, 22H), 7.08(m, 5H), 7.00(t, 2H). 7.91(d, 1H) | 704.28 | 704.28 |
| 66 | 8.95(d, 1H), 8.27(d, 1H). 8.10(d, 1H). 8.03(s, 1H), 7.98(d, 1H), 7.80(d, 1H), 7.61(d, 1H). 7.55-7.30(m, 15H), 7.24-7.20(m, 4H), 7.14(m, 1H). 7.08-7.00(m, 8H), 6.91(d, 1H) | 704.29 | 704.28 |

Example 1

As an anode, an ITO glass substrate (15 Ω/cm², 1,200 Å) was cut to a size of 50 mm×50 mm×0.7 mm, sonicated with isopropyl alcohol and pure water each for 5 minutes, and then cleaned by exposure to ultraviolet rays and ozone for 30 minutes. Then, the ITO glass substrate was provided to a vacuum deposition apparatus.

2-TNATA was vacuum-deposited on the ITO glass substrate to form a hole injection layer having a thickness of 600 Å, and Compound 3 was vacuum-deposited on the hole injection layer to form a hole transport layer having a thickness of 300 Å.

9,10-di-naphthalene-2-yl-anthracene (ADN) (blue fluorescent host) and DPAVBi (blue fluorescent dopant) were co-deposited on the hole transport layer at a weight ratio 98:2 to form an emission layer having a thickness of 300 Å.

Then, Alq$_3$ was deposited on the emission layer to form an electron transport layer having a thickness of 300 Å, LiF was deposited on the electron transport layer to form an electron injection layer having a thickness of 10 Å, and Al was deposited on the electron injection layer to form a cathode having a thickness of 3,000 Å, thereby completing the manufacture of an organic light-emitting device.

Examples 2 to 9 and Comparative Examples 1 to 3

Organic light-emitting layers were manufactured in substantially the same manner as in Example 1, except that Compounds shown in Table 2 were each used instead of Compound 3 in forming a hole transport layer.

Evaluation Example

The driving voltage, luminance, efficiency, and lifespan of the organic light-emitting devices manufactured according to Examples 1 to 9 and Comparative Examples 1 to 3 were measured at a current density 10 mA/cm² by using Keithley SMU 236 and a luminance meter PR650, and results thereof are shown in Table 2. The lifespan indicates an amount of time that lapsed when luminance was 50% of initial luminance (100%) after the organic light-emitting device was driven at a current density 100 mA/cm².

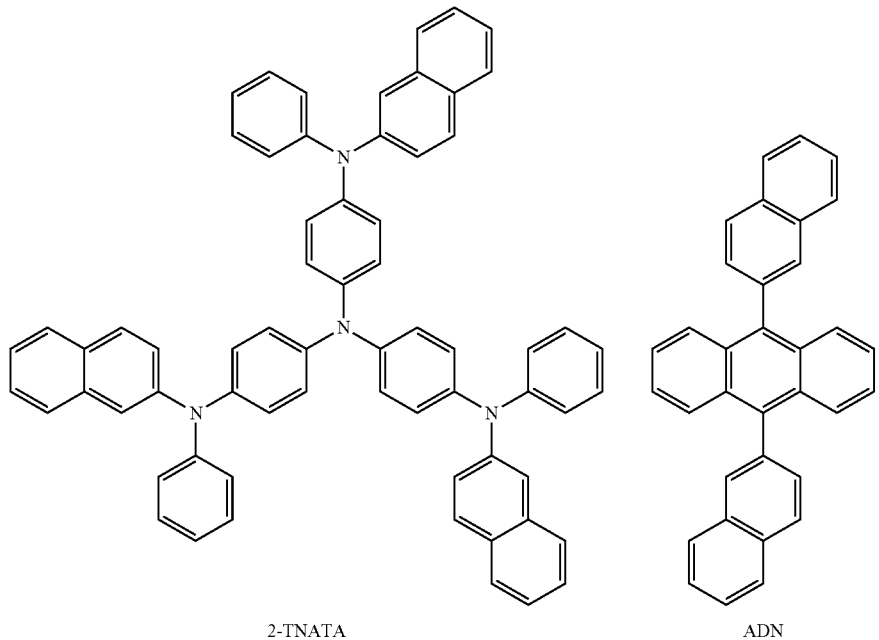

2-TNATA      ADN

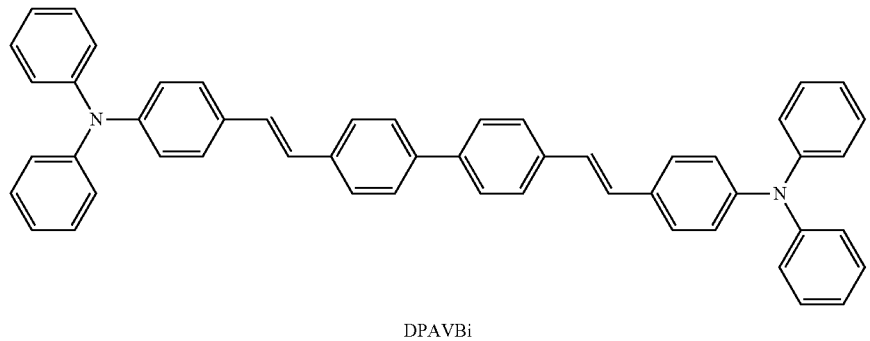

DPAVBi

TABLE 2

| | Material for hole transport layer | Driving voltage (V) | Current density (mA/cm$^2$) | Luminance (cd/m$^2$) | Efficiency (cd/A) | Emission color | Half lifespan (hr @ 100 mA/cm$^2$) |
|---|---|---|---|---|---|---|---|
| Comparative Example 1 | NPB | 7.01 | 50 | 2645 | 5.29 | Blue | 258 |
| Comparative Example 2 | Compound A | 5.42 | 50 | 3010 | 6.02 | Blue | 299 |
| Comparative Example 3 | Compound B | 5.62 | 50 | 2970 | 5.94 | Blue | 301 |
| Example 1 | Compound 3 | 4.45 | 50 | 3440 | 6.88 | Blue | 325 |
| Example 2 | Compound 6 | 4.20 | 50 | 3750 | 7.50 | Blue | 320 |
| Example 3 | Compound 7 | 4.32 | 50 | 3603 | 7.21 | Blue | 362 |
| Example 4 | Compound 42 | 4.36 | 50 | 3572 | 7.14 | Blue | 384 |
| Example 5 | Compound 24 | 4.46 | 50 | 3345 | 6.69 | Blue | 364 |
| Example 6 | Compound 30 | 4.32 | 50 | 3420 | 6.84 | Blue | 364 |
| Example 7 | Compound 43 | 4.34 | 50 | 3521 | 7.04 | Blue | 353 |
| Example 8 | Compound 64 | 4.34 | 50 | 3412 | 6.82 | Blue | 346 |
| Example 9 | Compound 66 | 4.41 | 50 | 3542 | 7.08 | Blue | 358 |

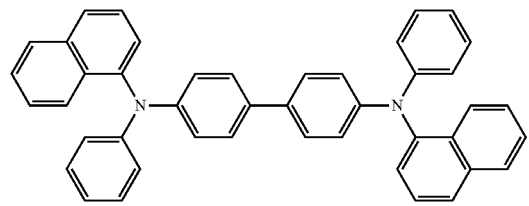

NPB

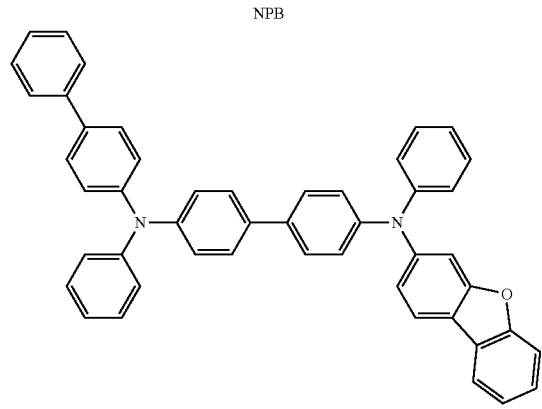

A

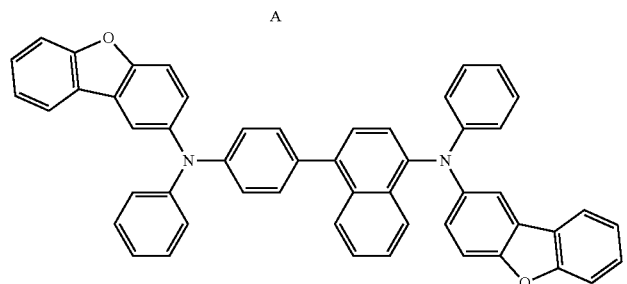

B

TABLE 2-continued
| Material for hole transport layer | Driving voltage (V) | Current density (mA/cm$^2$) | Luminance (cd/m$^2$) | Efficiency (cd/A) | Emission color | Half lifespan (hr @ 100 mA/cm$^2$) |
| --- | --- | --- | --- | --- | --- | --- |
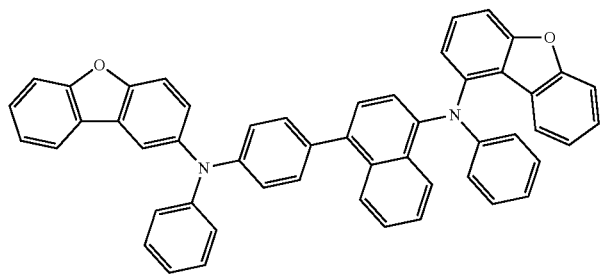
3
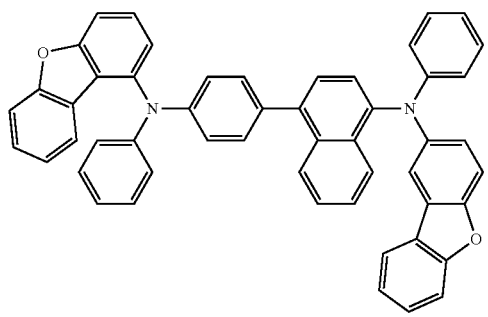
6
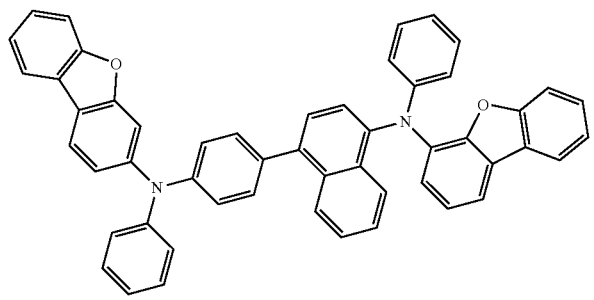
7
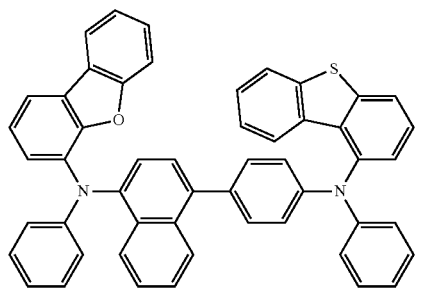
24

TABLE 2-continued
| Material for hole transport layer | Driving voltage (V) | Current density (mA/cm$^2$) | Luminance (cd/m$^2$) | Efficiency (cd/A) | Emission color | Half lifespan (hr @ 100 mA/cm$^2$) |
| --- | --- | --- | --- | --- | --- | --- |
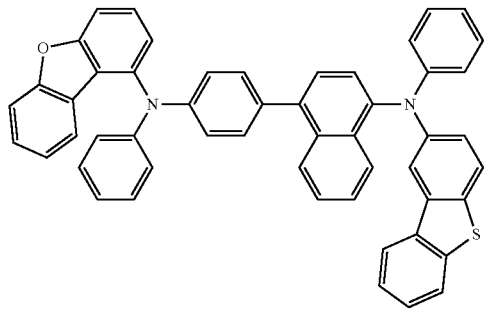
30
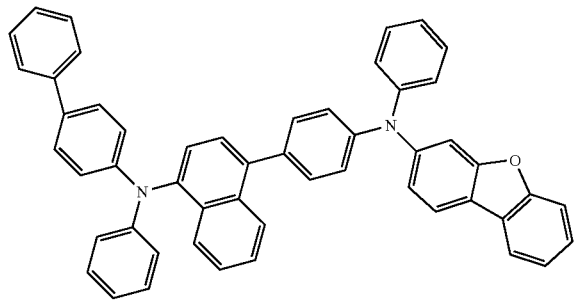
42
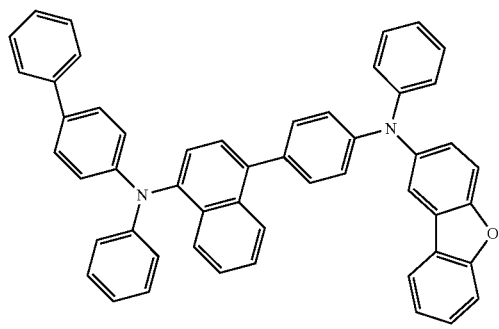
43
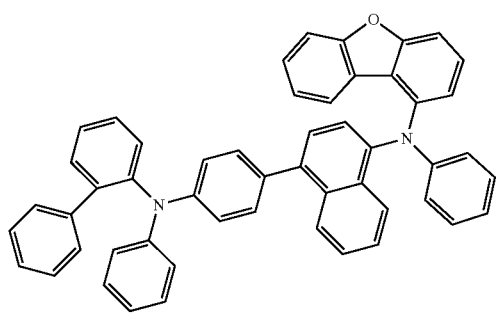
64

TABLE 2-continued

| Material for hole transport layer | Driving voltage (V) | Current density (mA/cm$^2$) | Luminance (cd/m$^2$) | Efficiency (cd/A) | Emission color | Half lifespan (hr @ 100 mA/cm$^2$) |
| --- | --- | --- | --- | --- | --- | --- |

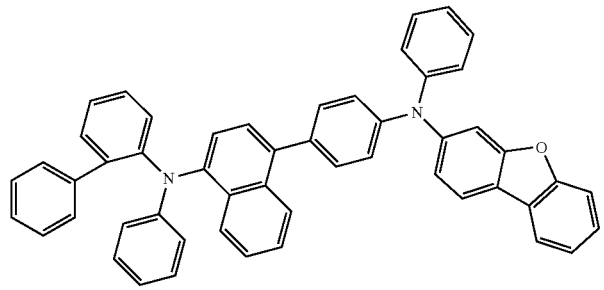

66

Referring to Table 2, it is confirmed that the organic light-emitting devices of Examples 1 to 9 have a low driving voltage, high luminance, and high efficiency, as compared with the organic light-emitting devices of Comparative Examples 1 to 3. For example, it is confirmed that the organic light-emitting devices of Examples 1 to 9 have a remarkably improved lifespan, as compared with the organic light-emitting devices of Comparative Examples 1 to 3.

The organic light-emitting device including the diamine compound may have a low driving voltage, high efficiency, high luminance, high color purity, and a long lifespan.

It should be understood that embodiments described herein should be considered in a descriptive sense only and not for purposes of limitation. Descriptions of features or aspects within each embodiment should typically be considered as available for other similar features or aspects in other embodiments.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

While one or more embodiments have been described with reference to the figures, it will be understood by those of ordinary skill in the art that various changes in form and details may be made therein without departing from the spirit and scope of the present disclosure as defined by the following claims, and equivalents thereof.

What is claimed is:

1. An organic light-emitting device comprising:
   a first electrode;
   a second electrode; and
   an organic layer between the first electrode and the second electrode and comprising an emission layer,
   wherein the organic layer further comprises a hole transport region between the first electrode and the emission layer, and
   the hole transport region comprises the diamine compound represented by Formula 1-4:

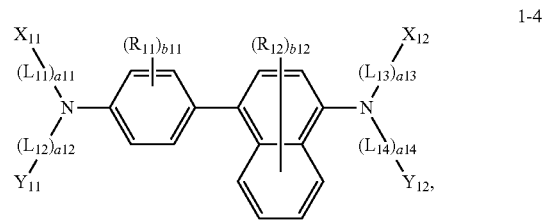

1-4

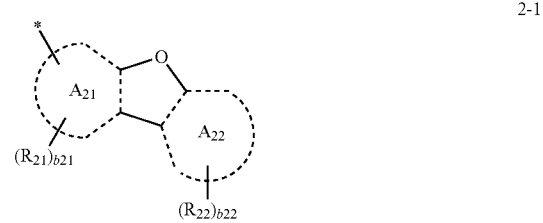

2-1

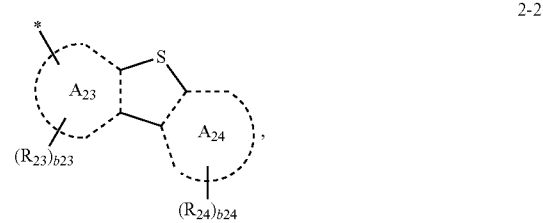

2-2 wherein, in Formula 1-4, $X_{11}$ and $X_{12}$ are each independently represented by one selected from Formulae 2-1 and 2-2, wherein $X_{11}$ and $X_{12}$ are different from each other, and a binding site of Formulae 2-1 or 2-2 in $X_{11}$ and a binding site of Formulae 2-1 or 2-2 in $X_{12}$ are different from each other, $Y_{11}$ and $Y_{12}$ are each independently selected from:

a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group; and a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group, each substituted with at least one selected from deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, a butoxy group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, a phenanthrolinyl group, and —Si(Q$_1$)(Q$_2$)(Q$_3$), and $Q_1$ to $Q_3$ are each independently selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, a terphenyl group, and a naphthyl group, $L_{11}$ to $L_{14}$ are each independently selected from:

a single bond, a $C_6$-$C_{60}$ arylene group, a $C_1$-$C_{60}$ heteroarylene group, a biphenylene group, and a terphenylene group; and a $C_6$-$C_{60}$ arylene group, a $C_1$-$C_{60}$ heteroarylene group, a biphenylene group, and a terphenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si(Q$_1$)(Q$_2$)(Q$_3$), a11 to a14 are each independently selected from 0, 1, 2, and 3, $R_{11}$ and $R_{12}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si(Q$_1$)(Q$_2$)(Q$_3$), b11 is selected from 1, 2, 3, 4, 5, and 6, and b12 is selected from 1, 2, 3, and 4, wherein, in Formulae 2-1 and 2-2, $A_{21}$ to $A_{24}$ are each independently selected from a benzene group, a naphthalene group, an anthracene group, a phenanthrene group, a chrysene group, a pyrene group, a pentaphene group, a triphenylene group, and a phenylene group, b21 to b24 are each independently selected from 1, 2, 3, 4, 5, 6, 7, 8, 9, and 10, and $R_{21}$ to $R_{24}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si(Q$_1$)(Q$_2$)(Q$_3$), and wherein $Q_1$ to $Q_3$ are each independently selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group, and

* indicates a binding site to $L_{11}$, $L_{13}$, or N.

2. The organic light-emitting device of claim 1, wherein:

the hole transport region comprises at least one selected from a hole injection layer and a hole transport layer, and at least one selected from the hole injection layer and the hole transport layer comprises the diamine compound.

3. The organic light-emitting device of claim 1, wherein:
the hole transport region comprises a p-dopant, and
the p-dopant has a lowest unoccupied molecular orbital (LUMO) energy level of about −3.5 eV or less.

4. A diamine compound represented by Formula 1-4:

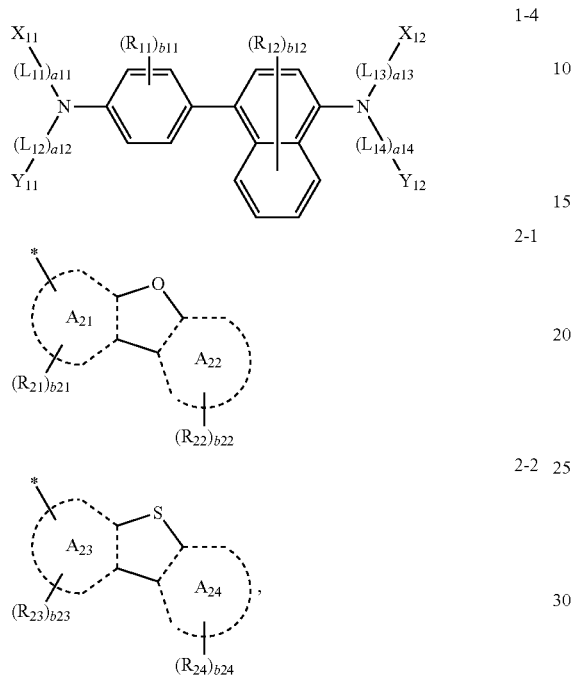

wherein, in Formula 1-4, $X_{11}$ and $X_{12}$ are each independently represented by one selected from Formulae 2-1 and 2-2, wherein $X_{11}$ and $X_{12}$ are different from each other, and a binding site of Formulae 2-1 or 2-2 in $X_{11}$ and a binding site of Formulae 2-1 or 2-2 in $X_{12}$ are different from each other, $Y_{11}$ and $Y_{12}$ are each independently selected from:

a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group; and a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group, each substituted with at least one selected from deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, a butoxy group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, a phenanthrolinyl group, and —Si(Q$_1$)(Q$_2$)(Q$_3$), and $Q_1$ to $Q_3$ are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, a terphenyl group, and a naphthyl group, $L_{11}$ to $L_{14}$ are each independently selected from:
a single bond, a C$_6$-C$_{60}$ arylene group, a C$_1$-C$_{60}$ heteroarylene group, a biphenylene group, and a terphenylene group; and a C$_6$-C$_{60}$ arylene group, a C$_1$-C$_{60}$ heteroarylene group, a biphenylene group, and a terphenylene group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkyl group substituted with at least one selected from deuterium, —F, and a cyano group, a C$_1$-C$_{20}$ alkoxy group, a C$_6$-C$_{60}$ aryl group, a C$_6$-C$_{60}$ aryl group substituted with at least one selected from deuterium, —F, and a cyano group, a C$_1$-C$_{60}$ heteroaryl group, a biphenyl group, a terphenyl group, and —Si(Q$_1$)(Q$_2$)(Q$_3$), a11 to a14 are each independently selected from 0, 1, 2, and 3, $R_{11}$ and $R_{12}$ are each independently selected from hydrogen, deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkyl group substituted with at least one selected from deuterium, —F, and a cyano group, a C$_1$-C$_{20}$ alkoxy group, a C$_6$-C$_{60}$ aryl group, a C$_6$-C$_{60}$ aryl group substituted with at least one selected from deuterium, —F, and a cyano group, a C$_1$-C$_{60}$ heteroaryl group, a biphenyl group, a terphenyl group, and —Si(Q$_1$)(Q$_2$)(Q$_3$), b11 is selected from 1, 2, 3, 4, 5, and 6, and
b12 is selected from 1, 2, 3, and 4,
wherein, in Formulae 2-1 and 2-2, $A_{21}$ to $A_{24}$ are each independently selected from a benzene group, a naphthalene group, an anthracene group, a phenanthrene group, a chrysene group, a pyrene group, a pentaphene group, a triphenylene group, and a phenylene group, b21 to b24 are each independently selected from 1, 2, 3, 4, 5, 6, 7, 8, 9, and 10, and $R_{21}$ to $R_{24}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si $(Q_1)(Q_2)(Q_3)$, wherein $Q_1$ to $Q_3$ are each independently selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group, and

* indicates a binding site to $L_{11}$, $L_{13}$, or N.

5. The diamine compound of claim 4, wherein, in Formula 1-4, $X_{11}$ and $X_{12}$ are each independently represented by Formula 2-1;

$X_{11}$ is represented by Formula 2-1, and $X_{12}$ is represented by Formula 2-2;

$X_{11}$ is represented by Formula 2-2, and $X_{12}$ is represented by Formula 2-1; or $X_{11}$ and $X_{12}$ are each independently represented by Formula 2-2.

6. The diamine compound of claim 4, wherein:

$A_{21}$ to $A_{24}$ are each independently selected from a benzene group and a naphthalene group.

7. A diamine compound represented by Formula 1-4:

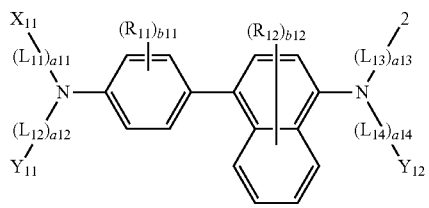

1-4

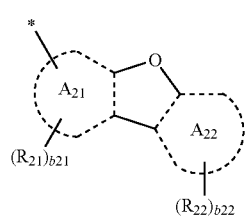

2-1

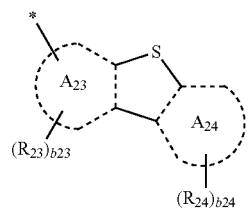

2-2 wherein, in Formula 1-4, $X_{11}$ and $X_{12}$ are each independently represented by one selected from Formulae 2-1 and 2-2, wherein $X_{11}$ and $X_{12}$ are different from each other, and a binding site of Formulae 2-1 or 2-2 in $X_{11}$ and a binding site of Formulae 2-1 or 2-2 in $X_{12}$ are different from each other, $Y_{11}$ and $Y_{12}$ are each independently selected from groups represented by Formulae 5-1 to 5-11:

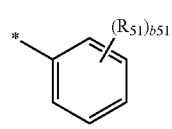

5-1

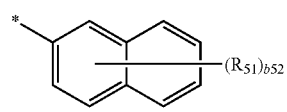

5-2

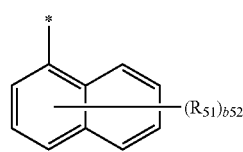

5-3

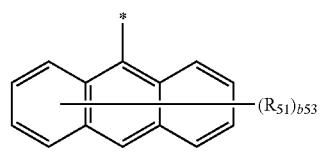

5-4

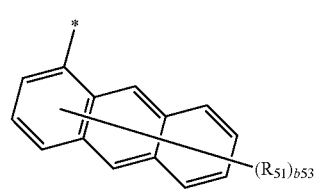

5-5

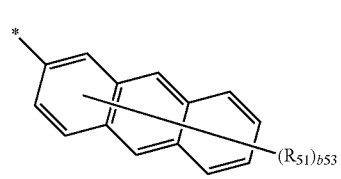

5-6

-continued

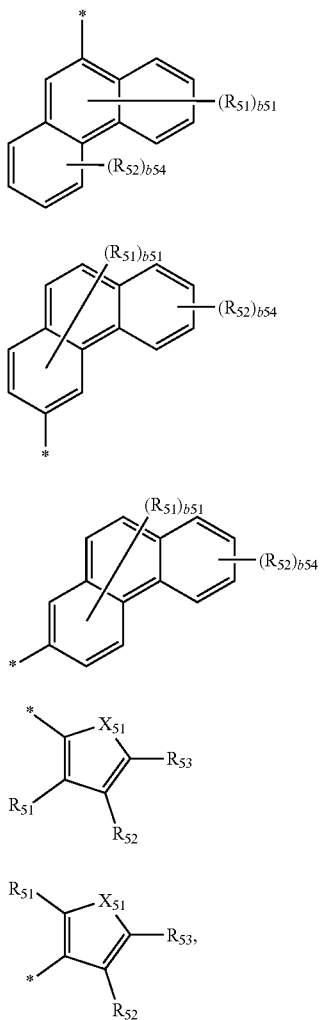

wherein, in Formulae 5-1 to 5-11, $X_{51}$ is selected from O and S, $R_{51}$ to $R_{53}$ are each independently selected from hydrogen, deuterium, —F, —Cl, —Br, —I, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, a furanyl group, and —Si(Q$_1$)(Q$_2$)(Q$_3$), $Q_1$ to $Q_3$ are each independently selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an isopropyl group, an n-butyl group, an isobutyl group, a sec-butyl group, a tert-butyl group, a phenyl group, a biphenyl group, a terphenyl group, and a naphthyl group, b51 is selected from 1, 2, 3, 4, and 5,
b52 is selected from 1, 2, 3, 4, 5, 6, and 7,
b53 is selected from 1, 2, 3, 4, 5, 6, 7, 8, and 9,
b54 is selected from 1, 2, 3, and 4, and
* indicates a binding site to $L_{12}$, $L_{14}$, or N, $L_{11}$ to $L_{14}$ are each independently selected from:
a single bond, a $C_6$-$C_{60}$ arylene group, a $C_1$-$C_{60}$ heteroarylene group, a biphenylene group, and a terphenylene group; and a $C_6$-$C_{60}$ arylene group, a $C_1$-$C_{60}$ heteroarylene group, a biphenylene group, and a terphenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si(Q$_1$)(Q$_2$)(Q$_3$), a11 to a14 are each independently selected from 0, 1, 2, and 3, $R_{11}$ and $R_{12}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si(Q$_1$)(Q$_2$)(Q$_3$), b11 is selected from 1, 2, 3, 4, 5, and 6, and
b12 is selected from 1, 2, 3, and 4, wherein, in Formulae 2-1 and 2-2, $A_{21}$ to $A_{24}$ are each independently selected from a benzene group, a naphthalene group, an anthracene group, a phenanthrene group, a chrysene group, a pyrene group, a pentaphene group, a triphenylene group, and a phenylene group, b21 to b24 are each independently selected from 1, 2, 3, 4, 5, 6, 7, 8, 9, and 10, and $R_{21}$ to $R_{24}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkyl group substituted with at least one selected from deuterium, —F, and a cyano group, a $C_1$-$C_{20}$ alkoxy group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, a terphenyl group, and —Si(Q$_1$)(Q$_2$)(Q$_3$), wherein $Q_1$ to $Q_3$ are each independently selected from hydrogen, deuterium, a $C_1$-$C_{60}$ alkyl group, a $C_1$-$C_{60}$ alkyl group substituted with at least one selected from deuterium, —F, and a cyano group, a $C_6$-$C_{60}$ aryl group, a $C_6$-$C_{60}$ aryl group substituted with at least one selected from deuterium, —F, and a cyano group, a $C_1$-$C_{60}$ heteroaryl group, a biphenyl group, and a terphenyl group, and

* indicates a binding site to $L_{11}$, $L_{13}$, or N.

8. The diamine compound of claim 4, wherein:
$Y_{11}$ and $Y_{12}$ are each independently selected from groups represented by Formulae 6-1 to 6-39:
6-1
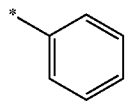
6-2
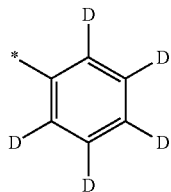
6-3
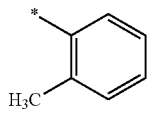
6-4
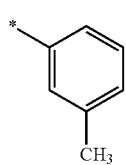
6-5
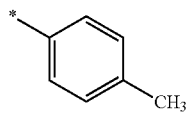
6-6
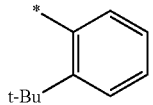
6-7
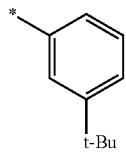
6-8
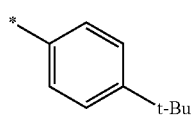
6-9
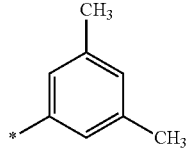
6-10
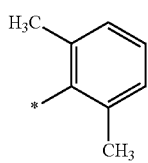
-continued
6-11
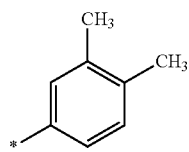
6-12
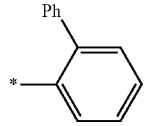
6-13
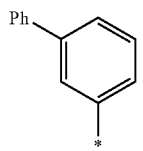
6-14
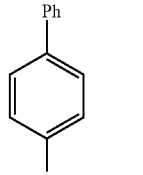
6-15
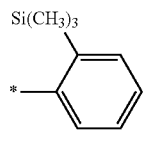
6-16
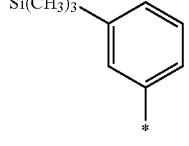
6-17
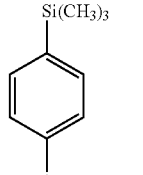
6-18
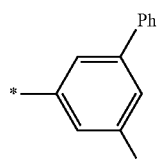
6-19
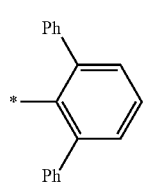

| | |
|---|---|
| 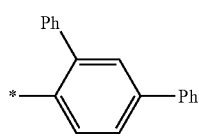 | 6-20 |
| 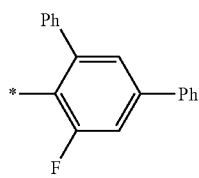 | 6-21 |
| 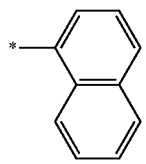 | 6-22 |
|  | 6-23 |
| 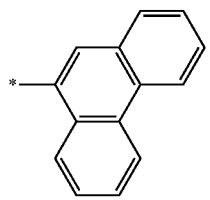 | 6-24 |
| 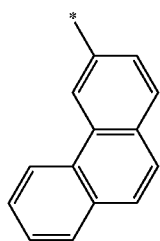 | 6-25 |
| 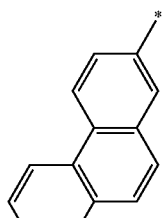 | 6-26 |
| 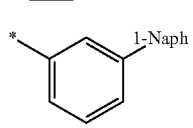 | 6-27 |
| 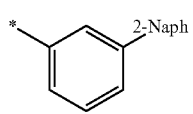 | 6-28 |
| 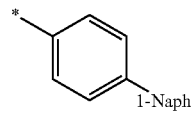 | 6-29 |
| 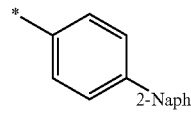 | 6-30 |
| 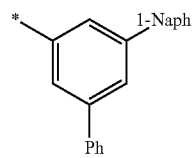 | 6-31 |
| 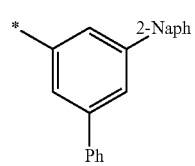 | 6-32 |
| 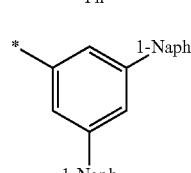 | 6-33 |
| 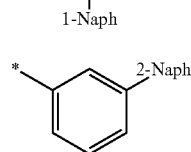 | 6-34 |
| 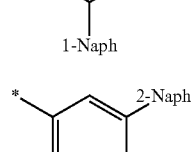 | 6-35 |
| 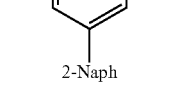 | 6-36 |
| 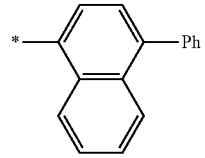 | 6-37 |
| 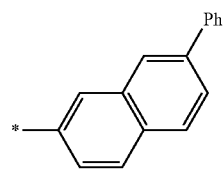 | 6-38 |

6-39 wherein, in Formulae 6-1 to 6-39, t-Bu is a tert-butyl group,

Ph is a phenyl group,

1-Naph is a 1-naphthyl group,

2-Naph is a 2-naphthyl group, and

* indicates a binding site to $L_{12}$, $L_{14}$, or N.

9. The diamine compound of claim 4, wherein:

$L_{11}$ to $L_{14}$ are each independently selected from:

a single bond, a phenylene group, a naphthylene group, a phenanthrenylene group, an anthracenylene group, a triphenylenylene group, a pyrenylene group, a chrysenylenylene group, a thiophenylene group, a furanylene group, a biphenylene group, and a terphenylene group; and a phenylene group, a naphthylene group, a phenanthrenylene group, an anthracenylene group, a triphenylenylene group, a pyrenylene group, a chrysenylenylene group, a thiophenylene group, a furanylene group, a biphenylene group, and a terphenylene group, each substituted with at least one selected from deuterium, —F, —Cl, —Br, —I, a cyano group, —CD$_3$, —CD$_2$H, —CDH$_2$, —CF$_3$, —CF$_2$H, —CFH$_2$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, a butoxy group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, a phenanthrolinyl group, and —Si(Q$_1$)(Q$_2$)(Q$_3$); and $Q_1$ to $Q_3$ are each independently selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, a terphenyl group, and a naphthyl group.

10. The diamine compound of claim 4, wherein:

$L_{11}$ to $L_{14}$ are each independently selected from groups represented by Formulae 3-1 to 3-12:

3-1
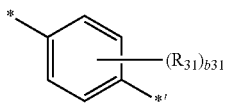

3-2
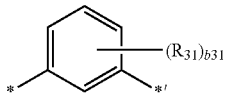

3-3
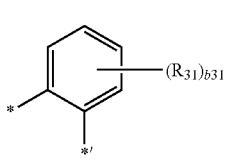

3-4
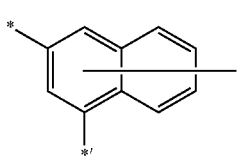

3-5
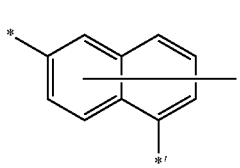

3-6
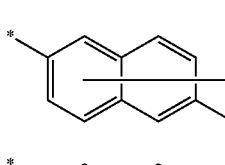

3-7
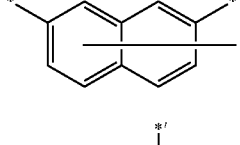

3-8
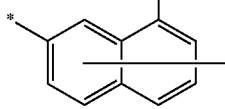

3-9
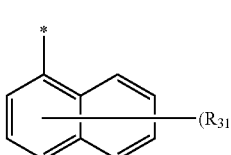

3-10
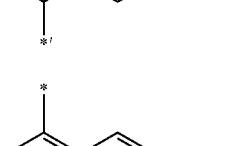

-continued

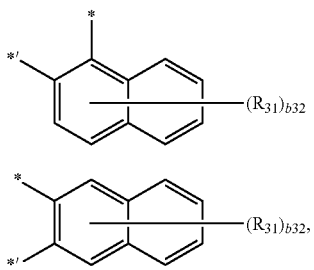

3-11

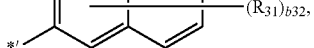

3-12 wherein, in Formulae 3-1 to 3-12,
$R_{31}$ is selected from hydrogen, deuterium, —F, —Cl, —Br, —I, a cyano group, —$CD_3$, —$CD_2H$, —$CDH_2$, —$CF_3$, —$CF_2H$, —$CFH_2$, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a thiophenyl group, a furanyl group, and —$Si(Q_1)(Q_2)(Q_3)$;
$Q_1$ to $Q_3$ are each independently selected from: —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, -$CD_2CD_3$, -$CD_2CD_2H$, and —$CD_2CDH_2$; and
an n-propyl group, an isopropyl group, an n-butyl group, an isobutyl group, a sec-butyl group, a tert-butyl group, a phenyl group, a biphenyl group, a terphenyl group, and a naphthyl group,
b31 is selected from 1, 2, 3, and 4,
b32 is selected from 1, 2, 3, 4, 5, and 6, and
* and *' each indicate a binding site to $L_{11}$, $L_{12}$, $L_{13}$, $L_{14}$, or N.

11. The diamine compound of claim 4, wherein:
$R_{11}$, $R_{12}$, and $R_{21}$ to $R_{24}$ are each independently selected from hydrogen, deuterium, —F, —Cl, —Br, —I, a cyano group, —$CD_3$, -$CD_2H$, —$CDH_2$, —$CF_3$, —$CF_2H$, —$CFH_2$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a methoxy group, an ethoxy group, a propoxy group, a butoxy group, a phenyl group, a biphenyl group, a terphenyl group, a naphthyl group, a phenanthrenyl group, an anthracenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a thiazolyl group, an oxazolyl group, a pyridinyl group, a pyrimidinyl group, a pyridazinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, and a phenanthrolinyl group.

12. The diamine compound of claim 4, wherein:
in Formula 1-4, $X_{11}$ and $X_{12}$ are different from each other and are each independently selected from groups represented by Formulae 2-101 to 2-116 and 2-201 to 2-216:

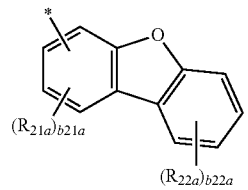

2-101

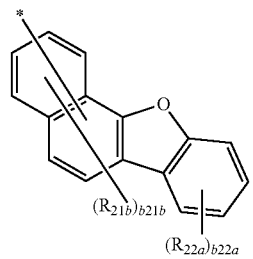

2-102

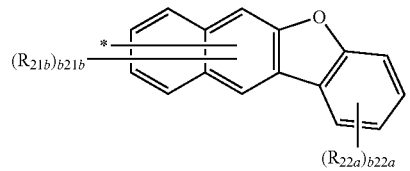

2-103

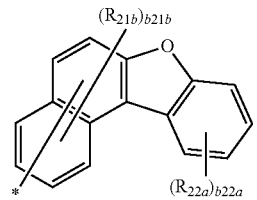

2-104

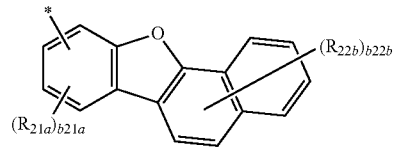

2-105

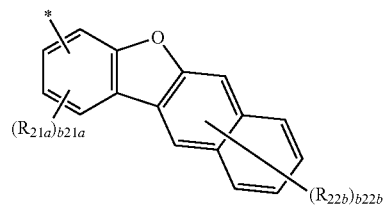

2-106

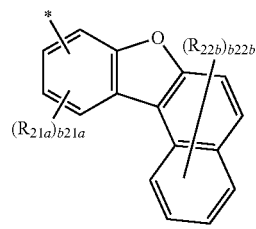

2-107

2-108
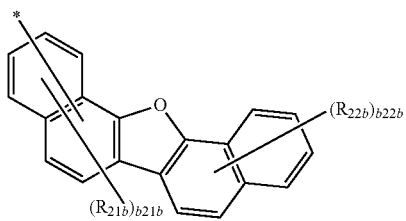
2-109
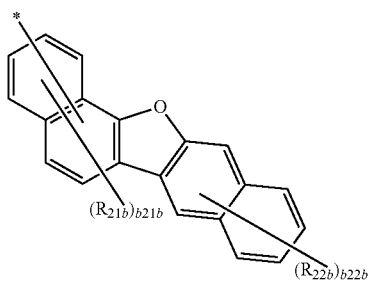
2-110
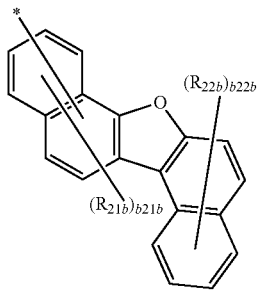
2-111
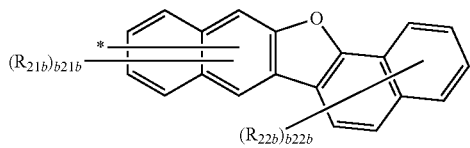
2-112
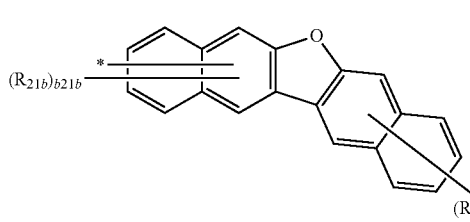
2-113
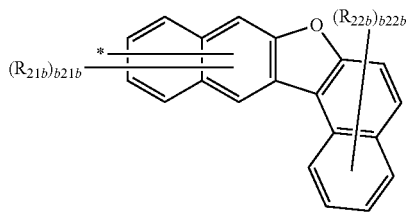
2-114
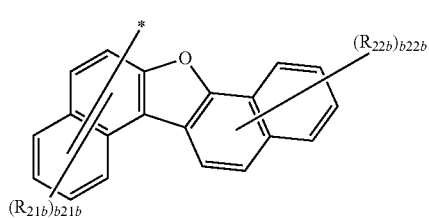
2-115
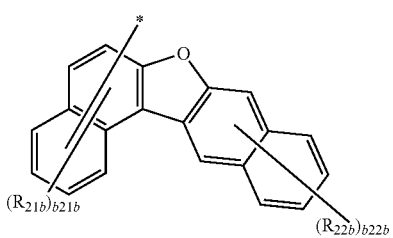
2-116
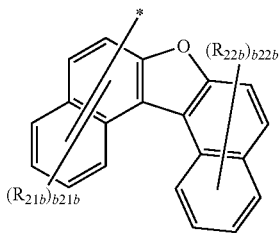
2-201
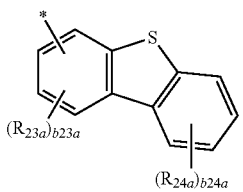
2-202
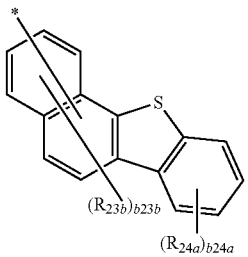
2-203
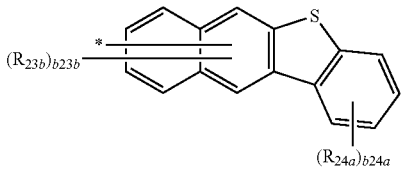
2-204
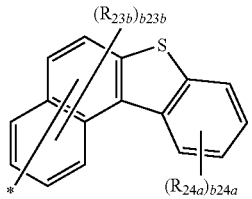
2-205
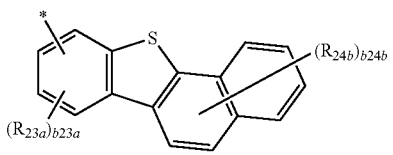

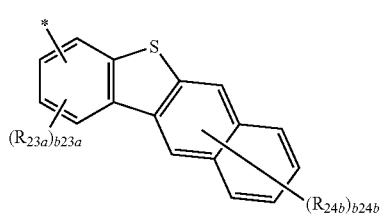
2-206

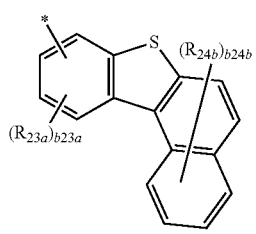
2-207

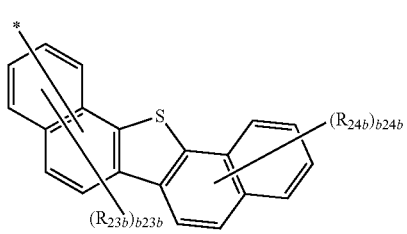
2-208

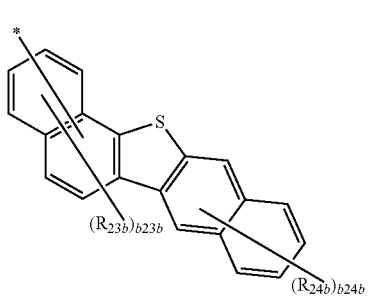
2-209

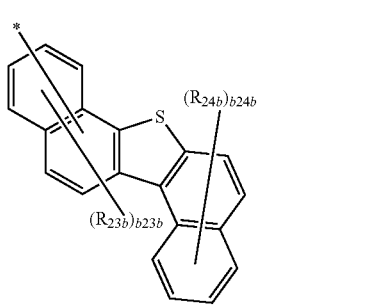
2-210

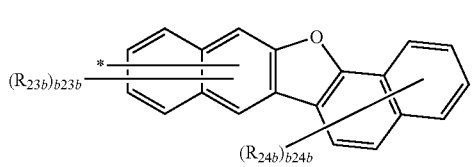
2-211

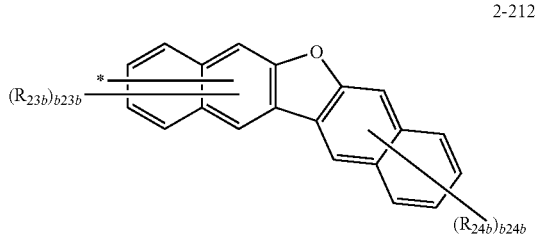
2-212

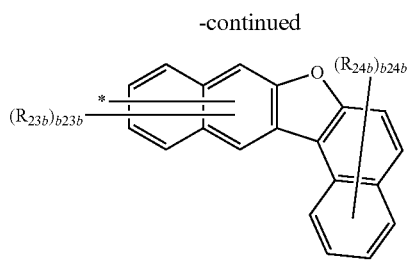
2-213

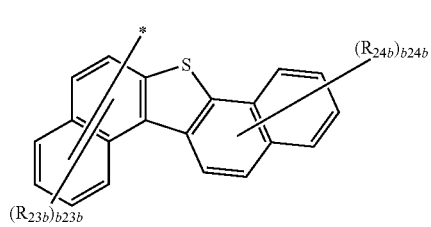
2-214

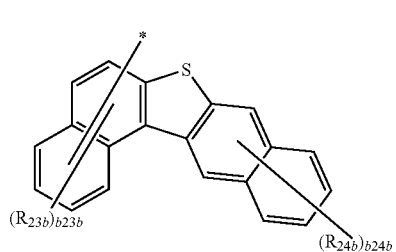
2-215

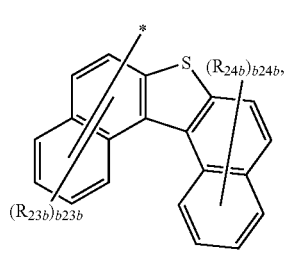
2-216 wherein, in Formulae 2-101 to 2-116 and 2-201 to 2-216, $R_{21a}$, $R_{21b}$, $R_{22a}$, $R_{22b}$, $R_{23a}$, $R_{23b}$, $R_{24a}$, and $R_{24b}$ each independently have the same definition as that of $R_{21}$ to $R_{24}$ in Formulae 2-1 and 2-2, b21a and b23a are each independently selected from 1, 2, and 3, b21b and b23b are each independently selected from 1, 2, 3, 4, and 5, b22a and b24a are each independently selected from 1, 2, 3, and 4, b22b and b24b are each independently selected from 1, 2, 3, 4, 5, and 6, and

* indicates a binding site to $L_{11}$, $L_{13}$, or N.

13. The diamine compound of claim 4, wherein:

in Formula 1-4, $X_{11}$ and $X_{12}$ are different from each other, and $X_{11}$ and $X_{12}$ are each independently selected from groups represented by Formulae 2-101A to 2-101D and 2-201A to 2-201D:

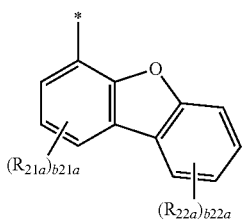
2-101A

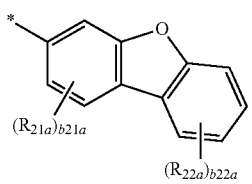
2-101B

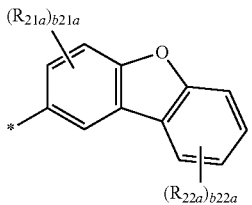
2-101C

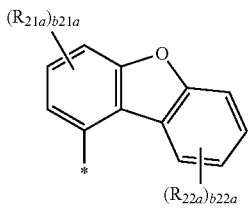
2-101D

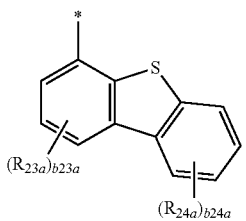
2-201A

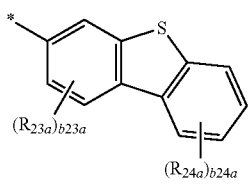
2-201B

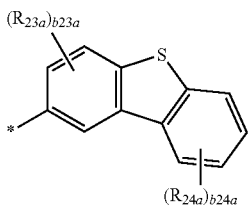
2-201C

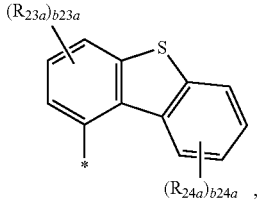
2-201D wherein, in Formulae 2-101A to 2-101D and 2-201A to 2-201D, $R_{21a}$, $R_{22a}$, $R_{23a}$, and $R_{24a}$ each independently have the same definition as that of $R_{21}$ to $R_{24}$ in Formulae 2-1 and 2-2, b21a and b23a are each independently selected from 1, 2, and 3, b22a and b24a are each independently selected from 1, 2, 3, and 4, and

* indicates a binding site to $L_{11}$, $L_{13}$, or N.

14. The diamine compound of claim 13, wherein, in Formula 1-4, $X_{11}$ is represented by Formula 2-101A, and $X_{12}$ is represented by one selected from Formulae 2-101B to 2-101D and 2-201A to 2-201D;

$X_{11}$ is represented by Formula 2-101B, and $X_{12}$ is represented by one selected from Formulae 2-101A, 2-101C, 2-101 D, and 2-201A to 2-201D;

$X_{11}$ is represented by Formula 2-101C, and $X_{12}$ is represented by one selected from Formulae 2-101A, 2-101B, 2-101 D, and 2-201A to 2-201D;

$X_{11}$ is represented by Formula 2-101 D, and $X_{12}$ is represented by one selected from Formulae 2-101A to 2-101C and 2-201A to 2-201D;

$X_{11}$ is represented by Formula 2-201A, and $X_{12}$ is represented by one selected from Formulae 2-101A to 2-101D and 2-201B to 2-201D;

$X_{11}$ is represented by Formula 2-201B, and $X_{12}$ is represented by one selected from Formulae 2-101A to 2-101D, 2-201A, 2-201C, and 2-201D;

$X_{11}$ is represented by Formula 2-201C, and $X_{12}$ is represented by one selected from Formulae 2-101A to 2-101D, 2-201A, 2-201B, and 2-201D; or $X_{11}$ is represented by Formula 2-201 D, and $X_{12}$ is represented by one selected from Formulae 2-101A to 2-101D and 2-201A to 2-201C.

15. The diamine compound of claim 13, wherein, in Formula 1-4, $X_{11}$ is represented by Formula 2-101A, and $X_{12}$ is represented by one selected from Formulae 2-101B to 2-101D and 2-201B to 2-201D;

$X_{11}$ is represented by Formula 2-101B, and $X_{12}$ is represented by one selected from Formulae 2-101A, 2-101C, 2-101D, 2-201A, 2-201C, and 2-201D;

$X_{11}$ is represented by Formula 2-101C, and $X_{12}$ is represented by one selected from Formulae 2-101A, 2-101B, 2-101D, 2-201A, 2-201B, and 2-201D;

$X_{11}$ is represented by Formula 2-101 D, and $X_{12}$ is represented by one selected from Formulae 2-101A to 2-101C and 2-201A to 2-201C;

$X_{11}$ is represented by Formula 2-201A, and $X_{12}$ is represented by one selected from Formulae 2-101B to 2-101D and 2-201B to 2-201D;

$X_{11}$ is represented by Formula 2-201B, and $X_{12}$ is represented by one selected from Formulae 2-101A, 2-101C, 2-101D, 2-201A, 2-201C, and 2-201D;

$X_{11}$ is represented by Formula 2-201C, and $X_{12}$ is represented by one selected from Formulae 2-101A, 2-101B, 2-101D, 2-201A, 2-201B, and 2-201D; or $X_{11}$ is represented by Formula 2-201 D, and $X_{12}$ is represented by one selected from Formulae 2-101A to 2-101C and 2-201A to 2-201C.

16. The diamine compound of claim 4, wherein:
the diamine compound is represented by Formula 1-14:

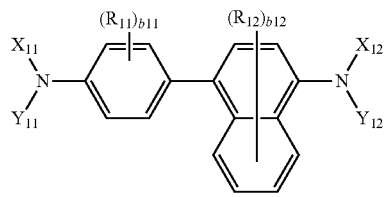

1-14

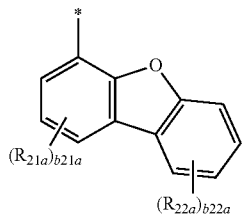

2-101A 2-101B 2-101C 2-101D 2-201A

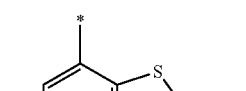

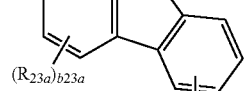

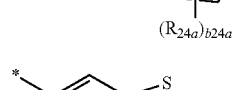

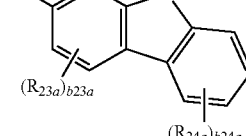

2-201B

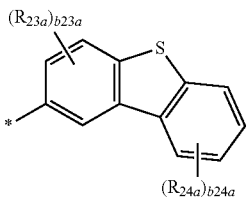

2-201C

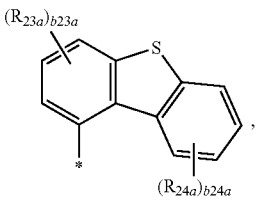

2-201D wherein, in Formula 1-14:
$X_{11}$ is represented by Formula 2-101A, and $X_{12}$ is represented by one selected from Formulae 2-101B to 2-101D and 2-201A to 2-201D;

$X_{11}$ is represented by Formula 2-101B, and $X_{12}$ is represented by one selected from Formulae 2-101A, 2-101C, 2-101 D, and 2-201A to 2-201D;

$X_{11}$ is represented by Formula 2-101C, and $X_{12}$ is represented by one selected from Formulae 2-101A, 2-101B, 2-101 D, and 2-201A to 2-201D;

$X_{11}$ is represented by Formula 2-101 D, and $X_{12}$ is represented by one selected from Formulae 2-101A to 2-101C and 2-201A to 2-201D;

$X_{11}$ is represented by Formula 2-201A, and $X_{12}$ is represented by one selected from Formulae 2-101A to 2-101D and 2-201B to 2-201D;

$X_{11}$ is represented by Formula 2-201B, and $X_{12}$ is represented by one selected from Formulae 2-101A to 2-101D, 2-201A, 2-201C, and 2-201 D;

$X_{11}$ is represented by Formula 2-201C, and $X_{12}$ is represented by one selected from Formulae 2-101A to 2-101D, 2-201A, 2-201B, and 2-201D; or $X_{11}$ is represented by Formula 2-201 D, and $X_{12}$ is represented by one selected from Formulae 2-101A to 2-101D and 2-201A to 2-201C, and wherein, in Formula 1-14, 2-101A to 2-101D, and 2-201A to 2-201D, $Y_{11}$ and $Y_{12}$, $R_{11}$, $R_{12}$, $R_{21}$ to $R_{24}$, b11, and b12 are each independently as defined with respect to Formulae 1-4, 2-1, and 2-2.

17. The diamine compound of claim 4, wherein:
the diamine compound is selected from Compounds 1 to 36:

1

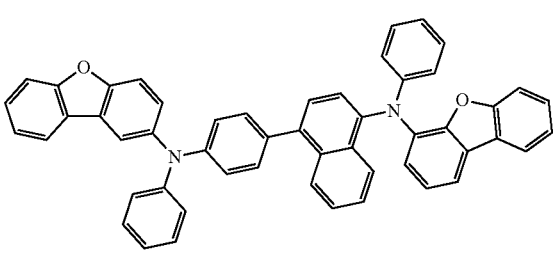

2
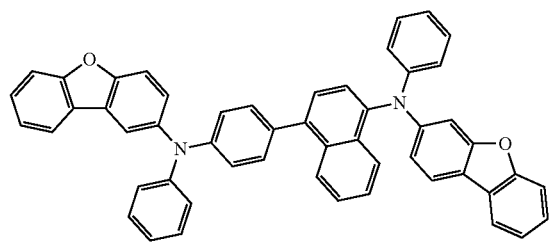
3
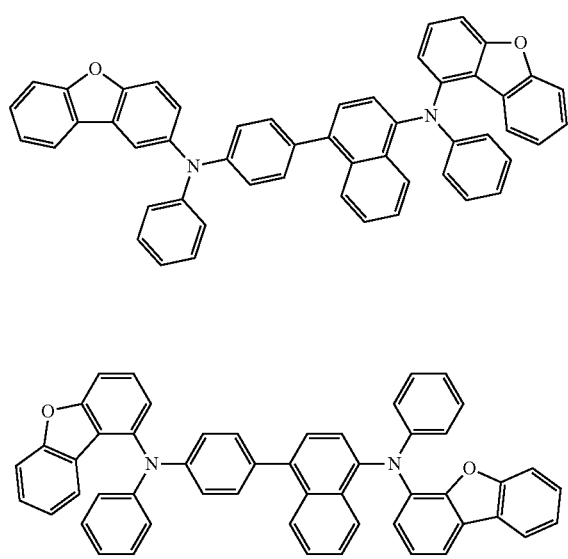
4
5
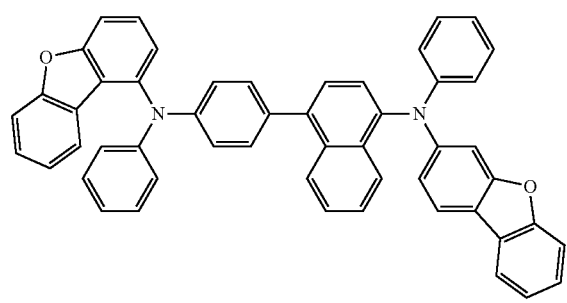
6
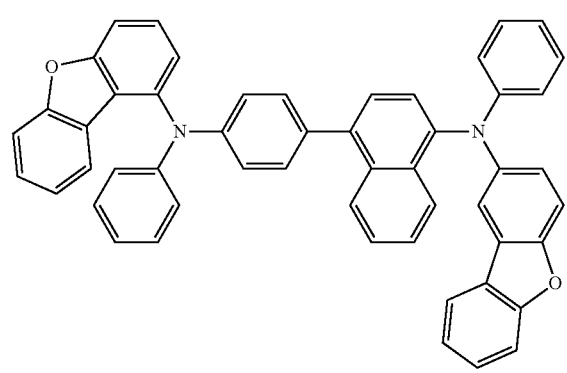
7
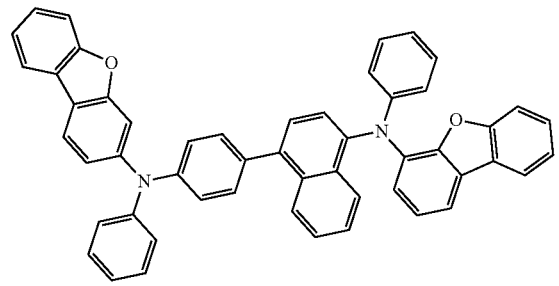
8
9
10
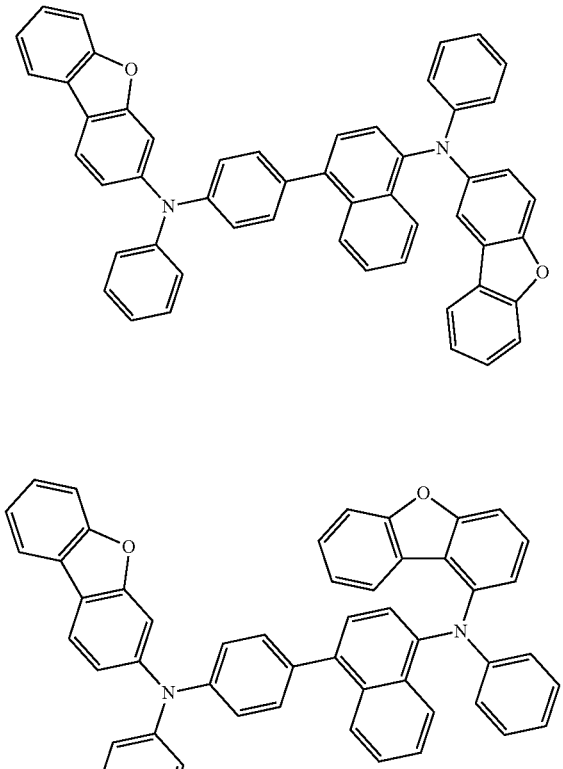

11
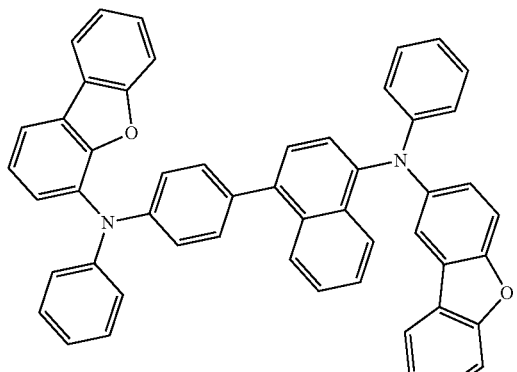
12
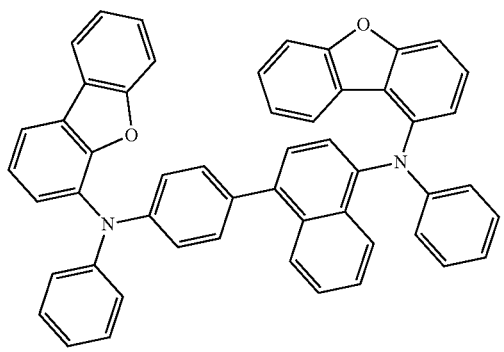
13
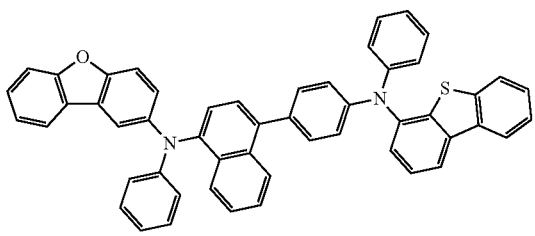
14
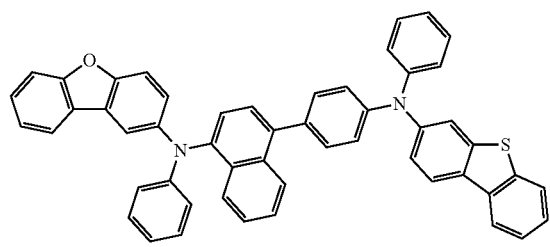
15
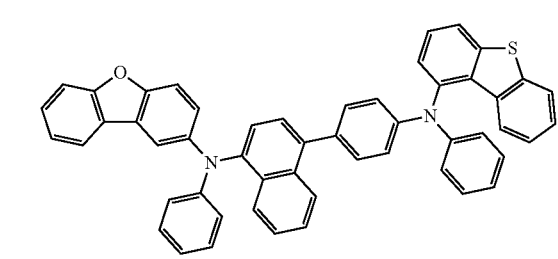
16
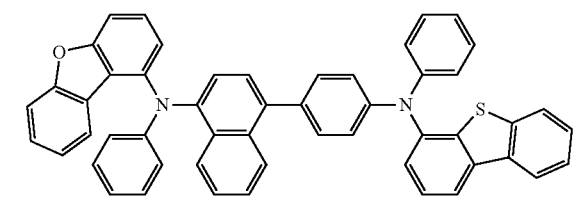
17
18
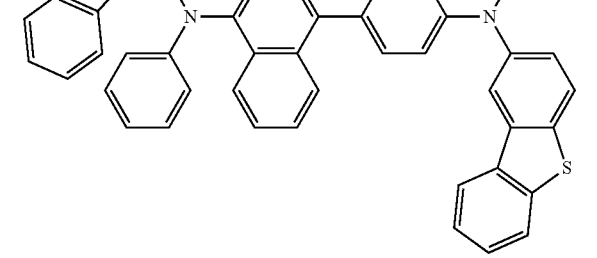
19
20

21
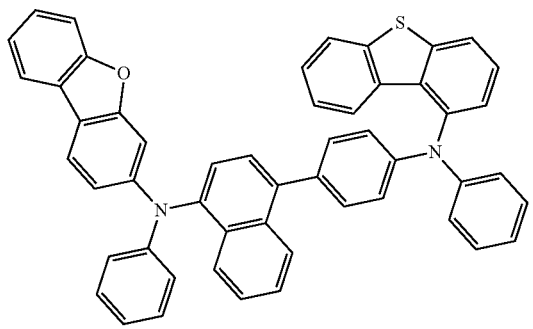
22
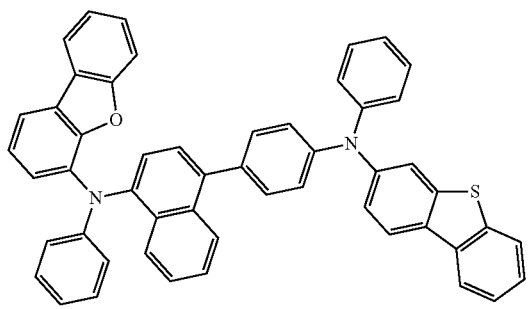
23
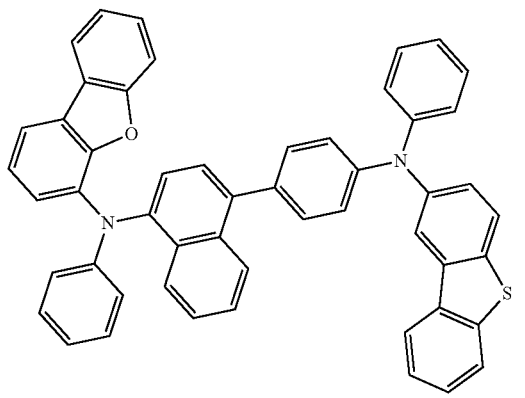
24
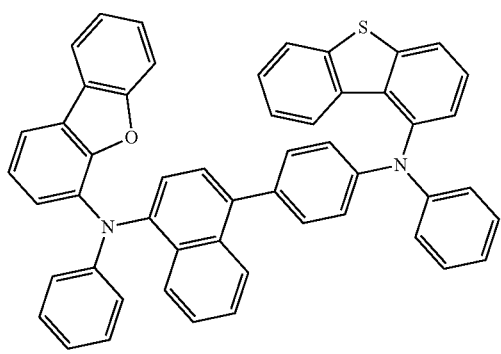
25
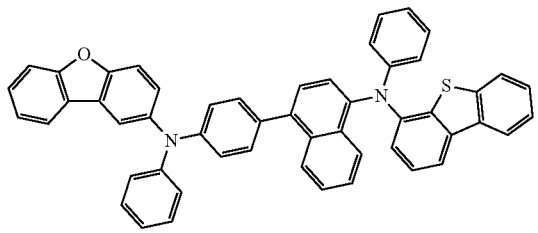
26
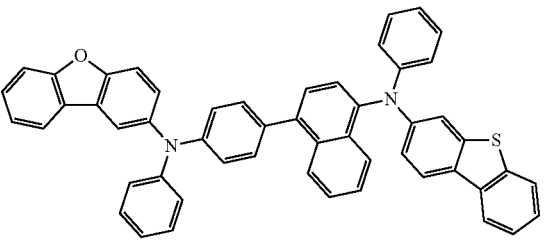
27
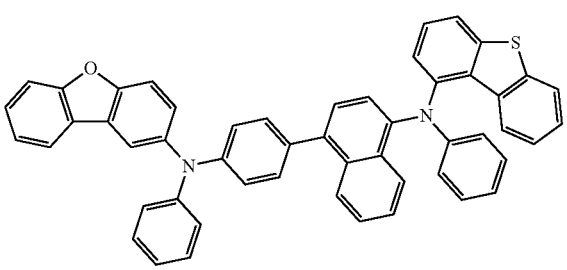
28
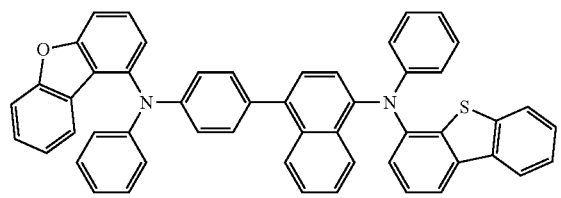
29
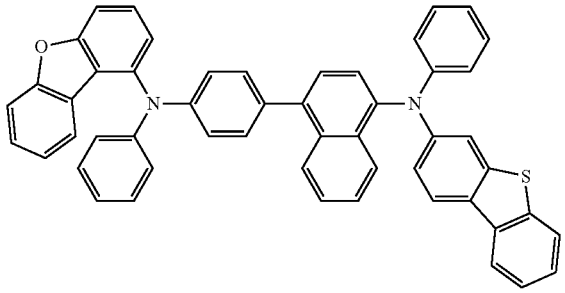

30
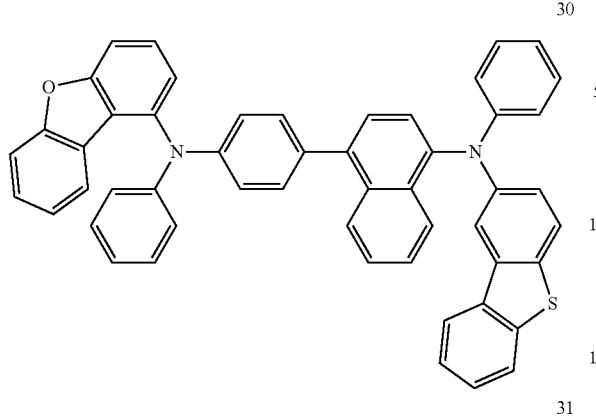
31
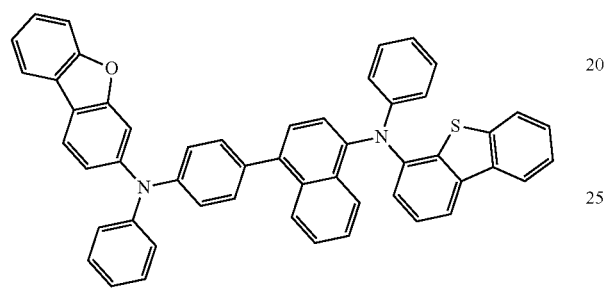
32
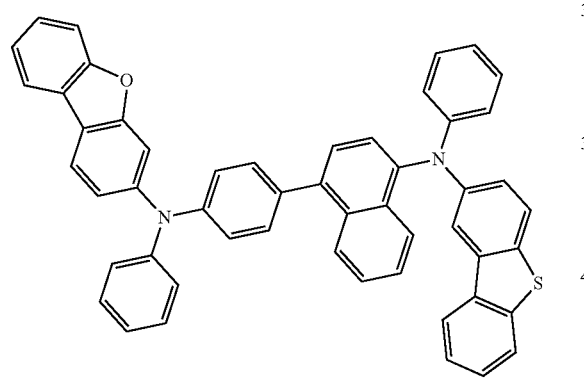
33
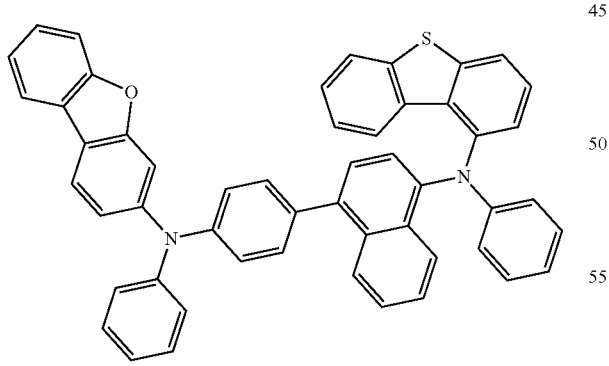
34
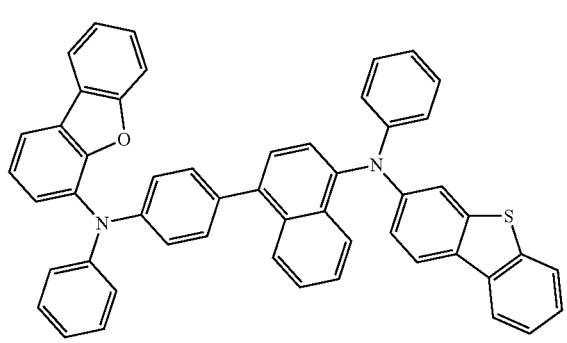
35
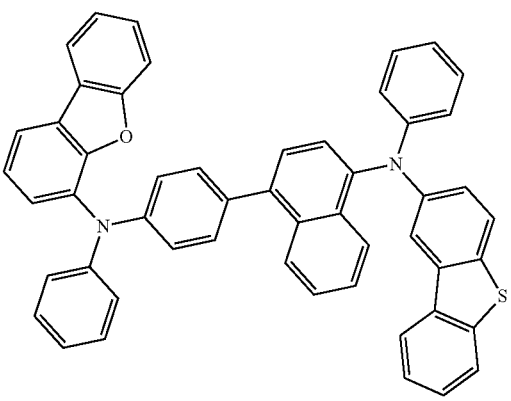
36
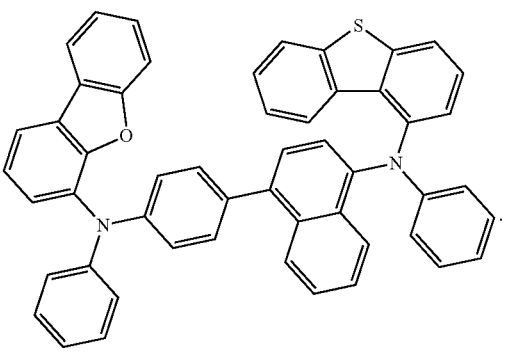
* * * * *

UNITED STATES PATENT AND TRADEMARK OFFICE
CERTIFICATE OF CORRECTION

PATENT NO. : 11,802,116 B2
APPLICATION NO. : 16/293299
DATED : October 31, 2023
INVENTOR(S) : Jongwoo Kim et al.

Page 1 of 2

It is certified that error appears in the above-identified patent and that said Letters Patent is hereby corrected as shown below:

In the Claims

In Column 165, Lines 50-59, in Claim 7, in Formula 1-4, delete " 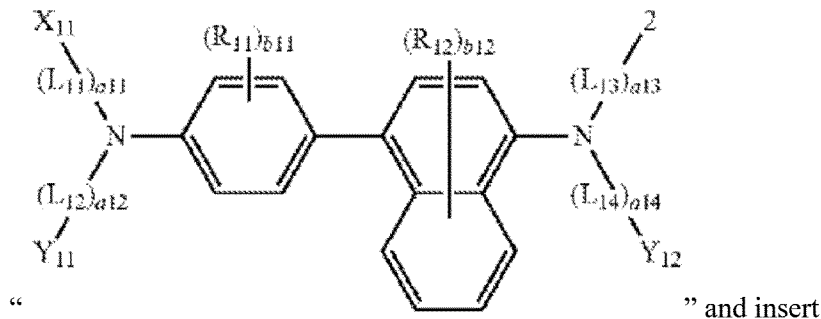 " and insert

--

--.

In Column 175, Lines 29-30, in Claim 10, delete "—CHDCD$_3$,-CD$_2$CD$_3$,-CD$_2$CD$_2$H," and insert -- —CHDCD$_3$, —CD$_2$CD$_3$, —CD$_2$CD$_2$H, --.

In Column 182, Line 29, in Claim 14, delete "2-101 D," and insert -- 2-101D, --.

In Column 182, Line 32, in Claim 14, delete "2-101 D," and insert -- 2-101D, --.

In Column 182, Line 33, in Claim 14, delete "2-101 D," and insert -- 2-101D, --.

Signed and Sealed this
Thirteenth Day of February, 2024

Katherine Kelly Vidal
*Director of the United States Patent and Trademark Office*

CERTIFICATE OF CORRECTION (continued)
U.S. Pat. No. 11,802,116 B2

In Column 182, Line 45, in Claim 14, delete "2-201 D," and insert -- 2-201D, --.

In Column 182, Line 59, in Claim 15, delete "2-101 D," and insert -- 2-101D, --.

In Column 183, Line 4, in Claim 15, delete "2-201 D," and insert -- 2-201D, --.

In Column 184, Line 26, in Claim 16, delete "2-101 D," and insert -- 2-101D, --.

In Column 184, Line 30, in Claim 16, delete "2-101 D," and insert -- 2-101D, --.

In Column 184, Line 31, in Claim 16, delete "2-101 D," and insert -- 2-101D, --.

In Column 184, Line 39, in Claim 16, delete "2-201 D;" and insert -- 2-201D; --.

In Column 184, Line 44, in Claim 16, delete "2-201 D," and insert -- 2-201D, --.